United States Patent
Noguchi et al.

(10) Patent No.: US 8,969,383 B2
(45) Date of Patent: Mar. 3, 2015

(54) PICOLINAMIDE DERIVATIVES AS TTX-S BLOCKERS

(71) Applicant: RaQualia Pharma Inc., Aichi (JP)

(72) Inventors: Hirohide Noguchi, Aichi (JP); Tadashi Inoue, Aichi (JP); Mikio Morita, Aichi (JP); Yoshimasa Arano, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 0 days.

(21) Appl. No.: 14/302,572

(22) Filed: Jun. 12, 2014

(65) Prior Publication Data

US 2014/0296237 A1    Oct. 2, 2014

Related U.S. Application Data

(62) Division of application No. 13/388,740, filed as application No. PCT/JP2010/004917 on Aug. 4, 2010, now Pat. No. 8,809,380.

(60) Provisional application No. 61/213,978, filed on Aug. 4, 2009.

(51) Int. Cl.
| | |
|---|---|
| C07D 401/14 | (2006.01) |
| C07D 401/12 | (2006.01) |
| A61K 31/4433 | (2006.01) |
| A61K 31/4439 | (2006.01) |
| A61K 31/497 | (2006.01) |
| A61K 31/5377 | (2006.01) |
| C07D 405/14 | (2006.01) |
| C07D 413/14 | (2006.01) |
| C07D 417/14 | (2006.01) |

(52) U.S. Cl.
CPC .......... *C07D 401/12* (2013.01); *A61K 31/4433* (2013.01); *A61K 31/4439* (2013.01); *A61K 31/497* (2013.01); *A61K 31/5377* (2013.01); *C07D 401/14* (2013.01); *C07D 405/14* (2013.01); *C07D 413/14* (2013.01); *C07D 417/14* (2013.01)
USPC ................... 514/318; 514/235.5; 514/255.05; 514/256; 514/333; 514/339; 514/343; 546/193; 546/256; 546/272.1; 546/275.4; 546/278.1; 544/131; 544/333; 544/405

(58) Field of Classification Search
CPC ... C07D 401/12; C07D 401/14; C07D 413/14
USPC ......... 514/235.5, 255.05, 256, 318, 333, 339, 514/343; 546/193, 272.1, 275.4, 278.1; 544/131, 333, 405
See application file for complete search history.

(56) References Cited

U.S. PATENT DOCUMENTS

| | | |
|---|---|---|
| 6,784,192 B2 | 8/2004 | Ozaki et al. |
| 7,649,004 B2 | 1/2010 | Lane et al. |
| 2003/0220368 A1 | 11/2003 | Ozaki et al. |
| 2008/0070898 A1 | 3/2008 | Kikuchi et al. |
| 2008/0300243 A1 | 12/2008 | Kelly et al. |

FOREIGN PATENT DOCUMENTS

| | | |
|---|---|---|
| JP | 2001-270883 | 10/2001 |
| JP | 2008-531690 | 8/2008 |
| WO | 2004/011430 | 2/2004 |
| WO | 2006/025471 | 3/2006 |

OTHER PUBLICATIONS

Fang et al. "Preparation of piperidine . . . " Casreact 149:53877 (2008).*
International Search Report issued Nov. 9, 2010 in International (PCT) Application No. PCT/JP2010/004917 along with the Written Opinion.
RN 791770-34-8 File Registry (2004).
"Improper Markush" Fed. Reg. vol. 76(27) p. 7162-7175, training slides 1, 64-67 (2011).
Kim et al. "The changes in expression . . . " Mol. Brain Res. 95 p. 153-161 (2001).
Lyu et al. "Low dose of . . . " Brain Res. 871 p. 98-103 (2000).
Riluzole Wipkipedia p. 1-2 (2013).

* cited by examiner

*Primary Examiner* — Celia Chang
(74) *Attorney, Agent, or Firm* — Wenderoth, Lind & Ponack. L.L.P.

(57) ABSTRACT

The present invention relates to picolinamide derivatives which have blocking activities of voltage gated sodium channels as the TTX-S channels, and which are useful in the treatment or prevention of disorders and diseases in which voltage gated sodium channels are involved. The invention also relates to pharmaceutical compositions comprising these compounds and the use of these compounds and compositions in the prevention or treatment of such diseases in which voltage gated sodium channels are involved.

5 Claims, No Drawings

PICOLINAMIDE DERIVATIVES AS TTX-S BLOCKERS

This application is a divisional application of U.S. application Ser. No. 13/388,740, filed Feb. 3, 2012, which is a U.S. national stage of International Application No. PCT/JP2010/004917, filed Aug. 4, 2010, which claims the benefit of U.S. provisional application Ser. No. 61/213,978, filed Aug. 4, 2009.

TECHNICAL FIELD

The present invention relates to picolinamide derivatives which have blocking activities of voltage gated sodium channels as the TTX-S channels, and which are useful in the treatment or prevention of disorders and diseases in which voltage gated sodium channels are involved. The invention also relates to pharmaceutical compositions comprising these compounds and the use of these compounds and compositions in the prevention or treatment of such diseases in which voltage gated sodium channels are involved.

BACKGROUND ART

The picolinamide derivatives of the present invention are sodium channel blockers and have a number of therapeutic applications, particularly in the treatment of pain.

More particularly, the picolinamide derivatives of the invention are selective tetrodotoxin-sensitive (TTX-S) blockers. In the discussion that follows, the invention is exemplified by reference to the inhibition of $Na_{v1.3}$ and $Na_{v1.7}$ channels as the TTX-S channels. They show the affinity for both $Na_{v1.3}$ and $Na_{v1.7}$ channels which is significantly greater than their affinity for $Na_{v1.5}$ channel as the tetrodotoxin-resistant (TTX-R) sodium channels. Preferred picolinamide derivatives of the invention show at least a 10-fold selectivity for the $Na_{v1.3}$ and $Na_{v1.7}$ channels as compared with $Na_{v1.5}$ channel.

The rat $Na_{v1.3}$ channel and the human $Na_{v1.3}$ channel have been cloned in 1988 and 1998/2000 respectively (FEBS Lett. 228 (1), 187-194, 1988; J. Mol. Neurosci., 10 (1), 67-70, 1998; Eur. J. Neurosci. 12 (12), 4281-4289, 2000). The $Na_{v1.3}$ channel was formerly known as brain type III sodium channel. $Na_{v1.3}$ is present at relatively high levels in the nervous system of rat embryos but is barely detectable in adult rats. $Na_{v1.3}$ is up-regulated following axotomy in the Spinal Nerve Ligation (SNL), Chronic Constriction Injury (CCI), and diabetic neuropathy models (J Neurophysiol 82, 2776-2785, 1999. J. A. Black et al.; Ann Neurol 52, 786-792, 2002. M. J. Cranner et al.; Pain 83, 591-600, 1999. S. Dib-Hajj et al.; J Biol Chem 279, 29341-29350, 2004. S. Hong et al.; Mol Brain Res 95, 153-161, 2001. C. H. Kim et al.) The up-regulation of $Na_{v1.3}$ channel contributes to rapidly repriming sodium current in small dorsal root ganglion (DRG) neurons (J Neurophysiol 82, 2776-2785, 1999. J. A. Black et al.). These observations suggest that $Na_{v1.3}$ may make a key contribution to neuronal hyperexcitability.

In order to validate the contribution of $Na_{v1.3}$ sodium channel in the pain states, specific antisense oligonucleotides (ASO) were used in animal pain models. $Na_{v1.3}$ sodium channel ASO treatment significantly attenuated pain-related behaviors after CCI operation (J. Neurosci. 24, 4832-4839, 2004, Hains, B. C. et al.). These finding suggest that $Na_{v1.3}$ sodium channel blocker is useful to treat neuropathic pain conditions.

The $Na_{v1.7}$ channel appears to be the best 'validated' pain target. The most exciting findings with respect to $Na_{v1.7}$ have come from human genetic studies. Cox et al. (Nature 444, 894-898, 2006) discovered SCN9A mutations that cause a loss of $Na_{v1.7}$ function in three families from Pakistan. Their observations link loss of $Na_{v1.7}$ function with a congenital inability to experience pain, adding to the evidence indicating $Na_{v1.7}$ channel as an essential participant in human nociception.

By contrast, Gain-of-function mutations have also been described that lead to enhanced pain, for example, Primary Erythermalgia in one case and Paroxysmal Extreme Pain Disorder in another. These gain-of-function mutations in patients led to different types of gating changes in $Na_{v1.7}$ sodium currents and, interestingly, different degrees of effectiveness of specific sodium channel blocking drugs. The implication from these findings is that a selective $Na_{v1.7}$ blocker may be an effective treatment for pain in man.

A local anaesthetic lidocaine and a volatile anaesthetic halothane are known to act on both TTX-R and TTX-S sodium channels with poor selectivity and low potency ($IC_{50}$ values range from 50 microM to 10 mM). These anaesthetics at high systemic concentrations could cause devastating side effects, e.g., paralysis and cardiac arrest. However, systemic administration of lidocaine at low concentrations is effective to treat chronic pain (Trends in Pharm. Sci 22, 27-31, 2001, Baker, M. D. et al.). In rats, application of a very low dose of TTX to the DRG of the injured segment of the L5 spinal nerve significantly reduces mechanical allodynic behavior (Brain Res 871, 98-103, 2000, Lyu, Y. S. et al.). This suggests that TTX-S subtypes of sodium channels play an important role in maintaining allodynic behaviors in an animal model of neuropathic pain.

The $Na_{v1.5}$ channel is also a member of TTX-resistant sodium channels. The $Na_{v1.5}$ channel is almost exclusively expressed in cardiac tissue and has been shown to underlie a variety of cardiac arrhythmias and conduction disorders.

SUMMARY OF INVENTION

Technical Problem

It is an objective of the invention to provide new TTX-S blockers that are good drug candidates. Preferred compounds should bind potently to the TTX-S ($Na_{v1.3}$ and $Na_{v1.7}$) channels whilst showing little affinity for other sodium channels, particularly the $Na_{v1.5}$ channel. They should be well absorbed from the gastrointestinal tract, be metabolically stable and possess favorable pharmacokinetic properties. They should be non-toxic and demonstrate few side-effects. Furthermore, the ideal drug candidate will exist in a physical form that is stable, non-hygroscopic and easily formulated.

In particular, the picolinamide derivatives of the present invention are selective for the TTX-S channels over the $Na_{v1.5}$ channel, leading to improvements in the side-effect profile.

The picolinamide derivatives of the present invention are therefore useful in the treatment of a wide range of disorders, particularly pain, acute pain, chronic pain, neuropathic pain, inflammatory pain, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back and orofacial pain.

Other conditions that may be treated with the picolinamide derivatives of the present invention include multiple sclerosis, neurodegenerative disorders, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia.

Structurally close compounds are disclosed in WO 2007085565. However, the patent only disclosed halogen or alkyl group and never mentioned the amide group as a substituent at the 2-position on the pyridine ring, which is quite different from the compounds of this invention. In addition the compounds in WO 2007085565 are useful for the combating pests, whereas the compounds of this invention are useful for the treatment of a condition or disorder mediated by TTX-S channel described in the former paragraph.

Solution to Problem

The present invention is directed to picolinamide derivatives compounds which are TTX-S blockers over the $Na_{V1.5}$ channel, and which are useful in the treatment or prevention of neurological and psychiatric disorders and diseases in which TTX-S channels are involved. The invention is also directed to pharmaceutical compositions comprising these compounds and the use of these compounds and compositions in the prevention or treatment of such diseases in which TTX-S sodium channels are involved.

The present invention provides compounds of formula (I) and salts thereof:

[Chem. 1]

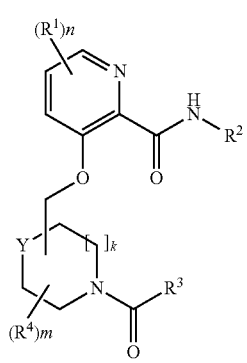

(I)

wherein:
$R^1$ is independently selected from the group consisting of:
(1) hydrogen, (2) halogen, (3) hydroxy, (4) —$O_p$—$C_{1-6}$ alkyl, where the alkyl is unsubstituted or substituted with one or more substituents selected from $R^5$, (5) —$O_p$—$C_{3-8}$ cycloalkyl, where the cycloalkyl is unsubstituted or substituted with one or more substituents selected from $R^5$, (6) $C_{2-4}$ alkenyl, where the alkenyl is unsubstituted or substituted with one or more substituents selected from $R^5$, (7) —(C=O)—$NR^6R^7$, (8) —$NR^6R^7$, (9) —$S(O)_2$—$NR^6R^7$, (10) —$NR^6$—$S(O)_2R^7$, (11) —$S(O)_r$—$R^8$, where r is 0, 1 or 2 and where $R^8$ is selected from the definitions of $R^6$ and $R^7$, (12) —$CO_2H$, and (13) —CN; where p is 0 or 1 (wherein if p is 0, a chemical bond is present in the place of $O_p$);
n is 1, 2, or 3; when n is two or more than two, $R^1$ may be same or different;

$R^2$ is selected from the group consisting of:
(1) hydrogen, (2) $C_{1-6}$ alkyl, which is unsubstituted or substituted with one or more substituents selected from $R^5$, (3) $C_{3-8}$ cycloalkyl which is unsubstituted or substituted with one or more substituents selected from $R^5$, (4) phenyl, which is unsubstituted or substituted with one or more substituents selected from $R^5$, and (5) heterocycle, which is unsubstituted or substituted with one or more substituents selected from $R^5$;
$R^3$ is selected from the group consisting of:
(1) —$C_{0-3}$ alkyl-$O_p$—$C_{0-3}$ alkyl-cycloalkyl which is unsubstituted or substituted with one or more substituents selected from $R^5$, (2) —$C_{0-3}$ alkyl-$O_p$—$C_{0-3}$ alkyl-phenyl, which is unsubstituted or substituted with one or more substituents selected from $R^5$, and (3) —$C_{0-3}$ alkyl-$O_p$—$C_{0-3}$ alkyl-heterocycle, which is unsubstituted or substituted with one or more substituents selected from $R^5$; where p is 0 or 1, (wherein if p is 0, a chemical bond is present in the place of $O_p$);
$R^4$ is selected from the group consisting of:
(1) hydrogen, (2) $C_{1-6}$ alkyl, and (3) hydroxy;
m is 1, 2, or 3; when m is two or more than two, $R^4$ may be same or different; $R^4$ may form the bond with any of carbon atom on the cyclic amine ring;
k is 0 or 1;
Y is oxygen atom or carbon atom;
$R^5$ is selected from the group consisting of:
(1) halogen, (2) hydroxy, (3) —(C=O)$_q$—$O_r$—$C_{1-6}$ alkyl, where the alkyl is unsubstituted or substituted with one or more substituents selected from $R^9$, (4) —$O_p$—(C$_{1-3}$) perfluoroalkyl, (5) —(C=O)$_q$—$O_r$—$C_{3-8}$ cycloalkyl, where the cycloalkyl is unsubstituted or substituted with one or more substituents selected from $R^9$, (6) —(C=O)$_q$—$O_r$—$C_{2-4}$ alkenyl, where the alkenyl is unsubstituted or substituted with one or more substituents selected from $R^9$, (7) —(C=O)$_q$—$O_r$-phenyl or —(C=O)$_q$—$O_r$-napthyl, where the phenyl or napthyl is unsubstituted or substituted with one or more substituents selected from $R^9$, (8) —(C=O)$_q$—$O_r$-heterocycle, where the heterocycle is unsubstituted or substituted with one or more substituents selected from $R^9$, (9) —(C=O)—$NR^6R^7$, (10) —$NR^6R^7$, (11) —$S(O)_2$—$NR^6R^7$, (12) —$S(O)_t$—$R^8$, where t is 0, 1 or 2, (13) —$CO_2H$, (14) —CN, and (15) —$NO_2$; where p is 0 or 1, (wherein if p is 0, a chemical bond is present in the place of $O_p$) and where q is 0 or 1 and r is 0 or 1 (wherein if q is 0 or r is 0, a bond is present in the place of (C=O)$_q$ or $O_r$, and wherein if q is 0 and r is 0, a single bond is present in the place of (C=O)$_q$—$O_r$);
$R^6$ and $R^7$ are independently selected from the group consisting of:
(1) hydrogen, (2) $C_{1-6}$ alkyl, which is unsubstituted or substituted with $R^5$, (3) $C_{3-6}$ alkenyl, which is unsubstituted or substituted with $R^5$, (4) $C_{3-8}$ cycloalkyl which is unsubstituted or substituted with $R^5$, (5) phenyl, which is unsubstituted or substituted with $R^5$, and (6) heterocycle, which is unsubstituted or substituted with $R^5$, or $R^6$ and $R^7$ taken together with the nitrogen atom to which they are attached form a 3 to 8 membered ring, where the ring may contain one to four heteroatom independently selected from nitrogen, oxygen, and sulfur; where the ring may be saturated or partially saturated or unsaturated; which is unsubstituted or substituted one or more substituents selected from $R^5$;
$R^8$ is selected from the definitions of $R^6$ and $R^7$;
$R^9$ is selected from the group consisting of:
(1) hydroxy, (2) halogen, (3) $C_{1-6}$ alkyl, (4) —$C_{3-8}$ cycloalkyl, (5) —O—$C_{1-6}$ alkyl, (6) —O(C=O)—$C_{1-6}$ alkyl, (7) —NH—$C_{1-6}$ alkyl, (8) phenyl, (9) heterocycle, (10) —$CO_2H$, and (11) —CN;
or a pharmaceutically acceptable salt thereof.

The present invention also provides compounds of formula (I-1) and salts thereof:

[Chem. 2]

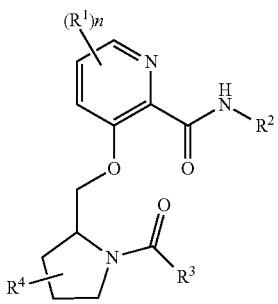

(I-1)

wherein:

R$^1$ is independently selected from the group consisting of:

(1) hydrogen, (2) halogen, (3) hydroxy, (4) —O$_p$—C$_{1-6}$ alkyl, where the alkyl is unsubstituted or substituted with one or more substituents selected from R$^5$, (5) —O$_p$—C$_{3-8}$ cycloalkyl, where the cycloalkyl is unsubstituted or substituted with one or more substituents selected from R$^5$, (6) C$_{2-4}$ alkenyl, where the alkenyl is unsubstituted or substituted with one or more substituents selected from R$^5$, (7) —(C=O)—NR$^6$R$^7$, (8) —NR$^6$R$^7$, (9) —S(O)$_2$—NR$^6$R$^7$, (10) —NR$^6$—S(O)$_2$R$^7$, (11) —S(O)$_r$—R$^8$, where r is 0, 1 or 2 and where R$^8$ is selected from the definitions of R$^6$ and R$^7$, (12) —CO$_2$H, and (13) —CN; where p is 0 or 1 (wherein if p is 0, a chemical bond is present in the place of O$_p$);

n is 1, 2, or 3; when n is two or more than two, R$^1$ may be same or different;

R$^2$ is selected from the group consisting of:

(1) hydrogen, (2) C$_{1-6}$ alkyl, which is unsubstituted or substituted with one or more substituents selected from R$^5$, (3) C$_{3-8}$ cycloalkyl which is unsubstituted or substituted with one or more substituents selected from R$^5$, (4) phenyl, which is unsubstituted or substituted with one or more substituents selected from R$^5$, and (5) heterocycle, which is unsubstituted or substituted with one or more substituents selected from R$^5$;

R$^3$ is selected from the group consisting of:

(1) —C$_{0-3}$ alkyl-O$_p$—C$_{0-3}$ alkyl-cycloalkyl which is unsubstituted or substituted with one or more substituents selected from R$^5$, (2) —C$_{0-3}$ alkyl-O$_p$—C$_{0-3}$ alkyl-phenyl, which is unsubstituted or substituted with one or more substituents selected from R$^5$, and (3) —C$_{0-3}$ alkyl-O$_p$—C$_{0-3}$ alkyl-heterocycle, which is unsubstituted or substituted with one or more substituents selected from R$^5$; where p is 0 or 1, (wherein if p is 0, a chemical bond is present in the place of O$_p$);

R$^4$ is selected from the group consisting of:

(1) hydrogen, and (2) hydroxy;

R$^5$ is selected from the group consisting of:

(1) halogen, (2) hydroxy, (3) —(C=O)$_q$—O$_r$—C$_{1-6}$ alkyl, where the alkyl is unsubstituted or substituted with one or more substituents selected from R$^9$, (4) —O$_p$—(C$_{1-3}$)perfluoroalkyl, (5) —(C=O)$_q$—O$_r$—C$_{3-8}$ cycloalkyl, where the cycloalkyl is unsubstituted or substituted with one or more substituents selected from R$^9$, (6) —(C=O)$_q$—O$_r$—C$_{2-4}$ alkenyl, where the alkenyl is unsubstituted or substituted with one or more substituents selected from R$^9$, (7) —(C=O)$_q$—O$_r$-phenyl or —(C=O)$_q$—O$_r$-napthyl, where the phenyl or napthyl is unsubstituted or substituted with one or more substituents selected from R$^9$, (8) —(C=O)$_q$—O$_r$-heterocycle, where the heterocycle is unsubstituted or substituted with one or more substituents selected from R$^9$, (9) —(C=O)—NR$^6$R$^7$, (10) —NR$^6$R$^7$, (11) —S(O)$_2$—NR$^6$R$^7$, (12) —S(O)$_t$—R$^8$, where t is 0, 1 or 2, (13) —CO$_2$H, (14) —CN, and (15) —NO$_2$; where p is 0 or 1, (wherein if p is 0, a chemical bond is present in the place of O$_p$) and where q is 0 or 1 and r is 0 or 1 (wherein if q is 0 or r is 0, a bond is present in the place of (C=O)$_q$ or O$_r$, and wherein if q is 0 and r is 0, a single bond is present in the place of (C=O)$_q$—O$_r$);

R$^6$ and R$^7$ are independently selected from the group consisting of:

(1) hydrogen, (2) C$_{1-6}$ alkyl, which is unsubstituted or substituted with R$^5$, (3) C$_{3-6}$ alkenyl, which is unsubstituted or substituted with R$^5$, (4) C$_{3-8}$ cycloalkyl which is unsubstituted or substituted with R$^5$, (5) phenyl, which is unsubstituted or substituted with R$^5$, and (6) heterocycle, which is unsubstituted or substituted with R$^5$, or R$^6$ and R$^7$ taken together with the nitrogen atom to which they are attached form a 3 to 8 membered ring, where the ring may contain one to four heteroatom independently selected from nitrogen, oxygen, and sulfur; where the ring may be saturated or partially saturated or unsaturated; which is unsubstituted or substituted one or more substituents selected from R$^5$;

R$^8$ is selected from the definitions of R$^6$ and R$^7$;

R$^9$ is selected from the group consisting of:

(1) hydroxy, (2) halogen, (3) C$_{1-6}$ alkyl, (4) —C$_{3-8}$ cycloalkyl, (5) —O—C$_{1-6}$ alkyl, (6) —O(C=O)—C$_{1-6}$ alkyl, (7) —NH—C$_{1-6}$ alkyl, (8) phenyl, (9) heterocycle, (10) —CO$_2$H, and (11) —CN;

or a pharmaceutically acceptable salt thereof.

Preferable compounds of this invention are in formula (I) and (I-1) wherein the definition described above:

R$^1$ is independently selected from the group consisting of:

(1) hydrogen, (2) halogen, (3) hydroxy, (4) —O$_p$—C$_{1-6}$ alkyl, where the alkyl is unsubstituted or substituted with one or more substituents selected from R$^5$, and (5) —O$_p$—C$_{3-8}$ cycloalkyl, where the cycloalkyl is unsubstituted or substituted with one or more substituents selected from R$^5$; where p is 0 or 1 (wherein if p is 0, a chemical bond is present in the place of O$_p$);

n is 1, 2, or 3; when n is two or more than two, R$^1$ may be same or different;

R$^3$ is 3 to 8 membered ring where the ring may contain one to four heteroatom independently selected from nitrogen, oxygen, and sulfur; where the ring may be saturated or unsaturated; and where the ring is optionally substituted with 1 to 4 substituents independently selected from the group consisting of:

(1) hydroxy, (2) halogen, (3) C$_{1-6}$ alkyl, which is unsubstituted or substituted with one or more substituents selected from R$^5$, (4) C$_{3-8}$ cycloalkyl, which is unsubstituted or substituted with one or more substituents selected from R$^5$, (5) —O—C$_{1-6}$ alkyl, which is unsubstituted or substituted with one or more substituents selected from R$^5$, and (6) —O—C$_{3-8}$ cycloalkyl, which is unsubstituted or substituted with one or more substituents selected from R$^5$;

R$^5$ is selected from the group consisting of:

(1) halogen, (2) hydroxy, (3) —(C=O)$_q$—O$_r$—C$_{1-6}$ alkyl, where the alkyl is unsubstituted or substituted with one or more substituents selected from R$^9$, (4) —O$_p$—(C$_{1-3}$) perfluoroalkyl, (5) —(C=O)$_q$—O$_r$—C$_{3-8}$ cycloalkyl, where the cycloalkyl is unsubstituted or substituted with one or more substituents selected from R$^9$, (6) —(C=O)$_q$—O$_r$-phenyl, where the phenyl is unsubstituted or substituted with one or more substituents selected from R$^9$, (7) —(C=O)$_q$—O$_r$-heterocycle, where the heterocycle is unsubstituted or substituted with one or more substituents selected from R$^9$, (8) —(C=O)—NR$^6$R$^7$, (9) —NR$^6$R$^7$, (10) —S(O)$_2$—NR$^6$R$^7$, and (11) —S(O)$_t$—R$^8$, where t is 0, 1 or 2; where p is 0 or 1, (wherein if p is 0, a chemical bond is present in the place of $O_p$) and where q is 0 or 1 and r is 0 or 1 (wherein if q is 0 or r is 0, a bond is present in the place of $(C=O)_q$ or $O_r$, and wherein if q is 0 and r is 0, a single bond is present in the place of $(C=O)_q—O_r$);

$R^9$ is selected from the group consisting of:

(1) hydroxy, (2) halogen, (3) $C_{1-6}$ alkyl, (4) —$C_{3-8}$ cycloalkyl, (5) —O—$C_{1-6}$ alkyl, (6) —O(C=O)—$C_{1-6}$ alkyl, (7) —NH—$C_{1-6}$ alkyl, (8) phenyl, and (9) heterocycle;

or a pharmaceutically acceptable salt thereof.

The more preferable compounds are selected from:

3-(((S)-1-(cis-4-(trifluoromethyl)cyclohexanecarbonyl)pyrrolidin-2-yl)methoxy)picolinamide, (R)-3-((1-(4-(trifluoromethoxy)benzoyl)pyrrolidin-2-yl)methoxy)picolinamide, (R)-3-((1-(4-(trifluoromethyl)benzoyl)pyrrolidin-2-yl)methoxy)picolinamide, (R)-3-((1-(3-chloro-2-fluorobenzoyl)pyrrolidin-2-yl)methoxy)picolinamide, (R)-3-((1-(2-(4-(trifluoromethyl)phenyl)acetyl)pyrrolidin-2-yl)methoxy)picolinamide, (R)-3-((1-(2-(4-(trifluoromethyl)phenyl)acetyl)pyrrolidin-2-yl)methoxy)picolinamide, (R)-3-((1-(6-tert-butylnicotinoyl)pyrrolidin-2-yl)methoxy)picolinamide, (R)-3-((1-(5-tert-butylisoxazole-3-carbonyl)pyrrolidin-2-yl)methoxy)picolinamide, (R)-3-((1-(5-tert-butylisoxazole-3-carbonyl)pyrrolidin-2-yl)methoxy)picolinamide, (R)-3-((1-(2-(4-(trifluoromethyl)phenoxy)acetyl)pyrrolidin-2-yl)methoxy)picolinamide, (R)-3-((1-(4-(2,2,2-trifluoroethoxy)benzoyl)pyrrolidin-2-yl)methoxy)picolinamide, 5-chloro-3-(((R)-1-(cis-4-(trifluoromethyl)cyclohexanecarbonyl)pyrrolidin-2-yl)methoxy)picolinamide, 5-chloro-3-(((R)-1-(trans-4-(trifluoromethyl)cyclohexanecarbonyl)pyrrolidin-2-yl)methoxy)picolinamide, 5-methoxy-3-(((R)-1-(trans-4-(trifluoromethyl)cyclohexanecarbonyl)pyrrolidin-2-yl)methoxy)picolinamide, 5-(trifluoromethyl)-3-(((R)-1-(trans-4-(trifluoromethyl)cyclohexanecarbonyl)pyrrolidin-2-yl)methoxy)picolinamide, N-(2-hydroxyethyl)-3-(((R)-1-(trans-4-(trifluoromethyl)cyclohexanecarbonyl)pyrrolidin-2-yl)methoxy)picolinamide, (R)—N-(2-methoxyethyl)-3-((1-(3-(trifluoromethyl)benzoyl)pyrrolidin-2-yl)methoxy)picolinamide, (R)—N-((1-hydroxycyclohexyl)methyl)-3-((1-(3-(trifluoromethyl)benzoyl)pyrrolidin-2-yl)methoxy)picolinamide, Methyl 2-(3-(((R)-1-(trans-4-(trifluoromethyl)cyclohexanecarbonyl)pyrrolidin-2-yl)methoxy)picolinamido)acetate, N-(2-methoxyethyl)-3-(((R)-1-(trans-4-(trifluoromethyl)cyclohexanecarbonyl)pyrrolidin-2-yl)methoxy)picolinamide, N-((1-hydroxycyclohexyl)methyl)-3-(((R)-1-(trans-4-(trifluoromethyl)cyclohexanecarbonyl)pyrrolidin-2-yl)methoxy)picolinamide, N-(pyridin-2-ylmethyl)-3-(((R)-1-(trans-4-(trifluoromethyl)cyclohexanecarbonyl)pyrrolidin-2-yl)methoxy)picolinamide, N-benzyl-3-(((R)-1-(trans-4-(trifluoromethyl)cyclohexanecarbonyl)pyrrolidin-2-yl)methoxy)picolinamide, N-phenyl-3-(((R)-1-(trans-4-(trifluoromethyl)cyclohexanecarbonyl)pyrrolidin-2-yl)methoxy)picolinamide, N-(pyridin-2-yl)-3-(((R)-1-(trans-4-(trifluoromethyl)cyclohexanecarbonyl)pyrrolidin-2-yl)methoxy)picolinamide, N-(4H-1,2,4-triazol-3-yl)-3-(((R)-1-(trans-4-(trifluoromethyl)cyclohexanecarbonyl)pyrrolidin-2-yl)methoxy)picolinamide, N—((R)-2-hydroxy-1-phenylethyl)-3-(((R)-1-(trans-4-(trifluoromethyl)cyclohexanecarbonyl)pyrrolidin-2-yl)methoxy)picolinamide, N-(oxazol-2-yl)-3-(((R)-1-(trans-4-(trifluoromethyl)cyclohexanecarbonyl)pyrrolidin-2-yl)methoxy)picolinamide, N-((tetrahydro-2H-pyran-4-yl)methyl)-3-(((R)-1-(trans-4-(trifluoromethyl)cyclohexanecarbonyl)pyrrolidin-2-yl)methoxy)picolinamide, N-(tetrahydro-2H-pyran-4-yl)-3-(((R)-1-(trans-4-(trifluoromethyl)cyclohexanecarbonyl)pyrrolidin-2-yl)methoxy)picolinamide, N-(5-methylisoxazol-3-yl)-3-(((R)-1-(trans-4-(trifluoromethyl)cyclohexanecarbonyl)pyrrolidin-2-yl)methoxy)picolinamide, N-(1,5-dimethyl-1H-pyrazol-3-yl)-3-(((R)-1-(trans-4-(trifluoromethyl)cyclohexanecarbonyl)pyrrolidin-2-yl)methoxy)picolinamide, N-(1-methyl-1H-pyrazol-3-yl)-3-(((R)-1-(trans-4-(trifluoromethyl)cyclohexanecarbonyl)pyrrolidin-2-yl)methoxy)picolinamide, N-(isoxazol-3-yl)-3-(((R)-1-(trans-4-(trifluoromethyl)cyclohexanecarbonyl)pyrrolidin-2-yl)methoxy)picolinamide, N-(oxazol-2-yl)-3-(((S)-1-(trans-4-(trifluoromethyl)cyclohexanecarbonyl)pyrrolidin-2-yl)methoxy)picolinamide, (R)-3-((1-(2-(4,4-difluorocyclohexyl)acetyl)pyrrolidin-2-yl)methoxy)-N-(isoxazol-3-yl)picolinamide, N-(pyrazin-2-yl)-3-(((R)-1-(trans-4-(trifluoromethyl)cyclohexanecarbonyl)pyrrolidin-2-yl)methoxy)picolinamide, N-(isoxazol-5-yl)-3-(((R)-1-(trans-4-(trifluoromethyl)cyclohexanecarbonyl)pyrrolidin-2-yl)methoxy)picolinamide, (R)—N-(pyridin-2-ylmethyl)-3-((1-(3-(trifluoromethyl)benzoyl)pyrrolidin-2-yl)methoxy)picolinamide, (R)—N-benzyl-3-((1-(3-(trifluoromethyl)benzoyl)pyrrolidin-2-yl)methoxy)picolinamide (R)—N-(pyridin-2-yl)-3-((1-(3-(trifluoromethyl)benzoyl)pyrrolidin-2-yl)methoxy)picolinamide, 3-(((2R,4R)-4-hydroxy-1-(trans-4-(trifluoromethyl)cyclohexanecarbonyl)pyrrolidin-2-yl)methoxy)-N-(isoxazol-3-yl)picolinamide, 5-chloro-3-((3-methyl-1-(trans-4-(trifluoromethyl)cyclohexanecarbonyl)pyrrolidin-3-yl)methoxy)picolinamide, 5-chloro-3-((3-(trans-4-(trifluoromethyl)cyclohexanecarbonyl)-3-azabicyclo[3.1.0]hexan-1-yl)methoxy)picolinamide, 3-((3-methyl-1-(trans-4-(trifluoromethyl)cyclohexanecarbonyl)pyrrolidin-3-yl)methoxy)-N-((tetrahydro-2H-pyran-4-yl)methyl)picolinamide, N-((tetrahydro-2H-pyran-4-yl)methyl)-3-((3-(trans-4-(trifluoromethyl)cyclohexanecarbonyl)-3-azabicyclo[3.1.0]hexan-1-yl)methoxy)picolinamide, N-(tetrahydro-2H-pyran-4-yl)-3-((3-(trans-4-(trifluoromethyl)cyclohexanecarbonyl)-3-azabicyclo[3.1.0]hexan-1-yl)methoxy)picolinamide, N-((tetrahydro-2H-pyran-4-yl)methyl)-3-((1-(trans-4-(trifluoromethyl)cyclohexanecarbonyl)pyrrolidin-3-yl)methoxy)picolinamide and N-((tetrahydro-2H-pyran-4-yl)methyl)-3-((1-(trans-4-(trifluoromethyl)cyclohexanecarbonyl)pyrrolidin-3-yl)methoxy)picolinamide.

Also, the present invention provides the use of a compound of formula (I) or a pharmaceutically acceptable salt thereof, each as described herein, for the manufacture of a medicament for the treatment of a condition or disorder mediated by TTX-S channel; in particular, $Na_{V1.3}$ channels blocking activity. In order to use the compounds of formula (I) and pharmaceutically acceptable salts thereof in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

Preferably, the present invention also provides the use of a compound of formula (I) or a pharmaceutically acceptable salt thereof, each as described herein, for the manufacture of a medicament for the treatment of diseases selected from TTX-S channels related diseases.

Also, the present invention provides a pharmaceutical composition comprising a compound of formula (I) or a pharmaceutically acceptable salt thereof, each as described herein, together with a pharmaceutically acceptable carrier for said compound.

Also, the present invention provides a pharmaceutical composition comprising a compound of formula (I) or a pharmaceutically acceptable salt thereof, each as described herein, together with a pharmaceutically acceptable carrier for said compound and another pharmacologically active agent.

Also, the present invention provides a process for preparing a pharmaceutical composition, the process comprising mixing a compound of formula (I) or a pharmaceutically acceptable salt thereof and a pharmaceutically acceptable carrier or excipient.

Also, the present invention provides an intermediate in a process for preparing a compound of formula (I) or a pharmaceutically acceptable salt thereof.

Further, the present invention provides a method of treatment of a condition or disorder mediated by TTX-S channels blocking activity, in a mammalian subject, which comprises administering to a mammal in need of such treatment a therapeutically effective amount of a compound of formula (I) or a pharmaceutically acceptable salt thereof, each as described herein.

In a further aspect, the present invention provides a process for preparing a pharmaceutical composition, the process comprising mixing a compound of formula (I) or a pharmaceutically acceptable salt thereof and a pharmaceutically acceptable carrier or excipient.

Advantageous Effects of Invention

Examples of conditions or disorders mediated by TTX-S channels blocking activity include, but are not limited to, TTX-S channels related diseases. The compounds of the present invention show the TTX-S channels blocking activity. The compounds of the present invention may show less toxicity, good absorption, distribution, good solubility, less protein binding affinity other than TTX-S channels, less drug-drug interaction, and good metabolic stability.

DESCRIPTION OF EMBODIMENTS

As appreciated by those of skill in the art, "halogen" or "halo" as used herein are intended to include fluoro, chloro, bromo and iodo. Similarly, $C_{1-6}$, as in $C_{1-6}$ alkyl is defined to identify the group as having 1, 2, 3, 4, 5 or 6 carbons in a linear or branched arrangement, such that $C_{1-6}$ alkyl specifically includes methyl, ethyl, n-propyl, isopropyl, n-butyl, iso-butyl, tert-butyl, pentyl, and hexyl. Similarly, $C_{2-6}$ alkenyl is defined to identify the group as having 2, 3, 4, 5 or 6 carbons which incorporates at least one double bond, which may be in a E- or a Z-arrangement. A group which is designated as being independently substituted with substituents may be independently substituted with multiple numbers of such substituents.

The term "alkenyl", as used herein, means a hydrocarbon radical having at least one double bond including, but not limited to, ethenyl, propenyl, 1-butenyl, 2-butenyl and the like.

The term "cycloalkyl", as used herein, means a mono- or bicyclic ring, but not limited to, cyclopropyl, cyclobutyl, cyclopentyl, cyclohexyl, cycloheptyl, norboranyl, and adamantyl groups and the like.

The term "heterocycle" as used herein includes both unsaturated and saturated heterocyclic moieties, wherein the unsaturated heterocyclic moieties include benzoimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazolinyl, isoxazolinyl, oxetanyl, pyrazinyl, pyrazolyl, pyridazinyl, pyridopyridinyl, pyridazinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof and S-oxides thereof.

The term "$C_0$", as used herein, means direct bond.

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition.

As used herein, the article "a" or "an" refers to both the singular and plural form of the object to which it refers unless indicated otherwise.

Included within the scope of the "compounds of the invention" are all salts, solvates, hydrates, complexes, polymorphs, prodrugs, radiolabeled derivatives, stereoisomers and optical isomers of the compounds of formula (I).

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. ScL, 1977, 66, 1-19, such as acid addition salts formed with inorganic acids e.g. hydrochloric, hydrobromic, sulfuric, nitric or phosphoric acid; and organic acids e.g. succinic, maleic, formic, acetic, trifluoroacetic, propionic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms. In addition, certain compounds containing an acidic function such as a carboxy can be isolated in the form of their inorganic salt in which the counter ion can be selected from sodium, potassium, lithium, calcium, magnesium and the like, as well as from organic bases.

The compounds of formula (I) and salts thereof may be prepared in crystalline or non-crystalline form, and, if crystalline, may optionally be hydrated or solvated. This invention includes within its scope stoichiometric hydrates or solvates as well as compounds containing variable amounts of water and/or solvent.

Salts and solvates having non-pharmaceutically acceptable counter-ions or associated solvents are within the scope of the present invention, for example, for use as intermediates in the preparation of other compounds of formula (I) and their pharmaceutically acceptable salts.

The compounds of formula (I) may have polymorphs in crystalline form, which are within the scope of the present invention.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In certain of the compounds of formula (I), there may be some chiral carbon atoms. In such cases, compounds of formula (I) exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$. Compounds of the invention that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances, isotopically labeled compounds of the invention can generally be prepared by carrying out the procedures disclosed in the Schemes and/or in the Examples below, then substituting a readily available isotopically labeled reagent for a non-isotopically labeled reagent.

With respect to other compounds disclosed in the art, the present compounds exhibit unexpected properties, such as with respect to duration of action and/or metabolism, such as increased metabolic stability, enhanced oral bioavailability or absorption, and/or decreased drug-drug interactions.

The compounds of formula (I), being $Na_{V1.3}$ channel blockers, are potentially useful in the treatment of a range of disorders. The treatment of pain, particularly chronic, inflammatory, neuropathic, nociceptive and visceral pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually in twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and
orofacial pain, including dental pain, otic pain, burning mouth syndrome and temporomandibular myofascial pain.

The picolinamide derivatives of formula (I) are also expected to be useful in the treatment of multiple sclerosis.

The invention also relates to therapeutic use of the picolinamide derivatives of formula (I) as agents for treating or relieving the symptoms of neurodegenerative disorders. Such neurodegenerative disorders include, for example, Alzheimer's disease, Huntington's disease, Parkinson's disease, and Amyotrophic Lateral Sclerosis. The present invention also covers treating neurodegenerative disorders termed acute brain injury. These include but are not limited to: stroke, head trauma, and asphyxia. Stroke refers to a cerebral vascular disease and may also be referred to as a cerebral vascular accident (CVA) and includes acute thromboembolic stroke. Stroke includes both focal and global ischemia. Also, included are transient cerebral ischemic attacks and other cerebral vascular problems accompanied by cerebral ischemia. These vascular disorders may occur in a patient undergoing carotid endarterectomy specifically or other cerebrovascular or vascular surgical procedures in general, or diagnostic vascular procedures including cerebral angiography and the like. Other incidents are head trauma, spinal cord trauma, or injury from general anoxia, hypoxia, hypoglycemia, hypotension as well as similar injuries seen during procedures from embole, hyperfusion, and hypoxia. The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

TTX-S sodium channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with TTX-S sodium channels, including one or more of the following conditions or diseases: pain, acute pain, chronic pain, neuropathic pain, inflammatory pain, visceral pain, nociceptive pain, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy.

The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize.

For administration to human patients, the total daily dose of the compounds of the invention is typically in the range 0.1 mg to 1000 mg depending, of course, on the mode of administration. For example, oral administration may require a total daily dose of from 1 mg to 1000 mg, while an intravenous dose may only require from 0.1 mg to 100 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

For the avoidance of doubt, references herein to "treatment" include references to curative, palliative and prophylactic treatment.

In one embodiment, the dosage range will be about 0.5 mg to 500 mg per patient per day; in another embodiment about 0.5 mg to 200 mg per patient per day; in another embodiment about 1 mg to 100 mg per patient per day; and in another embodiment about 5 mg to 50 mg per patient per day; in yet another embodiment about 1 mg to 30 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is envisioned. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, including about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

A TTX-S sodium channels blocker may be usefully combined with another pharmacologically active compound, or with two or more other pharmacologically active compounds, particularly in the treatment of inflammatory, pain and urological diseases or disorders. For example, a TTX-S sodium channels blocker, particularly a compound of formula (I), or a pharmaceutically acceptable salt or solvate thereof, as defined above, may be administered simultaneously, sequentially or separately in combination with one or more agents selected from:

- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
- a barbiturate sedative, e.g. amobarbital, aprobarbital, butabarbital, butabital, mephobarbital, metharbital, methohexital, pentobarbital, phenobartital, secobarbital, talbutal, theamylal or thiopental;
- a benzodiazepine having a sedative action, e.g. chlordiazepoxide, clorazepate, diazepam, flurazepam, lorazepam, oxazepam, temazepam or triazolam;
- an H1 antagonist having a sedative action, e.g. diphenhydramine, pyrilamine, promethazine, chlorpheniramine or chlorcyclizine;
- a sedative such as glutethimide, meprobamate, methaqualone or dichloralphenazone;
- a skeletal muscle relaxant, e.g. baclofen, carisoprodol, chlorzoxazone, cyclobenzaprine, methocarbamol or orphrenadine;
- an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex(registered trademark), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;
- an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;
- a tricyclic antidepressant, e.g. desipramine, imipramine, amitriptyline or nortriptyline;
- an anticonvulsant, e.g. carbamazepine, lamotrigine, topiratmate or valproate;
- a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);
- a muscarinic antagonist, e.g oxybutynin, tolterodine, propiverine, tropsium chloride, darifenacin, solifenacin, temiverine and ipratropium;
- a COX-2 selective inhibitor, e.g. celecoxib, rofecoxib, parecoxib, valdecoxib, deracoxib, etoricoxib, or lumiracoxib;
- a coal-tar analgesic, in particular paracetamol;
- a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion(registered trademark) or sarizotan;
- a vanilloid receptor agonist (e.g. resinferatoxin) or antagonist (e.g. capsazepine);
- a beta-adrenergic such as propranolol;
- a local anaesthetic such as mexiletine;
- a corticosteroid such as dexamethasone;
- a 5-HT receptor agonist or antagonist, particularly a 5-HT1B/1D agonist such as eletriptan, sumatriptan, naratriptan, zolmitriptan or rizatriptan;
- a 5-HT2A receptor antagonist such as R(+)-alpha-(2,3-dimethoxy-phenyl)-1-[2-(4-fluorophenylethyl)]-4-piperidinemethanol (MDL-100907);
- a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;
- Tramadol(registered trademark);
- a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-

(3,4-methylenedioxyphenyl)-pyrazino[2',1':6,1]-pyrido [3,4-b]indole-1,4-dione (TC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4] triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d] pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1alpha,3alpha,5alpha)(3-aminomethyl-bicyclo[3.2.0]hept-3-yl)-acetic acid, (3S,5R)-3-aminomethyl-5 methyl-heptanoic acid, (3S,5R)-3 amino-5 methyl-heptanoic acid, (3S,5R)-3 amino-5 methyl-octanoic acid, (2S,4S)-4-(3-chlorophenoxy) proline, (2S,4S)-4-(3-fluorobenzyl)-proline, [(1R,5R, 6S)-6-(aminomethyl)bicyclo[3.2.0]hept-6-yl]acetic acid, 3-(1-aminomethyl-cyclohexylmethyl)-4H-[1,2,4] oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3 aminomethyl-5 methyl-octanoic acid, (3S,5R)-3 amino-5 methyl-nonanoic acid, (3S,5R)-3 amino-5 methyl-octanoic acid, (3R,4R,5R)-3-amino-4,5-dimethyl-heptanoic acid and (3R,4R,5R)-3-amino-4,5-dimethyl-octanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericl amine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan(registered trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl] thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3, 5-trimethyl-6-(3-pyridylmethyl),1,4-benzoquinone (CV-6504);

a sodium channel blocker, such as lidocaine;

a 5-HT3 antagonist, such as ondansetron;

and the pharmaceutically acceptable salts and solvates thereof.

Such combinations offer significant advantages, including synergistic activity, in therapy.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrate compositions are generally preferred. Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound or pharmaceutically acceptable salt thereof.

For parenteral administration, fluid unit dosage forms are prepared utilising a compound of formula (I) or pharmaceutically acceptable salt thereof and a sterile vehicle. Formulations for injection may be presented in unit dosage form e.g. in ampoules or in multi-dose, utilising a compound of formula (I) or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of formula (I) or pharmaceutically acceptable salts thereof may also be formulated in rectal compositions such as suppositories or retention enemas, e.g. containing conventional suppository bases such as cocoa butter or other glycerides.

The compounds of formula (I) or pharmaceutically acceptable salts may also be formulated as depot preparations. Such long acting formulations may be administered by implantation (for example subcutaneously or intramuscularly) or by intramuscular injection. Thus, for example, the compounds of formula (I) or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds formula (I) or pharmaceutically acceptable salts thereof may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, topical (including ophthalmic and nasal), depot or rectal administration or in a form suitable for administration by inhalation or insufflation (either through the mouth or nose). The compounds of formula (I) and pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

General Synthesis

Throughout the instant application, the following abbreviations are used with the following meanings:

DMF: N,N-dimethylformamide

TLC: Thin layer chromatography

HBTU: N,N,N',N'-tetramethyl-O-(1H-benzotriazol-1-yl)uronium hexafluorophosphate

DTAD: di-tert-butyl azodicarboxylate mCPBA: m-chloroperbenzoic

TMSCN: trimethylsilyl cyanide

WSC: 1-ethyl-3-(3-dimethylaminopropyl)carbodiimide hydrochloride

HOBT: 1-hydroxybenzotriazole hydrate

DMSO: dimethylsulfoxide

XANTPHOS: 4,5-Bis(diphenylphosphino)-9,9-dimethylxanthene $Pd_2(dba)_3$: Tris(dibenzylideneacetone)dipalladium The term of "base" is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, triethylamine, diisopropylethylamine, DBU, DBN, DABCO, pyridine, lutidine, colidine, sodium carbonate, sodium hydrogencarbonate, sodium hydroxide, potassium carbonate, potassium hydrogencarbonate, potassium hydroxide, barium hydroxide, and cesium carbonate are preferred.

The reactions are normally and preferably effected in the presence of inert solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as dichloromethane, chloroform, carbon tetrachloride, and dichloroethane; ethers, such as diethyl ether, diisopropyl ether, tetrahydrofuran (THF), and dioxane; aromatic hydrocarbons, such as benzene, toluene and nitrobenzene; amides, such as, DMF, N,N-dimethylacetamide, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N- diethylaniline; alcohols, such as methanol, ethanol, propanol, isopropanol, and butanol; nitriles, such as acetonitrile and benzonitrile; sulfoxides, such as DMSO and sulfolane; ketones, such as acetone and diethylketone. Of these solvents, including but not limited to DMF, DMSO, THF, diethylether, diisopropylether, dimethoxyethane, acetonitrile, dichloromethane, dichloroethane and chloroform are preferred.

The term "protecting group", as used hereinafter, means a hydroxy, carboxy, or amino-protecting group which is selected from typical hydroxy, carboxy, or amino-protecting groups described in Protective Groups in Organic Synthesis edited by T. W. Greene et al. (John Wiley & Sons, 1999). All starting materials in the following general syntheses may be commercially available or obtained by conventional methods known to those skilled in the art, such as European Journal of Medicinal Chemistry, 12 (1), 87-91; 1977 and the disclosures of which are incorporated herein by reference.

All of the picolinamide derivatives of the formula (I) can be prepared by the procedures described in the general methods presented below or by the specific methods described in the Examples section and the Preparations section, or by routine modifications thereof. The present invention also encompasses any one or more of these processes for preparing the picolinamide derivatives of formula (I), in addition to any novel intermediates used therein.

[Chem. 3]

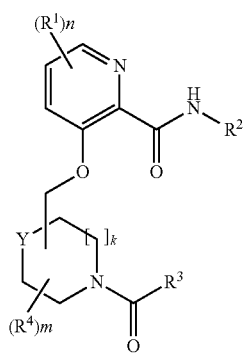

(I)

In the following general methods, Y, $R^1$, $R^2$, $R^3$, and $R^4$ are as previously defined for picolinamide derivatives of the formula (I) unless otherwise stated.

The preparation of compounds of formula (I) of the present invention can be carried out in sequential or convergent synthetic routes.

Syntheses detailing the preparation of the compounds of formula (I) in a sequential manner are presented in the following reaction schemes. The phrase "standard peptide coupling reaction conditions" is used repeatedly here, and it means coupling a carboxylic acid with an amine using an acid activating agent such as EDC, DCC, HBTU, and BOP in a inert solvent such as DMF, acetonitrile, and dichloromethane in the presence of a catalyst such as HOBT and/or in the presence of a base such as triethylamine, diisopropylethylamine.

The following illustrates a preparation of the desired compound of formula 1 (Scheme 1).

Scheme 1

[Chem. 4]

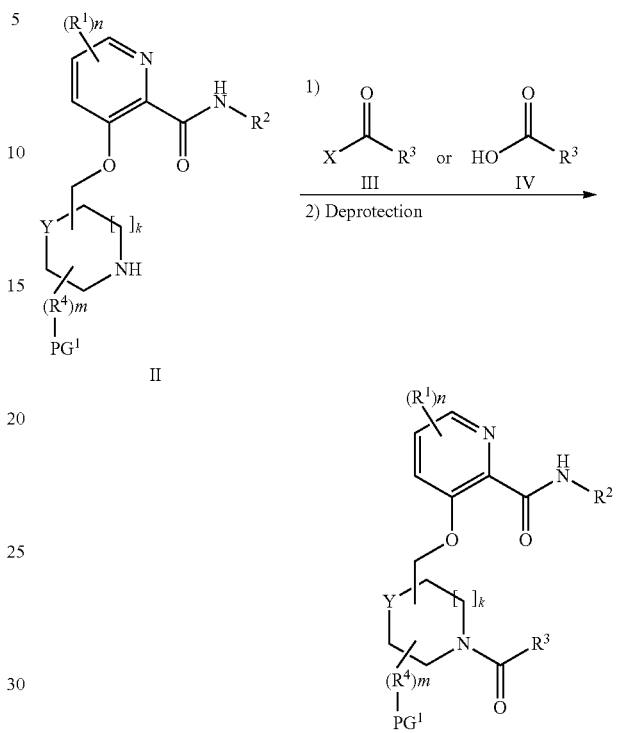

In Scheme 1, $PG^1$ is a hydroxy-protecting group or absent and X is a leaving group commonly used for peptide coupling reaction and Y, $R^1$, $R^2$, $R^3$ and $R^4$ are as defined above.

The term "hydroxy-protecting group", as used herein, signifies a protecting group capable of being cleaved by chemical means, such as (hydrogenolysis, hydrolysis, electrolysis, or photolysis and such as hydroxy-protecting groups are described in Protective Groups in Organic Synthesis edited by T. W. Greene et al. (John Wiley & Sons, 1999). Typical hydroxy-protecting groups include, but not limited to: methyl, $CH_3OCH_2$—, $CH_3SCH_2$—, benzyl, p-methoxybenzyl, benxyloxylmethyl, benzoyl, acetyl, trimethylsilyl, triethylsilyl, t-butyldimethylsilyl, and t-butyldiphenylsilyl. Of these groups, t-butyldimethylsilyl and bezyloxymethyl are preferred.

The term "a leaving group of the commonly used for peptide coupling reaction" as used herein, signifies, such as but no limited to:
halide, acid anhydride, imidazole, and azide.

When $R^4$ is hydroxy group and $PG^1$ is hydroxy-protecting group, the compound of formula I can be prepared from a compound of formula II by coupled with an activated ester compound of formula III and following deprotection of $PG^1$. The coupling reaction is carried out with presence of the suitable base such as triethylamine in a suitable solvent such as dichloromethane at a temperature of from about −10 to about 70° C. for about 5-20 hours. This deprotection reaction method is described in detail by T. W. Greene et al. [Protective Groups in Organic Synthesis, (1999)], the disclosures of which are incorporated herein by reference. The following is a typical method, provided the protecting groups are t-butyldimethylsilyl and benzyloxymethyl.

The deprotection reaction is carried out in the presence of an acid. There is likewise no particular restriction on the nature of the acids used, and any acid commonly used in reactions of this type may equally be used here. Examples of such acids include, but are not limited to: acids, such as trifluoroacetic acid and trifluoromethanesulfonic acid, or hydrogen halide such as HCl, HBr, and HI.

The deprotection reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride, and dichloroethane; ethers, such as diethyl ether, diisopropyl ether, THF, and dioxane, esters such as ethyl acetate, alcohols such as methanol, ethanol, propanol, isopropanol, and butanol, water and aromatic hydrocarbons, such as benzene, toluene, and nitrobenzene. Of these solvents, dichloromethane, dichloroethane, chloroform, water, alcohol, THF, and ethyl acetate are preferred.

When $R^4$ is not hydroxy group and $PG^1$ is absent, the compound of formula I can be prepared from a compound of formula II by coupling with an activated ester compound of formula III as defined above.

When $R^4$ is hydroxy group and $PG^1$ is hydroxy-protecting group, the compound of formula I can be also prepared by peptide coupling reaction and following $PG^1$ deprotection reaction. In the case of $PG^1$ is absent, the compound of formula I can be prepared by the same method as described above without $PG^1$ deprotection reaction. The coupling reaction of the compound of formula II and IV can be carried out by using standard peptide coupling reaction conditions as defined above. The method of following $PG^1$ deprotection reaction is described in above.

When $R^4$ is not hydroxy group and $PG^1$ is absent, the compound of formula I can be prepared from a compound of formula II and IV by utilizing standard peptide coupling reaction conditions as defined above.

The following illustrates an alternative preparation of the desired compound of formula I (Scheme 2).

Scheme 2

[Chem. 5]

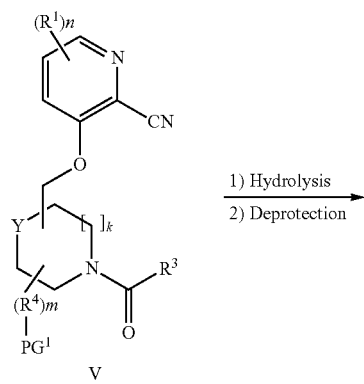

1) Hydrolysis
2) Deprotection

-continued

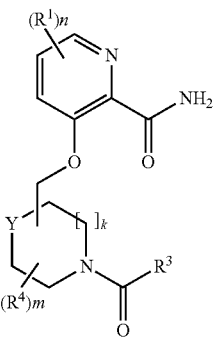

Ia: $R^2$ is hydrogen

In Scheme 2, Y, $PG^1$, $R^1$, $R^2$, $R^3$ and $R^4$ are as defined above.

When $R^4$ is hydroxy group and $PG^1$ is hydroxy-protecting group, the compound of formula I can be prepared from the compound of formula V by partially hydrolysis of nitrile and following or same time $PG^1$ deprotection reaction. In the case of $PG^1$ is absent, the compound of formula I can be prepared by the same method as described above without $PG^1$ deprotection reaction.

When $R^4$ is not hydroxy group and $PG^1$ is absent, the compound of formula I can be prepared from the compound of formula V by partially hydrolysis of nitrile.

The partially hydrolysis of nitrile and or $PG^1$ deprotection reaction is carried out in the presence of base. There is likewise no particular restriction on the nature of the bases used, and any base commonly used in reactions of this type may equally be used here. Examples of such base include, but are not limited to: metal hydroxide, such as sodium hydroxide and potassium hydroxide: metal carbonate with hydrogen peroxide, such as potassium carbonate with hydrogen peroxide.

This reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but not limited to: alcohols, such as methanol, ethanol, propanol, isopropanol, and t-butanol; nitriles, such as acetonitrile and benzonitrile; sulfoxides, such as dimethyl sulfoxide and sulfolane. Of these solvents, t-butanol, acetonitrile, and dimethyl sulfoxide are preferred.

This reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −10° C. to about 85° C., more preferably from about 0° C. to about 70° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 48 hours.

The partially hydrolysis of nitrile and/or $PG^1$ deprotection reaction is also carried out in the presence of acid. There is likewise no particular restriction on the nature of the acids used, and any acids commonly used in reactions of this type may equally be used here. Examples of such acid include, but are not limited to: inorganic acid, such as hydrochloric acid, sulfuric acid, and polyphosphoric acid: combination acid, such as sulfuric acid with acetic acid, boron trifluoride with aqueous acetic acid.

This reaction is normally and preferably effected in the absence of solvent.

This reaction can take place over a wide range of temperatures, and the precise reaction temperature is not critical to the invention. The preferred reaction temperature will depend upon such factors as the nature of the acids, and the starting materials. However, in general, it is convenient to carry out the reaction at a temperature of from about 20° C. to about 150° C., more preferably from about 40° C. to about 140° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 48 hours.

In the following $PG^1$ deprotection reaction is needed, the method of $PG^1$ deprotection reaction is described in above.

The following illustrates an alternative preparation of the desired compound of formula I (Scheme 3).

Scheme 3

[Chem. 6]

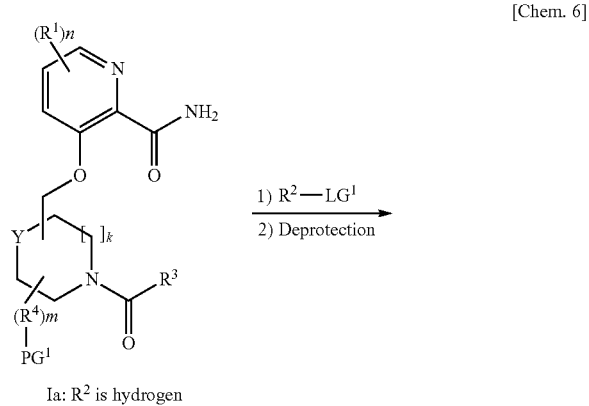

Ia: $R^2$ is hydrogen

Ib: $R^2$ is not hydrogen

In Scheme 3, $LG^1$ is leaving group, Y, $PG^1$, $R^1$, $R^2$, $R^3$ and $R^4$ are as defined above.

The term "leaving group", as used herein, signifies a group capable of being substituted by nucleophilic groups, such as a hydroxy group, amines, or carboanions and examples of such leaving groups include halogen atoms, an alkylsulfonyl group and an arylsulfonyl group. Of these, an iodine atom, a bromine atom, a chlorine atom, a trifluoromethanesulfonyl group, a p-toluenesulfonyl, and a phenysulfonyl are preferred.

When $R^4$ is hydroxy group and $PG^1$ is hydroxy-protecting group, the compound of formula Ib ($R^2$ is not hydrogen atom) can be prepared from the compound of formula Ia ($R^2$ is hydrogen atom) with $R^2$-$LG^1$ by palladium catalyzed coupling reaction or nucleophilic substitution reaction and following $PG^1$ deprotection reaction. In the case of $PG^1$ is absent, the compound formula Ib ($R^2$ is not hydrogen atom) can be prepared by the same method as described above without $PG^1$ deprotection reaction.

When $R^4$ is not hydroxy group and $PG^1$ is absent, the compound of formula Ib can be prepared from the compound of formula Ia by the same method as described above without $PG^1$ deprotection reaction.

This palladimun catalyzed coupling reaction method is described in detail by Ligthart, G. B. et al. Journal of Organic Chemistry, 375, 71, 2006, the disclosures of which are incorporated herein by reference.

This nucleophilic substitution reaction is carried out in the presence of suitable base. There is likewise no particular restriction on the nature of the bases used, and any base commonly used in reactions of this type may equally be used here. Examples of such base include, but are not limited to: metal hydride, such as sodium hydride and potassium hydride: metal amide, such as lithium N,N-diisopropylamide.

This reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as dichloromethane, chloroform, carbon tetrachloride, and dichloroethane; ethers, such as diethyl ether, diisopropyl ether, THF, dimethoxyethane, and dioxane; aromatic hydrocarbons, such as benzene, toluene, xylene, chlorobenzene, dichlorobenzene, and nitrobenzene; amides, such as formamide, N,N-dimethylformamide, N,N-dimethylacetamide, and hexamethylphosphoric triamide; nitriles, such as acetonitrile and benzonitrile; sulfoxides, such as dimethyl sulfoxide, and sulfolane. Of these solvents, THF, dimethoxyethane, acetonitrile, dimethyl sulfoxide are preferred.

This reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about $-10°$ C. to about 150° C., more preferably from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 100 hours.

The following illustrates an alternative preparation of the desired compound of formula I (Scheme 4).

Scheme 4

[Chem. 7]

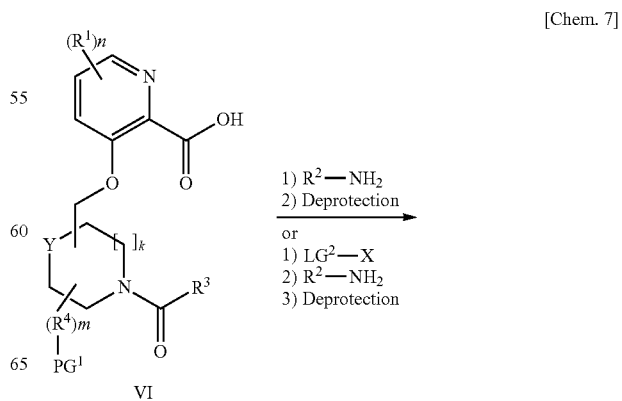

VI

-continued

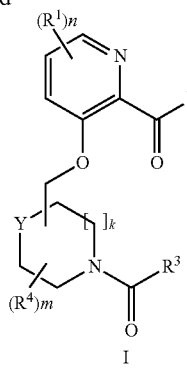

I

In Scheme 4, X, Y, $PG^1$, $R^1$, $R^2$, $R^3$ and $R^4$ are as defined above and $LG^2$ is a leaving group using for the formation of activated ester, such as but not limited to: halo oxalyl group of oxalyl halide, halo thiony group of thionyl halide, halide of halo alkylformate, N-imidazoylcarbony group of N,N'-carbonydiimidazole, and diphenylphosphoryl group of diphenylphosphoryl azide.

The compound of formula VI is prepared by deprotection reaction from compound of formula XIVc wherein $PG^3$ is a carboxy-protecting group.

When $R^4$ is hydroxy group and $PG^1$ is hydroxy-protecting group, the compound of formula I can be prepared by peptide coupling reaction and following $PG^1$ deprotection reaction. The coupling reaction of the compound of formula VI and an amine compound of $R^2$—$NH_2$ can be carried out by using standard peptide coupling reaction conditions and the method of $PG^1$ deprotection reaction were described in above. In the case of $PG^1$ is absent, the compound of formula I can be prepared by the same method as described above without $PG^1$ deprotection reaction.

When $R^4$ is not hydroxy group and $PG^1$ is absent, the compound of formula I can be prepared from a compound of formula VI and an amine compound $R^2$—$NH_2$ by the same manner as defined above without $PG^1$ deprotection reaction.

The desired compound of formula of I can be prepared by the alternative routes.

When $R^4$ is hydroxy group and $PG^1$ is hydroxy-protecting group, the compound of formula I can be prepared by peptide coupling reaction via an activated ester, and following $PG^1$ deprotection reaction. The activated ester can be prepared from the compound of formula VI and $LG^2$-X with or without suitable base. The compound of formula I can be prepared from the activated ester and an amine compound of $R^2$—$NH_2$ with suitable base and following $PG^1$ deprotection reaction.

When $R^4$ is not hydroxy group and $PG^1$ is absent, the compound of formula I can be prepared from a compound of formula VI via an activated ester and an amine compound $R^2$—$NH_2$ by the same manner as defined above without $PG^1$ deprotection reaction.

The following illustrates a preparation of the intermediate of formula II via amino-protected compound of formula VIIb ($R^2$ is not hydrogen atom) (Scheme 5).

Scheme 5

[Chem. 8]

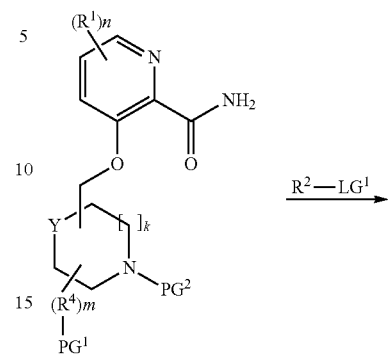

VIIa: $R^2$ is hydrogen

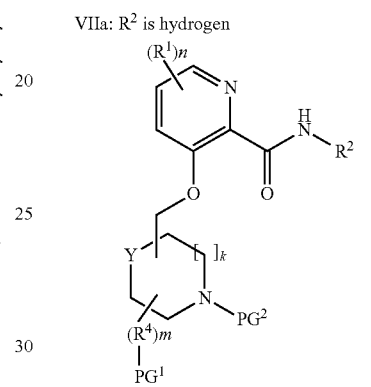

VIIb: $R^2$ is not hydrogen

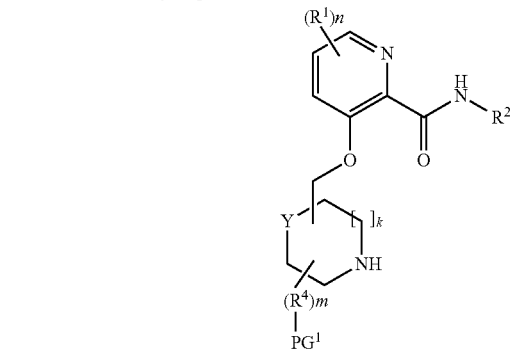

II

In Scheme 5, $PG^2$ is an amino-protecting group, $LG^1$, $PG^1$, Y, $R^1$, $R^2$, $R^3$ and $R^4$ are as defined above.

The term "amino-protecting group", as used herein, signifies a protecting group capable of being cleaved by chemical means, such as hydrogenolysis, hydrolysis, electrolysis or photolysis and such amino-protecting groups are described in Protective Groups in Organic Synthesis edited by T. W. Greene et al. (John Wiley & Sons, 1999). Typical amino-protecting groups include benzyl, $C_2H_5O(C=O)$—, $CH_3(C=O)$—, benzyloxycarbonyl and t-butoxycarbonyl. Of these groups, t-butoxycarbonyl is preferred.

When $R^4$ is hydroxy group and $PG^1$ is present or absent, the compound of formula VIIb ($R^2$ is not hydrogen atom) can be prepared from the compound of formula VIIa ($R^2$ is hydrogen atom) with $R^2$-$LG^1$ by palladium catalyzed coupling or nucleophilic substitution reaction.

When $R^4$ is not hydroxy group and $PG^1$ is absent, the compound of formula VIIb can be prepared from the compound of formula VIIa by the same method as described above.

This palladimun catalyzed coupling or nucleophilic substitution reaction can be carried out by the same procedures as described in Scheme 4.

The desired intermediate, compound of formula II can be prepared by deprotection of amino-protecting group with or without PG1 deprotection reaction in same time of the compound of formula VIIb ($R^2$ is not hydrogen atom).

This deprotection method is described in detail by T. W. Greene et al. [Protective Groups in Organic Synthesis, 494-653, (1999)], the disclosures of which are incorporated herein by reference. The following is a typical method, provided the protecting group is t-butoxycarbonyl.

The deprotection is carried out in the presence of an acid. There is likewise no particular restriction on the nature of the acids used, and any acid commonly used in reactions of this type may equally be used here. Examples of such acids include, but are not limited to: acids, such as trifluoroacetic acid and trifluoromethanesulfonic acid, or hydrogen halide such as HCl, HBr, and HI.

The deprotection is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride, and dichloroethane; ethers, such as diethyl ether, diisopropyl ether, THF, and dioxane, esters such as ethyl acetate, alcohols such as methanol, ethanol, propanol, isopropanol, and butanol, water and aromatic hydrocarbons, such as benzene, toluene, and nitrobenzene. Of these solvents, dichloromethane, dichloroethane, chloroform, water, alcohol, THF, and ethyl acetate are preferred.

The following illustrates a preparation of the intermediate of formula X by ether formation reaction of compound of formula VIII and IX (Scheme 6).

Scheme 6

[Chem. 9]

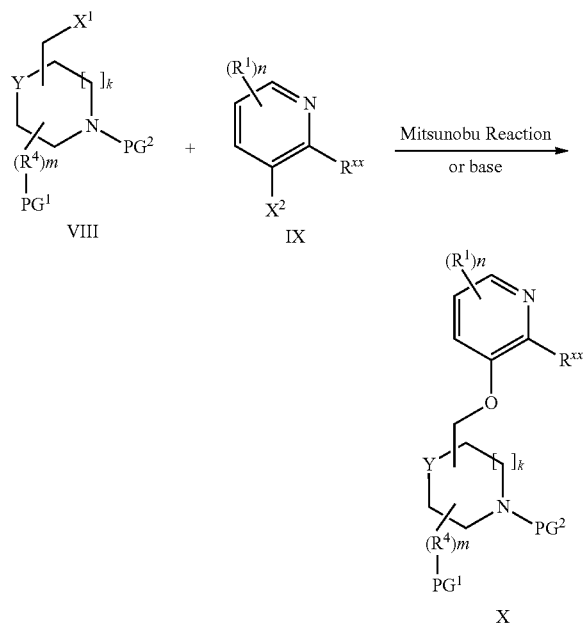

In Scheme 6, $X^1$ and $X^2$ are a leaving groups and/or hydroxy group, $LG^1$, $PG^2$, $PG^3$, Y, $R^1$, and $R^4$ are as defined above and $PG^1$ is hydroxy-protecting group, $R^{xx}$ is hydrogen, nitrile, carboxamide, $CO_2PG^3$.

The term "leaving group", as used herein, signifies a group capable of being substituted by nucleophilic groups, such as a hydroxy group, amines, or carboanions and examples of such leaving groups include halogen atoms, an alkylsulfonyl group and an arylsulfonyl group. Of these, a bromine atom, a chlorine atom, methanesulfonyl group, p-toluenesulfonyl group are preferred.

When leaving groups, $X^1$ and $X^2$ are hydroxy group, the desired compound of formula X can be prepared by Mitsunobu reaction.

Mitsunobu reaction is carried out in the presence of reagent(s). There is likewise no particular restriction on the nature of the reagents used, and any reagent commonly used in reactions of this type may equally be used here. Examples of such reagents include but not limited to:

(a) a combination of (a1) dialkyl azodicarboxylate such as diethyl azodicarboxylate (DEAD), dimethyl azodicarboxylate (DMAD) and diisopropyl azodicarboxylate (DIAD), di-tert-butyl azodicarboxylate (DTAD) and (a2) trialkylphosphine such as tributylphosphine (TBP) or triarylphosphine such as triphenylphosphine (TPP);

(b) a combination of (b1) tetraalkylazodicarboxamide such as N,N,N',N'-tetraisopropylazodicarboxamide (TIPA) and N,N,N',N'-tetramethylazodicarboxamide (TMAD) and (b2) trialkylphosphine such as TBP or triarylphosphine such as TPP;

(c) phosphorane such as cyanomethylenetributylphosphorane (CMBP), cyanomethylenetrimethylphosphorane and dimethyl (tributylphosphoranylidene)malonate (DMTP).

The coupling reaction can take place over a wide range of temperatures, and the precise reaction temperature is not critical to the invention. The preferred reaction temperature will depend upon such factors as the nature of the solvent, the starting materials and reagents used. It is convenient to carry out the reaction at a temperature of from about −78° C. to about 25° C. for reagents (a) and about 50° C. to about 100° C. for reagents (b) and (c). The time required for the reaction may also vary widely, depending on many factors, notably the reaction temperature and the nature of the starting materials and solvent employed. However, provided that the reaction is effected under the preferred conditions outlined above, a period of from about 30 minutes to about 24 hours.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: aliphatic hydrocarbons, such as hexane, heptane, and petroleum ether; halogenated hydrocarbons, such as dichloromethane, chloroform, carbon tetrachloride, and dichloroethane; ethers, such as diethyl ether, diisopropyl ether, THF, dimethoxyethane, and dioxane; aromatic hydrocarbons, such as benzene, toluene, xylene, chlorobenzene, dichlorobenzene, and nitrobenzene; amides, such as formamide, N,N-dimethylformamide, N,N-dimethylacetamide, and hexamethylphosphoric triamide; amines, such as N-methylmorpholine, triethylamine, tripropylamine, tributylamine, diisopropylethylamine, pyridine, 4-pyrrolidinopyridine, N,N-dimethylaniline, and N,N-diethylaniline; nitriles, such as acetonitrile and benzonitrile; sulfoxides, such as dimethyl sulfoxide, and sulfolane. Of these solvents, toluene, benzene, xylene, chlorobenzene, dichlorobenzene, THF, diethylether, diisopropylether, dimethoxyethane, acetonitrile, dichloromethane, dichloroethane, and chloroform are preferred.

In the case of $X^1$ is leaving group as defined above and $X^2$ is hydroxy group or $X^1$ is hydroxy group and $X^2$ is leaving group as defined above, the desired compound of formula X can be prepared by nuculeophilic substitution reaction with presence a suitable base.

This reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, DBN, DABCO, DBU, lutidine, and colidine; alkali metal amides, such as lithium amide, sodium amide, potassium amide, lithium diiropropyl amide, potassium diisopropyl amide, sodium diiropropyl amide, lithium bis(trimethylsilyl)amide and potassium bis(trimethylsilyl)amide. Of these, sodium carbonate, potassium carbonate, and cesium carbonate are preferred.

This reaction can take place over a wide range of temperatures, and the precise reaction temperature is not critical to the invention. The preferred reaction temperature will depend upon such factors as the nature of the solvent, the starting materials and reagents used. It is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 1 hours to about 24 hours.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but not limited to: a halogenated hydrocarbons, such as dichloromethane, chloroform, carbon tetrachloride, and dichloroethane; ethers, such as diethyl ether, diisopropyl ether, THF, dimethoxyethane, and dioxane; aromatic hydrocarbons, such as benzene, toluene, xylene, chlorobenzene, dichlorobenzene, and nitrobenzene; amides, such as formamide, N,N-dimethylformamide, N,N-dimethylacetamide, N-methyl-2-pyrrolidinone, and hexamethylphosphoric triamide; amines, such as N-methylmorpholine, triethylamine, tripropylamine, tributylamine, diisopropylethylamine, pyridine, 4-pyrrolidinopyridine, N,N-dimethylaniline, and N,N-diethylaniline; nitriles, such as acetonitrile and benzonitrile; sulfoxides, such as dimethyl sulfoxide, and sulfolane. Of these solvents, THF, N,N-dimethylformamide, dimethyl sulfoxide and N-methyl-2-pyrrolidinone are preferred.

The following illustrates an alternative preparation of the intermediate of formula Xb ($R^{xx}$ is nitrile) from the compound of formula Xa ($R^{xx}$ is hydrogen) (Scheme 7).

Scheme 7

[Chem. 10]

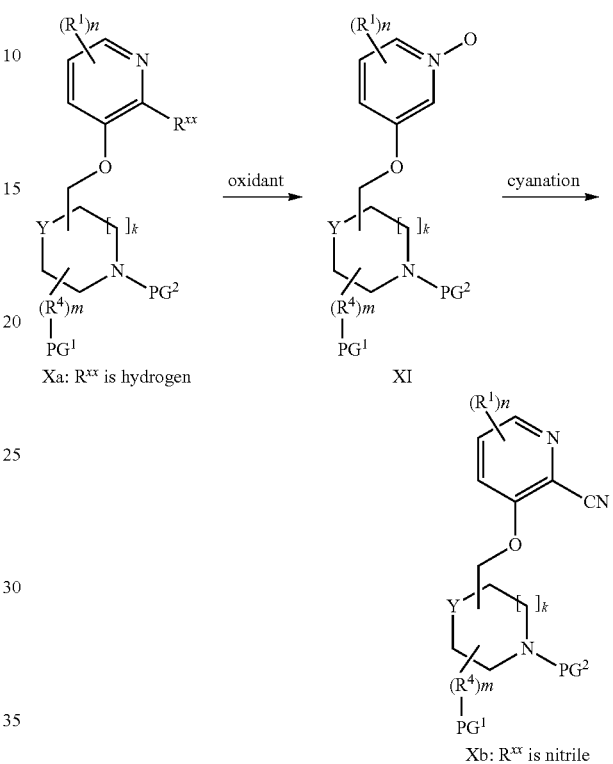

In the Scheme 7, $R^{xx}$ is not hydroxy group, $PG^1$, $PG^2$, Y, $R^1$, and $R^4$ are as defined above.

The desired intermediate of the formula Xb ($R^{xx}$ is nitrile) can be prepared by cyanation of the compound of formula XI. The compound of formula XI can be prepared by N-oxidation by utilizing suitable oxidant, such as m-chloroperbenzoic acid and hydrogen peroxide.

This N-oxidation reaction can take place over a wide range of temperatures, and the precise reaction temperature is not critical to the invention. The preferred reaction temperature will depend upon such factors as the nature of the solvent, the starting materials and reagents used. It is convenient to carry out the reaction at a temperature of from about −50° C. to about 50° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but not limited to: a halogenated hydrocarbons, such as dichloromethane, chloroform, carbon tetrachloride, and dichloroethane; aromatic hydrocarbons, such as benzene, toluene, xylene, chlorobenzene, dichlorobenzene, and nitrobenzene; nitriles, such as acetonitrile and benzonitrile; sulfoxides, such as DMSO. Of these solvents, dichloromethane and DMSO are preferred.

The cyanation is carried out in the presence of reagent(s). There is likewise no particular restriction on the nature of the reagents used, and any reagent commonly used in reactions of this type may equally be used here. Examples of such reagents include but not limited to: silyl cyanide, such as trimethylsilyl cyanide, tert-butyldimethylsilyl cyanide, tert-butyldiphenylsilyl cyanide, alkali cyanide, such as sodium cyanide and potassium cyanide.

This cyanation reaction is normally and preferably effected in the presence of base. There is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, DBN, DABCO, DBU, lutidine, and colidine. Of these, amines, triethylamine and alkali metal hydroxides, sodium hydroxide are preferred.

This reaction can take place over a wide range of temperatures, and the precise reaction temperature is not critical to the invention. The preferred reaction temperature will depend upon such factors as the nature of the solvent, the starting materials and reagents used. It is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 1 hours to about 24 hours.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but not limited to: a halogenated hydrocarbons, such as dichloromethane, chloroform, carbon tetrachloride, and dichloroethane; ethers, such as diethyl ether, diisopropyl ether, THF, dimethoxyethane, and dioxane; aromatic hydrocarbons, such as benzene, toluene, xylene, chlorobenzene, dichlorobenzene, and nitrobenzene; amides, such as formamide, N,N-dimethylformamide, N,N-dimethylacetamide, N-methyl-2-pyrrolidinone, and hexamethylphosphoric triamide; amines, such as N-methylmorpholine, triethylamine, tripropylamine, tributylamine, diisopropylethylamine, pyridine, 4-pyrrolidinopyridine, N,N-dimethylaniline, and N,N-diethylaniline; nitriles, such as acetonitrile and benzonitrile; sulfoxides, such as dimethyl sulfoxide, and sulfolane. Of these solvents, acetonitrile, N,N-dimethylformamide, and dimethyl sulfoxide are preferred.

The following illustrates an alternative preparation of the intermediate of formula IIa ($R^2$ is hydrogen) from the compound of formula Xb ($R^{xx}$ is nitrile) by nitrile partially hydrolysis and $PG^2$ deprotection reactions with or without same time $PG^1$ deprotection reaction in the steps in Scheme 8.

Scheme 8

[Chem. 11]

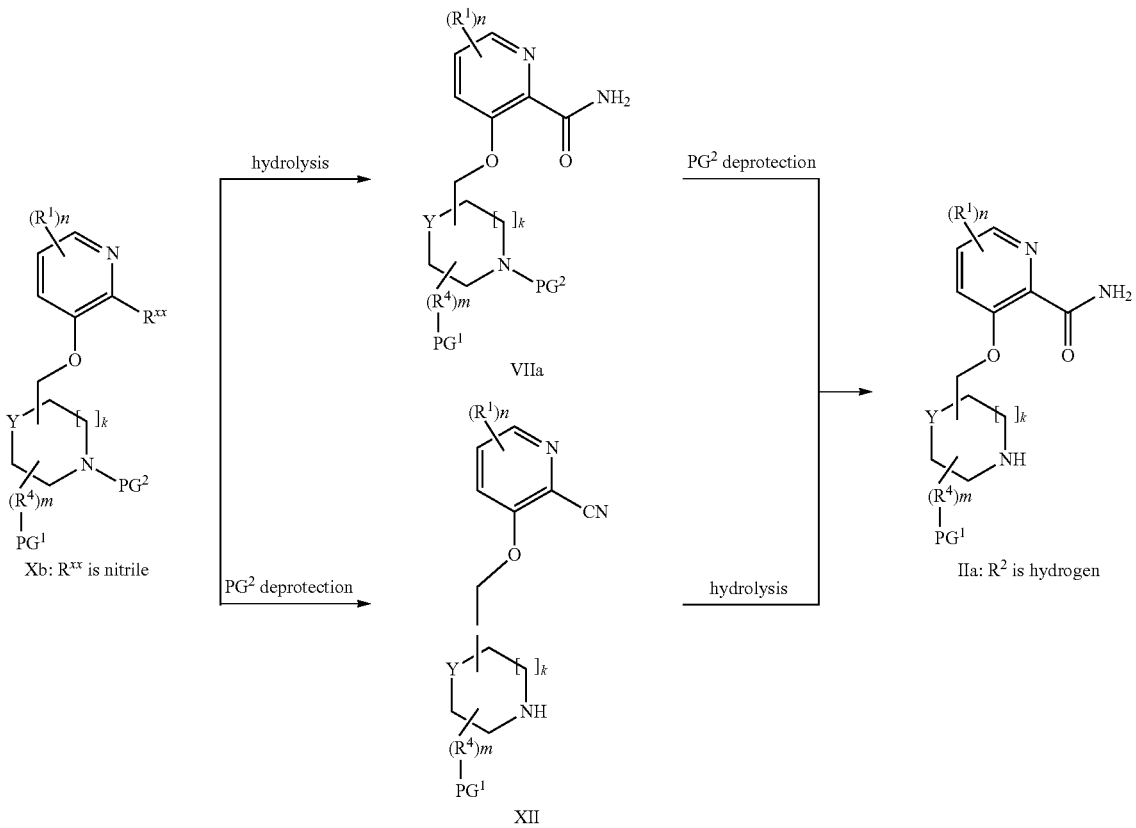

In the Scheme 8, $R^{xx}$ is nitrile, $PG^1$, $PG^2$, Y, $R^1$, and $R^4$ are as defined above. The intermediate of the compound of formula IIa ($R^2$ is hydrogen) can be prepared by partially hydrolysis of nitrile of the compound of formula Xb ($R^{xx}$ is nitrile) and $PG^2$ deprotection reactions via the intermediate of compound of formula VIIa ($R^2$ is hydrogen). The compound of formula IIa ($R^2$ is hydrogen) also can be prepared form the compound formula Xb ($R^{xx}$ is nitrile) by $PG^2$ deprotection and partially hydrolysis of nitrile of the compound of formula XII.

The conditions of this nitrile partially hydrolysis reaction is as described as description of Scheme 2. The conditions of this $PG^2$ with or without $PG^1$ deprotection reaction is as described as description of Scheme 5.

The following illustrates preparation of the intermediate of formula V from the compound of formula XII by peptide bond formation reaction with the activated ester of the formula III or carboxylic acid of the formula IV (Scheme 9).

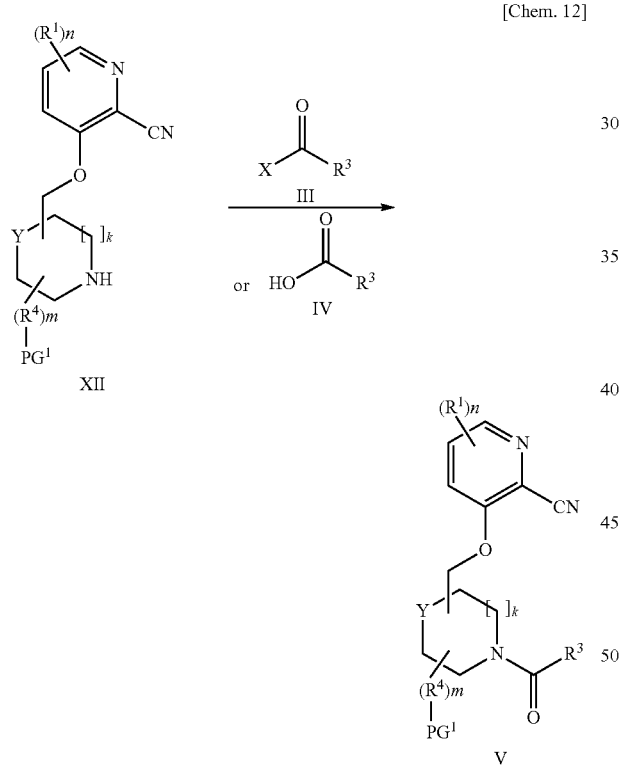

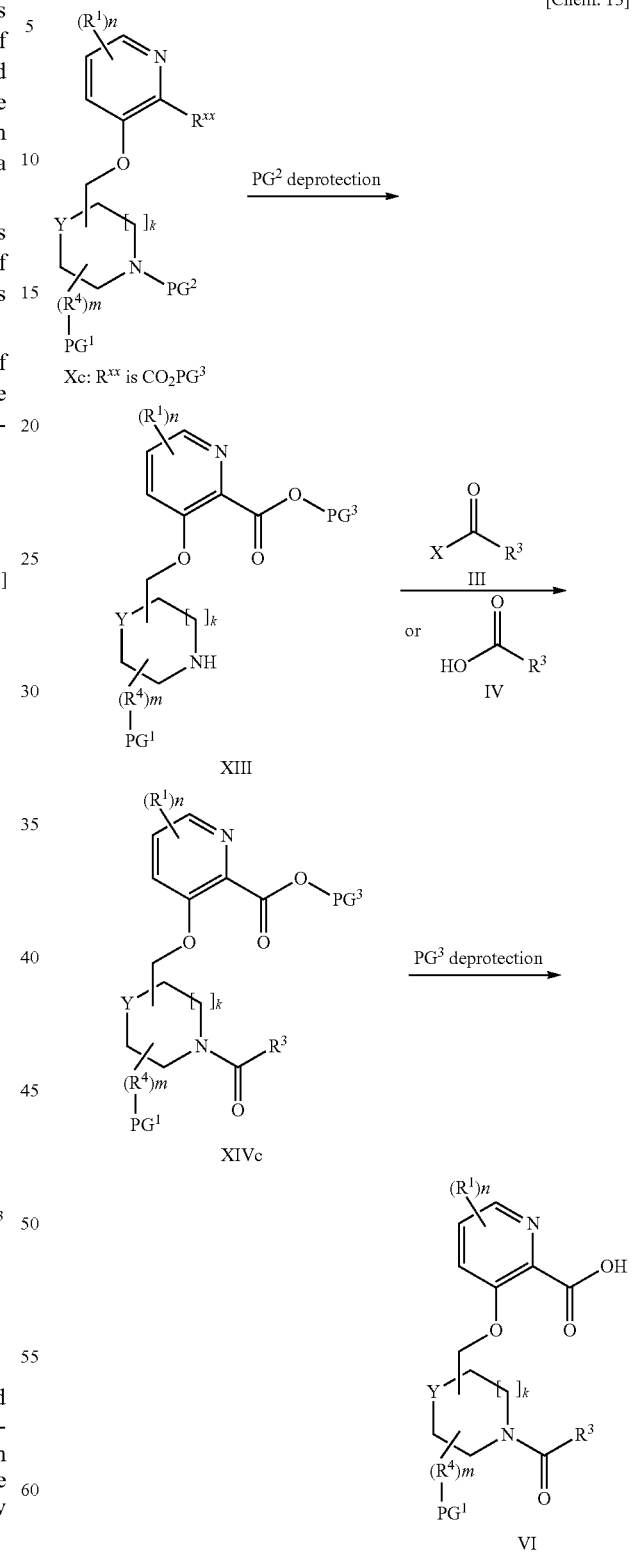

In the Scheme 9, $PG^1$, Y, $R^1$, $R^3$, and $R^4$ are as defined above. The compound of formula V can be prepared by peptide bond formation reaction of amine of the formula XII with activated ester of the formula III or carboxylic acid of the formula IV. This peptide bond formation can be carried out by the same procedures as described in Scheme 1.

The following illustrates preparation of the intermediate of formula XIVc ($R^{xx}$ is $CO_2PG^3$) from the compound of formula Xc ($R^{xx}$ is $CO_2PG^3$) by $PG^2$ (with or without $PG^1$) deprotection, peptide bond formation, and $PG^3$ deprotection reactions (Scheme 10).

In the Scheme 10, $R^{xx}$ is $CO_2PG^3$, $PG^1$, $PG^2$, Y, $R^1$, $R^3$, and $R^4$ are as defined above, and $PG^3$ is a carboxy-protecting group.

The term "carboxy-protecting group", as used herein, signifies a protecting group capable of being cleaved by chemical means, such as hydrogenolysis, hydrolysis, electrolysis, or photolysis, and such carboxy-protecting groups are described in Protective Groups in Organic Synthesis edited by T. W. Greene et al. (John Wiley & Sons, 1999). Typical carboxy-protecting groups include, but are not limited to: methyl, ethyl, t-butyl, methoxymethyl, 2,2,2-trichloroethyl, benzyl, diphenylmethyl, trimethylsilyl, t-butyldimethylsilyl and allyl. Of these groups, ethyl or methyl are preferred.

The compound of formula VI can be prepared from the compound formula Xc ($R^{xx}$ is $CO_2PG^3$) by $PG^2$ deprotection, peptide bond formation, and following $PG^3$ deprotection.

Preparation of the compound of formula XIII from the compound formula Xc ($R^{xx}$ is $CO_2PG^3$) can be carried out $PG^2$ deprotection reaction as same as described in Scheme 5.

The compound of formula XIVc ($PG^3$ is a carboxy-protecting group) can be prepared by peptide bond formation between compound formula XIII and activated ester of the formula III or carboxylic acid of the formula IV. In this step, the peptide bond formation methods are described as description of Scheme 1.

The $PG^3$ deprotection will follow to yield a carboxy group, compound of the formula VI. This reaction is described in detail by T. W. Greene et al., Protective Groups in Organic Synthesis, 369-453, (1999), the disclosures of which are incorporated herein by reference. The following exemplifies a typical reaction involving the protecting group methyl.

The deprotection is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: ethers, such as diethyl ether, diisopropyl ether, THF, and dioxane; and alcohols such as methanol, ethanol, propanol, isopropanol, and butanol. Of these solvents, THF and methanol are preferred.

The deprotection is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide. Of these, sodium hydroxide and potassium hydroxide are preferred.

The deprotection can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about -20° C. to about 120° C., more preferably from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 48 hours.

The following illustrates a preparation of the intermediate of formula VII from the compound of formula Xc ($R^{xx}$ is $CO_2PG^3$) or XV by peptide bond formation (Scheme 11).

Scheme 11

[Chem. 14]

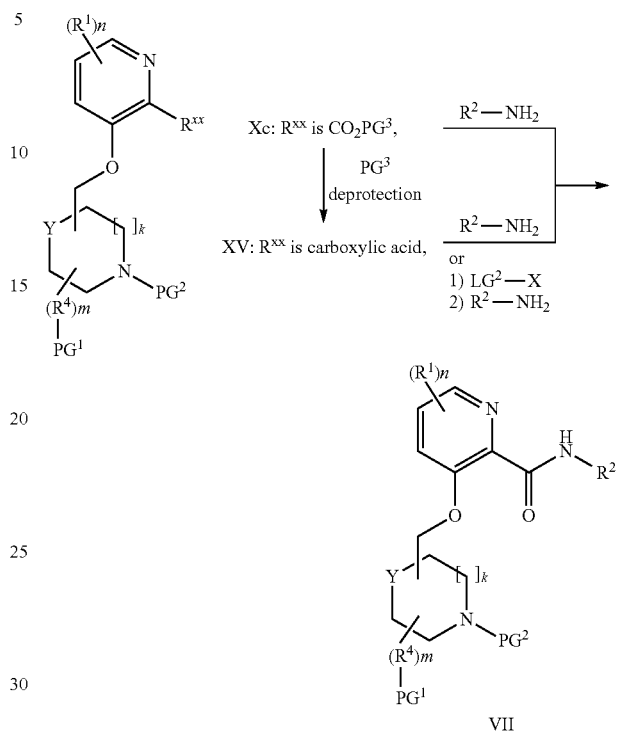

In the Scheme 11, $PG^1$, $PG^2$, $PG^3$, $LG^2$, X, Y, $R^1$, $R^2$, and $R^4$ are as defined above. The desired compound of formula of VII can be prepared by the direct amidation, which is carried out by reacting the ester of formula Xc and amine of formula $R^2$—$NH_2$.

In this reaction, direct amidation of ester can take place over a wide range of temperatures, and the precise reaction temperature is not critical to the invention. The preferred reaction temperature will depend upon such factors as the nature of the solvent, the starting materials and amine used. It is convenient to carry out the reaction at a temperature of from about 50° C. to about 230° C. The time required for the reaction may also vary widely, depending on many factors, notably the reaction temperature and the nature of the starting materials and solvent employed. However, provided that the reaction is effected under the preferred conditions outlined above, a period of from about 1 hours to about 24 hours.

This reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but not limited to: ethers, such as THF, dimethoxyethane, and dioxane; aromatic hydrocarbons, such as benzene, toluene, xylene, chlorobenzene, dichlorobenzene, and nitrobenzene; amides, such as formamide, N,N-dimethylformamide, N,N-dimethylacetamide, N-methyl-2-pyrrolidinone, and hexamethylphosphoric triamide; amines, such as N-methylmorpholine, triethylamine, tripropylamine, tributylamine, diisopropylethylamine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide, and sulfolane. Of these solvents, methanol, N,N-dimethylformamide, N-methyl-2-pyrrolidinone, and dimethyl sulfoxide are preferred.

The desired compound of formula of VII can be prepared by the alternative routes.

In the case of the starting material is compound of formula Xc ($R^{xx}$ is $CO_2PG^3$). The desired compound of formula VII can be prepared by $PG^3$ deprotection and following peptide bond formation with amine of formula $R^2$—$NH_2$ via intermediate of formula XV.

The $PG^3$ deprotection reaction will follow to yield a carboxy group by using the similar method described in Scheme 10.

The peptide bond formation reaction is carried out by using the same methods described in Scheme 4.

On the other hands, in the case of the starting material is compound of formula XV. The desired compound of formula VII can be prepared by peptide bond formation as described above.

The following illustrates a preparation of the intermediate of formula XIV from the compound of formula XVI by sequence of peptide bond formation and coupling reaction (Scheme 12).

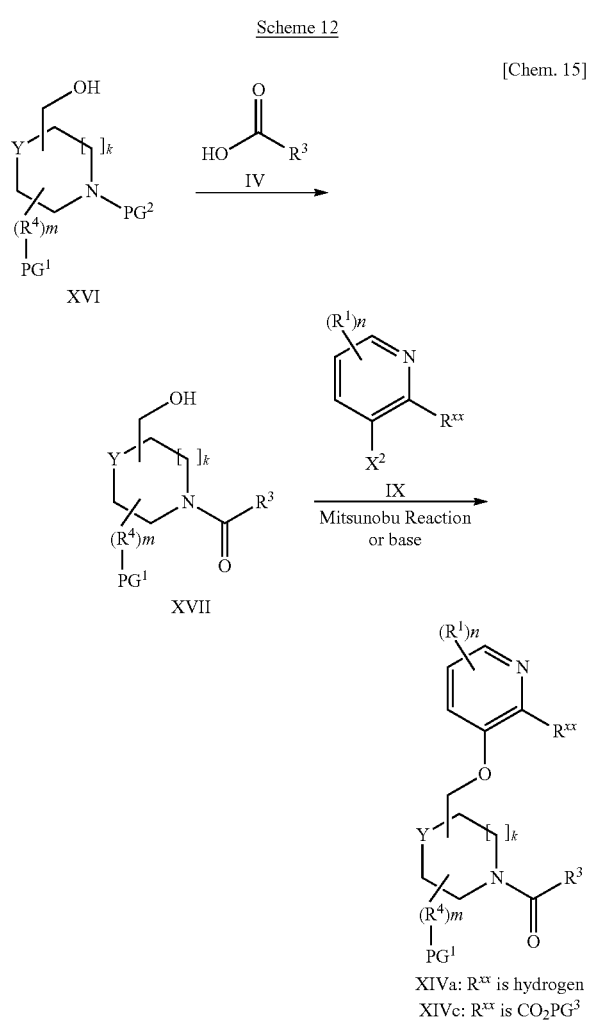

In Scheme 12, $R^{xx}$ is hydrogen atom or $CO_2PG^3$; $X^2$, Y, $PG^3$, $R^1$, $R^3$, and $R^4$ are as defined above and $PG^1$ is hydroxy-protecting group. The desired compound, XIV can be prepared by sequential coupling reactions. The peptide bond formation reaction can be carried out to obtain the compound of formula XVII from the compound formula XVI and IV. The desired compound of formula XIV can be prepared by following coupling reaction between the compound of formula XVII and IX.

The peptide bond formation reaction is carried out by using the same methods described in Scheme 1.

The following coupling reaction is carried out by using the same methods described in Scheme 6.

The following illustrates a preparation of the intermediate of formula V from the compound of formula XIVa ($R^{xx}$ is hydrogen) by the same manner as described in Scheme 7 (Scheme 13).

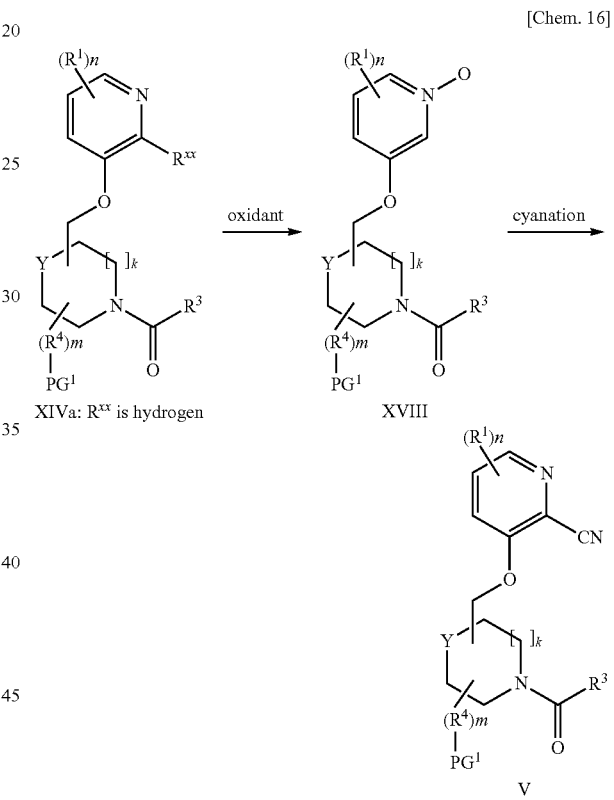

In Scheme 13, $R^{xx}$ is hydrogen atom; $PG^1$, Y, $R^1$, $R^3$, and $R^4$ are as defined above.

The desired intermediate of the formula V can be prepared by cyanation of the compound of formula XVIII. The compound of formula XVIII can be prepared by N-oxidation reaction.

These reaction methods are utilizing same methods as described in Scheme 7.

EXAMPLES

The invention is illustrated in the following non-limiting examples in which, unless stated otherwise: all reagents are commercially available, all operations were carried out at room or ambient temperature, that is, in the range of about 18-25° C.; evaporation of solvent was carried out using a rotary evaporator under reduced pressure with a bath temperature of up to about 60° C.; reactions were monitored by thin layer chromatography (TLC) and reaction times are given for illustration only; the structure and purity of all isolated compounds were assured by at least one of the following techniques: TLC (Merck silica gel 60 F254 precoated TLC plates or Merck NH2 F2548 precoated HPTLC plates), mass spectrometry or nuclear magnetic resonance (NMR). Yields are given for illustrative purposes only. Flash column chromatography was carried out using Merck silica gel 60 (230-400 mesh ASTM) or Fuji Silysia Chromatorex(registered trademark) DU3050 (Amino Type, 30-50 micrometer) or Biotage silica (32-63 mm, KP-Sil) or Biotage amino bounded silica (35-75 mm, KP-NH). The purification of compounds using HPLC was performed by the following apparatus and conditions; Apparatus; Waters MS-trigger AutoPurification™ system Column; Waters XTerra C18, 19×50 mm, 5 mm particle, solvent systems; Methanol or acetonitrile/ 0.05% (v/v) formic acid aqueous solution, or; Methanol or acetonitrile/0.01% (v/v) ammonia aqueous solution. Low-resolution mass spectral data (ESI) were obtained by the following apparatus and conditions: Apparatus; Waters Alliance HPLC system on ZQ or ZMD mass spectrometer and UV detector. NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc.

Chemical symbols have their usual meanings; μL (microliter(s)), μg (microgram(s)), M (mol(s) per liter), L (liter(s)), mL (milliliter(s)), g (gram(s)), mg(milligram(s)), mol (moles), mmol (millimoles).

Conditions for Determining HPLC Retention Time:
Method A:
  Apparatus: Waters Acquity Ultra Performance LC on TUV Detector and ZQ mass spectrometer
  Column: Waters ACQUITY C18, 2.1×50 mm, 1.7 micrometer particle
  Column Temperature: 60° C.
  UV detection: 210 nm scan
  MS detection: ESI positive mode
  Solvents:
  A1: 10 mM ammonium acetate aqueous solution
  B1: acetonitrile

TABLE 1

| Time(min) | A1(%) | B1(%) |
|---|---|---|
| 0 | 95 | 5 |
| 0.1 | 95 | 5 |
| 0.8 | 5 | 95 |
| 1 | 95 | 5 |
| run time | 1.5 min | |
| flow | 1 ml/min | |

Method B:
  Apparatus: Waters Alliance HPLC system on ZQ mass spectrometer and UV detector
  Column: Waters SunFire C18 2.1×50 mm, 3.5 micrometer particle
  Column Temperature: 40° C.
  PDA detection: 210-400 nm scan
  MS detection: ESI positive mode
  Solvents:
  A: water
  B: acetonitrile
  C: 1% (v/v) formic acid aqueous solution

TABLE 2

| Time(min) | A(%) | B(%) | C(%) |
|---|---|---|---|
| 0 | 90 | 5 | 5 |
| 0.5 | 90 | 5 | 5 |
| 3.5 | 0 | 95 | 5 |
| 4.5 | 90 | 5 | 5 |
| run time | | | 5 min |
| flow | | | 1 ml/min |

Method C:
  Apparatus: Waters Acquity Ultra Performance LC on TUV Detector and ZQ mass spectrometer
  Column: Waters ACQUITY C 18, 2.1×100 mm, 1.7 micrometer particle
  Column Temperature: 60° C.
  UV detection: 210 nm scan
  MS detection: ESI positive mode
  Solvents:
  A1: 10 mM ammonium acetate aqueous solution
  B1: acetonitrile

TABLE 3

| Time(min) | A1(%) | B1(%) |
|---|---|---|
| 0 | 95 | 5 |
| 0.1 | 95 | 5 |
| 1.8 | 5 | 95 |
| 2.3 | 95 | 5 |
| run time | | 3 min |
| flow | | 0.7 ml/min |

Method D:
  Apparatus: Waters Acquity Ultra Performance LC on TUV Detector and ZQ mass spectrometer
  Column: Waters ACQUITY C18, 2.1×100 mm, 1.7 micrometer particle
  Column Temperature: 60° C.
  UV detection: 210 nm scan
  MS detection: ESI positive mode
  Solvents:
  A1: 0.05% aqueous ammonia
  B1: acetonitrile

TABLE 4

| Time(min) | A1(%) | B1(%) |
|---|---|---|
| 0 | 95 | 5 |
| 0.1 | 95 | 5 |
| 1.8 | 5 | 95 |
| 2.3 | 95 | 5 |
| run time | | 3 min |
| flow | | 0.7 ml/min |

Method E:
  Apparatus: Waters Alliance HPLC system on ZQ mass spectrometer and UV detector
  Column: Waters XBridge C18 2.1×50 mm, 3.5 micrometer particle
  Column Temperature: 40° C.
  PDA detection: 210-400 nm scan
  MS detection: ESI positive mode
  Solvents:
  A1: water
  B1: acetonitrile
  C1: 1% aqueous ammonia

TABLE 5

| Time(min) | A1(%) | B1(%) | C1(%) |
|---|---|---|---|
| 0 | 90 | 5 | 5 |
| 0.5 | 90 | 5 | 5 |
| 3.5 | 0 | 95 | 5 |
| 4.5 | 95 | 5 | 5 |
| | | run time | 5 min |
| | | flow | 1 ml/min |

All of the picolinamide derivatives of the formula (I) can be prepared by the procedures described in the general methods presented above or by the specific methods described in the Examples section and the Preparations section, or by routine modifications thereof. The present invention also encompasses any one or more of these processes for preparing the picolinamide derivatives of formula (I), in addition to any novel intermediates used therein.

In the following general methods, $R^1$, $R^2$, $R^3$, $R^4$, and n are as previously defined for picolinamide derivatives of the formula (I) unless otherwise stated.

Example 1

3-(((R)-1-(cis-4-(trifluoromethyl)cyclohexanecarbonyl)pyrrolidin-2-yl)methoxy)picolinamide

[Chem. 17]

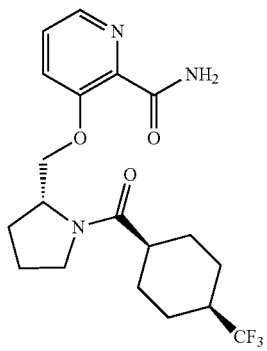

Step 1. (R)-tert-butyl 2-((2-cyanopyridin-3-yloxy)methyl)pyrrolidine-1-carboxylate A mixture of tert-butyl (2R)-2-[(methanesulfonyloxy)methyl]pyrrolidine-1-carboxylate (7.38 g, 26.4 mmol, Tetrahedron Asymmetry, 1997, 8, 2209-2213.), 3-hydroxypicolinonitrile (4.76 g, 39.6 mmol), and potassium carbonate (10.95 g, 79.0 mmol) in N,N-dimethylformamide (150 mL) was stirred at 100° C. for 6 h. After cooling to room temperature, the mixture was poured into water, and the aqueous layer was extracted with ethyl acetate twice. The combined organic layers were dried over magnesium sulfate and concentrated in vacuo. The residual oil was purified by silica gel column chromatography (ethyl acetate/hexane 1:2 to 1:1) to give 3.62 g (45%) of the title compound as a colorless oil.

$^1$H-NMR (CDCl$_3$) δ 8.26 (1H, d, J=4.4 Hz), 7.57 (1H, d, J=8.1 Hz), 7.46 (1H, dd, J=8.1, 4.4 Hz), 4.30-3.95 (3H, m), 3.48-3.28 (2H, m), 2.19-1.83 (4H, m), 1.46 (9H, s).

MS (ESI) m/z: 304 (M+H)$^+$.

Step 2. (R)-tert-butyl 2-((2-carbamoylpyridin-3-yloxy)methyl)pyrrolidine-1-carboxylate To a solution of (R)-tert-butyl 2-((2-cyanopyridin-3-yloxy)methyl)pyrrolidine-1-carboxylate (3.62 g, 11.9 mmol, EXAMPLE 1 Step 1) in tert-butanol (110 mL) was added potassium hydroxide pellet (10.0 g, 179 mmol) at room temperature. The resulting mixture was stirred at 80° C. for 0.5 h. After cooling to room temperature, the mixture was poured into water, and the aqueous layer was extracted with ethyl acetate twice. The combined organic layers were washed with brine, dried over magnesium sulfate, and concentrated in vacuo. The residual oil was purified by silica gel column chromatography (dichloromethane to methanol/dichloromethane 1:15) to give 3.43 g (90%) of the title compound as a white amorphous powder.

$^1$H-NMR (CDCl$_3$) δ 8.26 (1H, d, J=4.4 Hz), 7.71 (1H, br), 7.56 (1H, d, J=8.1 Hz), 7.40 (1H, dd, J=8.1, 4.4 Hz), 5.67 (1H, br), 4.30-3.90 (3H, m), 3.49-3.33 (2H, m), 2.23-1.60 (4H, m), 1.46 (9H, s).

MS (ESI) m/z: 322 (M+H)$^+$.

Step 3. (R)-3-(pyrrolidin-2-ylmethoxy)picolinamide dihydrochloride

A solution of (R)-tert-butyl 2-((2-carbamoylpyridin-3-yloxy)methyl)pyrrolidine-1-carboxylate (3.43 g, 10.7 mmol, EXAMPLE 1 Step 2) in 4.0 M hydrogen chloride in ethyl acetate (100 mL) was stirred at room temperature for 5 h. Diisopropyl ether (150 mL) was added to the mixture, and the formed white precipitate was collected by filtration. The precipitate was dried under reduced pressure to give 2.89 g (92%) of the title compound as a white solid.

$^1$H-NMR (DMSO-d6) δ 9.60 (1H, br), 9.13 (1H, br), 8.27 (1H, d, J=4.4 Hz), 7.97 (1H, br), 7.74 (1H, d, J=8.8 Hz), 7.57 (1H, dd, J=8.8, 4.4 Hz), 4.43-4.35 (1H, m), 4.33-4.23 (1H, m), 4.05-3.8 (1H, m), 3.39-3.19 (2H, m), 2.20-1.98 (2H, m), 1.96-1.80 (4H, m).

MS (ESI) m/z: 222 (M+H).

Step 4. 3-(((R)-1-(cis-4-(trifluoromethyl)cyclohexanecarbonyl)pyrrolidin-2-yl)methoxy)picolinamide To an ice-cold solution of cis-4-(trifluoromethyl)cyclohexanecarboxylic acid (267 mg, 1.36 mmol) in dichloromethane (5 mL), oxalyl chloride (0.18 mL, 2.04 mmol) and several drop of N,N-dimethylformamide were added. After being stirred at room temperature for 1 h, the mixture was concen-

47 trated in vacuo to give a waxy solid. The residual solid was dissolved with dichloromethane (3 mL) and added to the mixture of (R)-3-(pyrrolidin-2-ylmethoxy)picolinamide dihydrochloride (200 mg, 0.68 mmol, EXAMPLE 1 Step 3) and triethylamine (0.48 mL, 3.40 mmol) in dichloromethane (5 mL) at 0° C. After being stirred at 0° C. for 2 h, the mixture was dissolved with ethyl acetate and 2 N hydrochloric acid. The aqueous layer was washed with ethyl acetate, and basified with aq. ammonia. The mixture was extracted with ethyl acetate twice, and washed with brine. The combined extracts were dried over sodium sulfate and concentrated in vacuo to give an amber oil. The residual oil was purified by preparative TLC (methanol/dichloromethane 1:10) to afford 160 mg of the title compound as a colorless viscous oil.

$^1$H-NMR (CDCl$_3$) δ 8.20 (1H, dd, J=4.4, 1.5 Hz), 7.61 (1H, brs), 7.55 (1H, dd, J=8.8, 1.5 Hz), 7.21 (1H, dd, J=8.1, 4.4 Hz), 5.56 (1H, brs), 4.45 (1H, m), 4.33 (1H, dd, J=9.5, 5.9 Hz), 4.21 (1H, dd, J=10.3, 2.9 Hz), 3.7-3.6 (1H, m), 3.6-3.4 (1H, m), 2.63 (1H, m), 2.4-2.1 (2H, m), 2.2-1.8 (6H, m), 1.8-1.5 (5H, m).

MS (ESI) m/z: 400 (M+H)$^+$.

HPLC Retention time: 0.66 min (Method A).

Example 2

3-(((S)-1-(cis-4-(trifluoromethyl)cyclohexanecarbonyl)pyrrolidin-2-yl)methoxy)picolinamide

[Chem. 18]

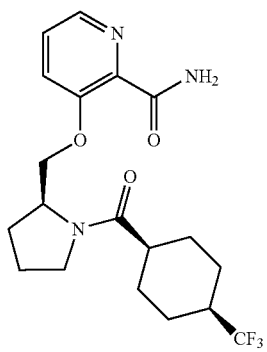

The title compound was prepared according to the procedure described in EXAMPLE 1 using (S)-tert-butyl 2-((methylsulfonyloxy)methyl)pyrrolidine-1-carboxylate (Tetrahedron Asymmetry, 1997, 8, 2209-2213.) instead of (R)-tert-butyl 2-((methylsulfonyloxy)methyl)pyrrolidine-1-carboxylate.

$^1$H-NMR (CDCl$_3$) δ 8.20 (1H, dd, J=4.4, 1.5 Hz), 7.61 (1H, brs), 7.55 (1H, dd J=8.8, 1.5 Hz), 7.41 (1H, dd, J=8.8, 4.4 Hz), 5.62 (1H, brs), 4.45 (1H, m), 4.32 (1H, dd, J=9.5, 5.9 Hz), 4.21 (1H, dd, J=9.5, 2.9 Hz), 3.7-3.6 (1H, m), 3.50 (1H, m), 2.63 (1H, m), 2.4-2.2 (2H, m), 2.2-1.8 (6H, m), 1.8-1.4 (5H, m).

MS (ESI) m/z: 400 (M+H)$^+$.

HPLC Retention time: 0.66 min (Method A).

48

Example 3

(R)-3-((1-(1H-indole-2-carbonyl)pyrrolidin-2-yl)methoxy)picolinamide

[Chem. 19]

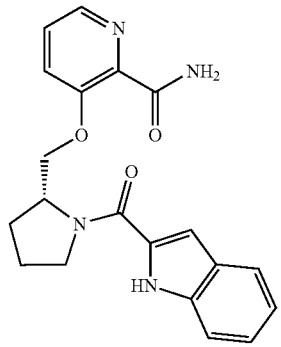

Step 1. (R)-3-((1-(1H-indole-2-carbonyl)pyrrolidin-2-yl)methoxy)picolinamide

A mixture of (R)-3-(pyrrolidin-2-ylmethoxy)picolinamide dihydrochloride (25 mg, 0.085 mmol, EXAMPLE 1 Step 3), indole-2-carboxylic acid (15 mg, 0.093 mmol), triethylamine (0.060 mL, 0.43 mmol), and N,N,N',N'-tetramethyl-O-(1H-benzotriazol-1-yl)uronium hexafluorophosphate (HBTU) (48 mg, 0.13 mmol) in acetonitrile (1 mL) was stirred at room temperature for 4 h. The mixture was poured into water, and the aqueous layer was extracted with dichloromethane twice. The combined organic layers were dried over magnesium sulfate and concentrated in vacuo. The residual solid was washed with methanol to give 22 mg (71%) of the title compound as a white solid.

$^1$H-NMR (DMSO-d6) δ 11.60 (1H, s), 8.11 (1H, d, J=4.4 Hz), 7.80-7.60 (3H, m), 7.51-7.37 (3H, m), 7.19 (1H, t, J=8.0 Hz), 7.04 (1H, t, J=7.3 Hz), 6.98 (1H, br), 4.62-4.52 (1H, m), 4.33-4.15 (2H, m), 4.00-3.83 (2H, m), 2.32-1.90 (4H, m).

MS (ESI) m/z: 365 (M+H)$^+$, 363 (M−H)$^-$.

Example 4-28

[Chem. 20]

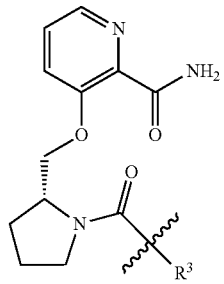

The following examples, EXAMPLE 4-28, were prepared according to the procedure similar to that described in the Step 1 of the EXAMPLE 3, using the appropriate precursor instead of indole-2-carboxylic acid. In the following examples, products of Example 4-28 were purified by preparative HPLC.

TABLE 6-1

| EXAMPLES | R³ | Chemical Name | HPLC Gradient Method | HPLC Retention Time (min.) | MS (ESI): m/z (M + H)+ |
|---|---|---|---|---|---|
| 4 | | (R)-3-((1-(1-methylcyclohexane-carbonyl)pyrrolidin-2-yl)methoxy)picolinamide | Method D | 1.43 | 346 |
| 5 | | (R)-3-((1-(4-(trifluoromethyl)benzoyl)pyrrolidin-2-yl)methoxy)picolinamide | Method D | 1.38 | 394 |
| 6 | | (R)-3-((1-(4-chloro-3-fluorobenzoyl)pyrrolidin-2-yl)methoxy)picolinamide | Method D | 1.35 | 378 |
| 7 | | (R)-3-((1-(3-chloro-4-fluorobenzoyl)pyrrolidin-2-yl)methoxy)picolinamide | Method D | 1.33 | 378 |
| 8 | | (R)-3-((1-(3-chloro-2-fluorobenzoyl)pyrrolidin-2-yl)methoxy)picolinamide | Method D | 1.30 | 378 |
| 9 | | (R)-3-((1-(4-chloro-2-fluorobenzoyl)pyrrolidin-2-yl)methoxy)picolinamide | Method D | 1.32 | 378 |
| 10 | | (R)-3-((1-(3-fluoro-4-methylbenzoyl)pyrrolidin-2-yl)methoxy)picolinamide | Method D | 2.31 | 358 |
| 11 | | (R)-3-((1-(2-(2,4-difluorophenyl)acetyl)pyrrolidin-2-yl)methoxy)picolinamide | Method D | 1.29 | 376 |
| 12 | | (R)-3-((1-(2-(4-(trifluoromethyl)phenyl)acetyl)pyrrolidin-2-yl)methoxy)picolinamide | Method D | 1.42 | 408 |

TABLE 6-2

| EXAMPLES | R³ | Chemical Name | HPLC Gradient Method | HPLC Retention Time (min.) | MS (ESI): m/z (M + H)+ |
|---|---|---|---|---|---|
| 13 | | (R)-3-((1-(3-p-tolylpropanoyl)pyrrolidin-2-yl)methoxy)picolinamide | Method D | 1.40 | 368 |
| 14 | | (R)-3-((1-(cyclohexanecarbonyl)pyrrolidin-2-yl)methoxy)picolinamide | Method C | 1.30 | 332 |
| 15 | | (R)-3-((1-(1-methyl-5-(trifluoromethyl)-1H-pyrazole-3-carbonyl)pyrrolidin-2-yl)methoxy)picolinamide | Method C | 1.29 | 398 |
| 16 | | (R)-3-((1-(6-tert-butylnicotinoyl)pyrrolidin-2-yl)methoxy)picolinamide | Method C | 1.33 | 383 |
| 17 | | (R)-3-((1-(5-tert-butylisoxazole-3-carbonyl)pyrrolidin-2-yl)methoxy)picolinamide | Method C | 1.42 | 373 |
| 18 | | (R)-3-((1-(2-(4-(trifluoromethyl)phenoxy)acetyl)pyrrolidin-2-yl)methoxy)picolinamide | Method C | 1.43 | 424 |
| 19 | | (R)-3-((1-(4-fluoro-3-methylbenzoyl)pyrrolidin-2-yl)methoxy)picolinamide | Method C | 1.30 | 358 |
| 20 | | (R)-3-((1-(1-(2,2,2-trifluoroethyl)piperidine-4-carbonyl)pyrrolidin-2-yl)methoxy)picolinamide | Method C | 1.25 | 415 |

TABLE 6-2-continued

| EXAMPLES | R³ | Chemical Name | HPLC Gradient Method | HPLC Retention Time (min.) | MS (ESI): m/z (M + H)+ |
|---|---|---|---|---|---|
| 21 | (4-(2,2,2-trifluoroethoxy)phenyl) | (R)-3-((1-(4-(2,2,2-trifluoroethoxy)benzoyl)pyrrolidin-2-yl)methoxy)picolinamide | Method C | 1.38 | 424 |

TABLE 6-3

| EXAMPLES | R³ | Chemical Name | HPLC Gradient Method | HPLC Retention Time (min.) | MS (ESI): m/z (M + H)+ |
|---|---|---|---|---|---|
| 22 | (4,4-difluorocyclohexyl) | (R)-3-((1-(4,4-difluoro-cyclohexanecarbonyl)pyrrolidin-2-yl)methoxy)picolinamide | Method C | 1.23 | 368 |
| 23 | (5-(trifluoromethyl)pyridin-2-yl) | (R)-3-((1-(5-(trifluoromethyl)picolinoyl)pyrrolidin-2-yl)methoxy)picolinamide | Method C | 1.28 | 395 |
| 24 | (6-(trifluoromethyl)pyridin-3-yl) | (R)-3-((1-(6-(trifluoromethyl)nicotinoyl)pyrrolidin-2-yl)methoxy)picolinamide | Method C | 1.24 | 395 |
| 25 | (4-(trifluoromethoxy)phenyl) | (R)-3-((1-(4-(trifluoromethoxy)benzoyl)pyrrolidin-2-yl)methoxy)picolinamide | Method D | 1.42 | 410 |
| 26 | (1-methyl-1H-indol-2-yl) | (R)-3-((1-(1-methyl-1H-indole-2-carbonyl)pyrrolidin-2-yl)methoxy)picolinamide | Method C | 1.38 | 379 |
| 27 | (1H-indol-3-yl) | (R)-3-((1-(1H-indole-3-carbonyl)pyrrolidin-2-yl)methoxy)picolinamide | Method C | 1.16 | 365 |

TABLE 6-3-continued

| EXAMPLES | R³ | Chemical Name | HPLC Gradient Method | HPLC Retention Time (min.) | MS (ESI): m/z (M + H)+ |
|---|---|---|---|---|---|
| 28 | | (R)-3-((1-(1-methyl-1H-indole-3-carbonyl)pyrrolidin-2-yl)methoxy)picolinamide | Method C | 1.27 | 379 |

Example 29

5-chloro-3-(((R)-1-(cis-4-(trifluoromethyl)cyclohexanecarbonyl)pyrrolidin-2-yl)methoxy)picolinamide

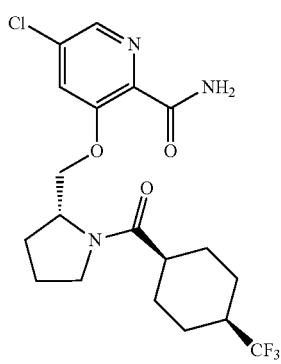

[Chem. 21]

Step 1. (R)-tert-butyl 2-((5-chloropyridin-3-yloxy)methyl)pyrrolidine-1-carboxylate To a stirred solution of 5-chloropyridin-3-ol (1.46 g, 11.28 mmol), (R)-tert-butyl 2-(hydroxymethyl)pyrrolidine-1-carboxylate (2.27 g, 11.28 mmol), and triphenylphosphine (2.96 g, 11.28 mmol) in THF (50 mL) was added di-tert-butyl azodicarboxylate (DTAD) (2.60 g, 11.28 mmol) at 0° C. The mixture was stirred at 0° C. for 1 h and warmed to room temperature. After being stirred at room temperature for 2 days, the mixture was concentrated in vacuo to afford a dark brown viscous oil. The residual oil was crystallized from isopropyl ether (IPE)-hexane, and formed precipitate was removed by filtration. The filtrate was concentrated in vacuo to afford a dark brown oil. The residual oil was purified by silica gel column chromatography (ethyl acetate/hexane 1:9 to 1:5) to afford crude 5.15 g (quant.) of the title compound as a colorless gel. The crude title compound was used for the next step without further purification.

¹H-NMR (CDCl₃) δ 8.22 (2H, br), 7.32 (1H, br), 4.2-3.8 (3H, m), 3.36 (2H, br), 2.1-1.8 (4H, m), 1.48 (9H, s).
MS (EST) m/z: 313 (M+H)⁺.

Step 2. (R)-3-((1-(tert-butoxycarbonyl)pyrrolidin-2-yl)methoxy)-5-chloropyridine 1-oxide To a stirred mixture of crude (R)-tert-butyl 2-((5-chloropyridin-3-yloxy)methyl)pyrrolidine-1-carboxylate (5.15 g, Ca. 11.28 mmol, EXAMPLE 29 Step 1) and sodium bicarbonate (2.77 g, 32.9 mmol) in dichloromethane was added m-chloroperbenzoic acid (mCPBA) (4.26 g, 24.7 mmol) at 0° C. The mixture was stirred at 0° C. for 30 min, and the mixture was warmed to room temperature during 30 min period. After being stirred at room temperature for 6 h, water was added to the mixture. The mixture was extracted with dichloromethane twice and washed with aq. sodium thiosulfate and brine. The extracts were combined and dried over sodium sulfate and concentrated in vacuo to afford an oil. The residual oil was purified by silica gel column chromatography (ethyl acetate/hexane 7:3 to ethyl acetate) to afford 2.709 g (73% from 5-chloropyridin-3-ol) of the title compound as a colorless viscous oil.

¹H-NMR (CDCl₃) δ 7.90 (2H, brs), 7.0-6.9 (1H, br), 4.2-3.8 (3H, m), 3.34 (2H, br), 2.2-1.8 (4H, m), 1.47 (9H, s).
MS (ESI) m/z: 329 (M+H)⁺.

Step 3. (R)-tert-butyl 2-((5-chloro-2-cyanopyridin-3-yloxy)methyl)pyrrolidine-1-carboxylate To a stirred solution of (R)-3-((1-(tert-butoxycarbonyl)pyrrolidin-2-yl)methoxy)-5-chloropyridine 1-oxide (610 mg, 1.855 mmol, EXAMPLE 29 Step 2) and triethylamine (1.56 mL, 11.13 mmol) in acetonitrile was added trimethylsilyl cyanide (TMSCN) (1.24 mL, 9.28 mmol) at ambient temperature and the mixture was heated at 80° C. After being stirred at 80° C. for 15 h, the mixture was cooled to room temperature. 1.24 mL of TMSCN (9.28 mmol) and 1.56 mL of triethylamine (11.13 mmol) were added to the mixture and the mixture was heated at 80° C. further 6 h. After cooling to room temperature, the mixture was concentrated in vacuo to give a dark brown oil. The residual oil was dissolved with ethyl acetate and 2 N aq. sodium hydroxide. The mixture was extracted with ethyl acetate twice and washed with water, 2 N hydrochloric acid, and brine. The extracts were combined and dried over sodium sulfate and concentrated in vacuo to afford an oil. The residual oil was purified by silica gel column chromatography (hexane to ethyl acetate/hexane 1:4) to afford 364 mg (58%) of the title compound as a waxy solid.

¹H-NMR (CDCl₃) δ 8.23 (1H, brs), 7.57 (0.7H, brs), 7.39 (0.3H, brs), 3.9-4.4 (3H, m), 3.40 (2H, br), 2.10 (3H, brs) 2.0-1.8 (1H, br), 1.46 (9H, s).
MS (ESI) m/z: 338 (M+H)⁺.

Step 4. (R)-tert-butyl 2-((2-carbamoyl-5-chloropyridin-3-yloxy)methyl)pyrrolidine-1-carboxylate The title compound was prepared according to the procedure described in Step 2 of EXAMPLE 1 using (R)-tert-butyl 2-((5-chloro-2-cyanopyridin-3-yloxy)methyl)pyrrolidine-1-carboxylate (EXAMPLE 29 Step 3) instead of (R)-tert-butyl 2-((2-cyanopyridin-3-yloxy)methyl)pyrrolidine-1-carboxylate.

$^1$H-NMR (CDCl$_3$) δ 8.22 (1H, brs), 7.7-7.4 (2H, brm), 5.79 (1H, br), 4.3-3.9 (3H, m), 3.39 (2H, br), 2.2-1.7 (4H, m), 1.46 (9H, s).
MS (ESI) m/z: 356 (M+H)$^+$.

Step 5. (R)-5-chloro-3-(pyrrolidin-2-ylmethoxy) picolinamide dihydrochloride

The title compound was prepared according to the procedure described in Step 3 of EXAMPLE 1 using (R)-tert-butyl 2-((2-carbamoyl-5-chloropyridin-3-yloxy)methyl)pyrrolidine-1-carboxylate (EXAMPLE 29 Step 4) instead of (R)-tert-butyl 2-((2-carbamoylpyridin-3-yloxy)methyl)pyrrolidine-1-carboxylate.
$^1$H-NMR (DMSO-d6) δ 9.66 (1H, br), 9.19 (1H, br), 8.28 (1H, d, J=1.6 Hz), 8.02 (1H, brs), 7.89 (1H, d, J=1.7 Hz), 7.68 (1H, brs), 4.5-4.2 (2H, m), 4.2-3.8 (2H, m), 3.22 (2H, br), 2.2-1.7 (4H, m).
MS (ESI) m/z: 256 (M+H)$^+$.

Step 6. 5-chloro-3-(((R)-1-(cis-4-(tri fluoromethyl) cyclohexanecarbonyl)pyrrolidin-2-yl)methoxy)picolinamide The title compound was prepared according to the procedure described in Step 1 of EXAMPLE 3 using (R)-5-chloro-3-(pyrrolidin-2-ylmethoxy)picolinamide dihydrochloride (EXAMPLE 29 Step 5) and cis-4-(trifluoromethyl)cyclohexanecarboxylic acid instead of (R)-3-(pyrrolidin-2-ylmethoxy)picolinamide dihydrochloride and indole-2-carboxylic acid.
$^1$H-NMR (CDCl$_3$) δ 8.15 (1H, d, J=1.5 Hz), 7.51 (2H, brd, J=1.2 Hz), 5.50 (1H, br), 4.5-4.0 (1H, m), 4.37 (1H, dd, J=9.5, 5.1 Hz), 4.15 (1H, dd, J=9.5, 2.9 Hz), 3.69 (1H, m), 3.52 (1H, m), 2.64 (1H, m), 2.4-2.2 (1H, m), 2.2-1.8 (7H, m), 1.8-1.5 (5H, m).
MS (ESI) m/z: 434 (M+H)$^+$.
HPLC Retention time: 0.73 min (Method A).

Example 30

5-chloro-3-(((R)-1-(trans-4-(trifluoromethyl)cyclohexanecarbonyl)pyrrolidin-2-yl)methoxy)picolinamide

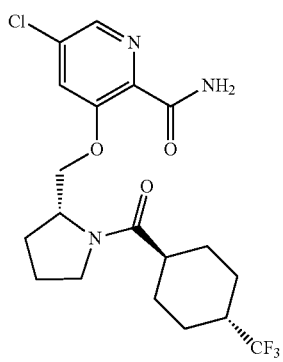

[Chem. 22]

The title compound was prepared according to the procedure described in Step 1 of EXAMPLE 3 using (R)-5-chloro-3-(pyrrolidin-2-ylmethoxy)picolinamide dihydrochloride (EXAMPLE 29 Step 5) and trans-4-(trifluoromethyl)cyclohexanecarboxylic acid instead of (R)-3-(pyrrolidin-2-ylmethoxy)picolinamide dihydrochloride and indole-2-carboxylic acid.
$^1$H-NMR (CDCl$_3$) δ 8.14 (1H, d, J=1.2 Hz), 7.53 (2H, brd, J=1.5 Hz), 5.50 (1H, br), 4.45 (1H, m), 4.32 (1H, dd, J=9.5, 5.1 Hz), 4.17 (1H, dd, J=9.5, 3.7 Hz), 3.70 (1H, m), 3.54 (1H, m), 2.4-2.2 (2H, m), 2.2-1.8 (8H, m), 1.6-1.2 (4H, m).
MS (ESI) m/z: 434 (M+H)$^+$.

Example 31

5-methoxy-3-(((R)-1-(trans-4-(trifluoromethyl)cyclohexanecarbonyl)pyrrolidin-2-yl)methoxy)picolinamide

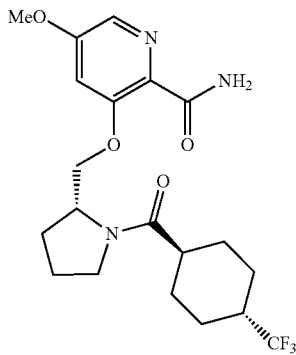

[Chem. 23]

Step 1. [(2R)-1-{[trans-4-(trifluoromethyl)cyclohexyl]carbonyl}pyrrolidin-2-yl]methanol The title compound was prepared according to the procedure described in Step 1 of EXAMPLE 3 using (R)-pyrrolidin-2-ylmethanol and trans-4-(trifluoromethyl)cyclohexanecarboxylic acid instead of (R)-3-(pyrrolidin-2-ylmethoxy) picolinamide dihydrochloride and indole-2-carboxylic acid.
$^1$H-NMR (CDCl$_3$) δ 5.03 (1H, dd, J=8.1, 2.2 Hz), 4.3-4.2 (1H, m), 3.7-3.5 (4H, m), 2.37 (1H, m), 2.2-1.8 (8H, m), 1.8-1.5 (3H, m), 1.5-1.2 (2H, m).
MS (ESI) m/z: 280 (M+H)$^+$.

Step 2. ethyl 3-hydroxy-5-methoxypicolinate 3-hydroxy-5-methoxypicolinic acid (200 mg, 1.18 mmol) was dissolved in ethanol (10 mL). To the mixture was added one drop of sulfuric acid. The mixture was refluxed with stirring for 3 days. After cooling to room temperature, the mixture was concentrated in vacuo to afford an oil. The residual oil was dissolved in ethyl acetate and washed with aq. sodium bicarbonate and brine. The extract was dried over sodium sulfate and concentrated in vacuo to afford an oil. The residual oil was purified by silica gel column chromatography (ethyl acetate/hexane 1:3 to 1:1) to afford 178 mg (76%) of the title compound as a white solid.
$^1$H-NMR (CDCl$_3$) δ 11.00 (1H, s), 7.99 (1H, d, J=2.2 Hz), 6.77 (1H, d, J=2.2 Hz), 4.50 (2H, q, J=6.6 Hz), 3.88 (3H, s), 1.47 (3H, t, J=6.6 Hz).
MS (ESI) m/z: 198 (M+H)$^+$, 196 (M−H)$^-$.

Step 3. ethyl 5-methoxy-3-(((R)-1-(trans-4-(trifluoromethyl)cyclohexanecarbonyl)pyrrolidin-2-yl)methoxy)picolinate The title compound was prepared according to the procedure described in Step 1 of EXAMPLE 29 using ethyl 3-hydroxy-5-methoxypicolinate (EXAMPLE 31 Step 2) and [(2R)-1-{[trans-4-(trifluoromethyl)cyclohexyl]carbonyl}pyrrolidin-2-yl]methanol (EXAMPLE 31 Step 1) instead of 5-chloropyridin-3-ol and (R)-pyrrolidin-2-ylmethanol.

$^1$H-NMR (CDCl$_3$) δ 7.97 (1H, d, J=2.2 Hz), 7.09 (1H, d, J=2.2 Hz), 4.42 (1H, m), 4.40 (2H, q, J=7.3 Hz), 4.30-4.15 (2H, m), 3.92 (3H, s), 3.70-3.45 (2H, m), 2.50-1.75 (10H, m), 1.70-1.25 (4H, m), 1.41 (3H, t, J=6.6 Hz).

MS (ESI) m/z: 459 (M+H)$^+$.

Step 4. 5-methoxy-3-(((R)-1-(trans-4-(trifluoromethyl)cyclohexanecarbonyl)pyrrolidin-2-yl)methoxy)picolinic acid To a solution of 5-methoxy-3-(((R)-1-(trans-4-(trifluoromethyl)cyclohexanecarbonyl)pyrrolidin-2-yl)methoxy)picolinate (170 mg, 0.37 mmol, EXAMPLE 31 Step 3) in tetrahydrofuran was added 2 N aq. sodium hydroxide (0.5 mL, 1.00 mmol) at room temperature. After being stirred at room temperature for 24 h, water and diethylether were added to the mixture. The aqueous layer was washed with diethylether and acidified with 2 N hydrochloric acid. The aqueous layer was extracted with ethyl acetate. The extract was dried over sodium sulfate and concentrated in vacuo to afford 151 mg (95%) of the title compound as an oil. The residual oil was used for the next step without further purification.

MS (ESI) m/z: 431 (M+H)$^+$, 429 (M−H)$^-$.

Step 5. 5-methoxy-3-(((R)-1-(trans-4-(trifluoromethyl)cyclohexanecarbonyl)pyrrolidin-2-yl)methoxy)picolinamide To a solution of 5-methoxy-3-(((R)-1-(trans-4-(trifluoromethyl)cyclohexanecarbonyl)pyrrolidin-2-yl)methoxy)picolinic acid (150 mg, 0.35 mmol, EXAMPLE 31 Step 4) and ammonium chloride (56 mg, 1.05 mmol) in dichloromethane (5 mL) were added 1-ethyl-3-(3-dimethylaminopropyl)carbodiimide hydrochloride (WSC) (100 mg, 0.52 mmol), 1-hydroxybenzotriazole hydrate (HOBt) (53 mg, 0.35 mmol) and triethylamine (176 mg, 1.74 mmol) respectively. After being stirred at room temperature for 24 h, water was added to the mixture. The mixture was extracted with dichloromethane, and the extract was dried over sodium sulfate and concentrated in vacuo to afford an oil. The residual oil was purified by NH gel column chromatography (methanol/dichloromethane 1:30) followed by preparative high pressure liquid chromatography (prep. HPLC) (acetonitrile/0.01% aq. ammonia 96:4 to 4:96) to afford 75 mg (50%) of the title compound as an amorphous powder.

$^1$H-NMR (CDCl$_3$) δ 7.90 (1H, d, J=2.2 Hz), 7.53 (1H, brs), 7.11 (1H, d, J=2.2 Hz), 5.40 (1H, brs), 4.45 (1H, m), 4.26 (1H, dd, J=10.3, 5.9 Hz), 4.20 (1H, dd, J=10.3, 3.7 Hz), 3.93 (3H, s), 3.69 (1H, m), 3.52 (1H, m), 2.45-2.15 (3H, m), 2.15-1.75 (7H, m), 1.65-1.20 (4H, m).

MS (ESI) m/z: 430 (M+H)$^+$, 428 (M−H)$^-$.

Example 32

5-(trifluoromethyl)-3-(((R)-1-(trans-4-(trifluoromethyl)cyclohexanecarbonyl)pyrrolidin-2-yl)methoxy)picolinamide

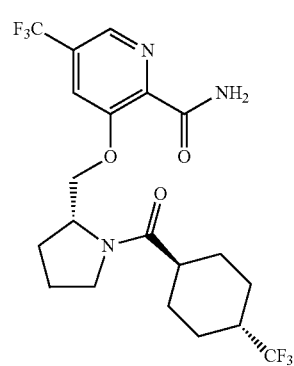

[Chem. 24]

Step 1. 3-(trifluoromethyl)-5-{[(2R)-1-{[trans-4-(trifluoromethyl)cyclohexyl]carbonyl}pyrrolidin-2-yl]methoxy}pyridine NaH (60% oil dispersant, 11 mg, 0.27 mmol) was placed on the reaction tube, and a solution of [(2R)-1-{[trans-4-(trifluoromethyl)cyclohexyl]carbonyl}pyrrolidin-2-yl]methanol (68 mg, 0.24 mmol, EXAMPLE 31 Step 1) in DMSO (2.0 mL) was added at ambient temperature. After being stirred for 15 min at room temperature, 3-bromo-5-(trifluoromethyl)pyridine (50 mg, 0.22 mmol) was added to the mixture at ambient temperature. The mixture was heated stepwise with continuous stirring, at room temperature for 19 h, at 50° C. for 3 h, at 80° C. for 15 h, and at 100° C. for 15 h. After cooling to room temperature, water was added to the mixture. The mixture was extracted with ethyl acetate twice and washed with brine. The extracts were combined and dried over sodium sulfate and concentrated in vacuo to give an oil. The residual oil was purified by silica gel preparative thin layer chromatography (TLC) (ethyl acetate/hexane 3:2) to afford 40 mg (43%) of the title compound as a colorless viscous oil.

$^1$H-NMR (CDCl$_3$) δ 8.48 (2H, brs), 7.44 (1H, brs), 4.5-4.3 (1H, m), 4.24 (1H, dd, J=8.8, 2.9 Hz), 4.14 (1H, dd, J=8.8, 6.6 Hz), 3.56 (2H, m), 2.36 (1H, tt, J=11.7, 3.7 Hz), 2.2-1.8 (8H, m), 1.7-1.4 (3H, m), 1.4-1.2 (2H, m).

MS (ESI) m/z: 425 (M+H)$^+$.

Step 2. 3-(trifluoromethyl)-5-(((R)-1-(trans-4-(trifluoromethyl)cyclohexanecarbonyl)pyrrolidin-2-yl)methoxy)pyridine 1-oxide The title compound was prepared according to the procedure described in Step 2 of EXAMPLE 29 using 3-(trifluoromethyl)-5-{[(2R)-1-{[trans-4-(trifluoromethyl)cyclohexyl]carbonyl}pyrrolidin-2-yl]methoxy}pyridine (EXAMPLE 32 Step 1) instead of (R)-tert-butyl 2-((5-chloropyridin-3-yloxy)methyl)pyrrolidine-1-carboxylate.

$^1$H-NMR (CDCl$_3$) δ 8.12 (2H, s), 7.13 (1H, s), 4.40 (1H, m), 4.24 (1H, dd, J=9.2, 2.6 Hz), 4.09 (1H, dd, J=9.2, 7.3 Hz), 3.55 (2H, m), 2.35 (1H, H, J=11.9, 3.3 Hz), 2.2-2.0 (7H, m), 2.0-1.7 (2H, m), 1.7-1.4 (2H, m), 1.4-1.2 (2H, m).
MS (ESI) m/z: 441 (M+H)⁺.

Step 3. 5-(trifluoromethyl)-3-(((R)-1-(trans-4-(trifluoromethyl)cyclohexanecarbonyl)pyrrolidin-2-yl)methoxy)picolinonitrile The title compound was prepared according to the procedure described in Step 3 of EXAMPLE 29 using 3-(trifluoromethyl)-5-(((R)-1-(trans-4-(trifluoromethyl)cyclohexanecarbonyl)pyrrolidin-2-yl)methoxy)pyridine 1-oxide (EXAMPLE 32 Step 2) instead of (R)-3-((1-(tert-butoxycarbonyl)pyrrolidin-2-yl)methoxy)-5-chloropyridine 1-oxide.
¹H-NMR (CDCl₃) δ 8.53 (1H, s), 7.7 (1H, s), 4.50 (1H, dd, J=8.8, 5.1 Hz), 4.44 (1H, m), 4.27 (1H, dd, J=8.8, 2.2 Hz), 3.70 (1H, m), 3.59 (1H, m), 2.5-2.2 (2H, m), 2.2-2.0 (6H, m), 2.0-1.8 (2H, m), 1.7-1.2 (4H, m).
MS (ESI) m/z: 450 (M+H)⁺.

Step 4. 5-(trifluoromethyl)-3-(((R)-1-(trans-4-(trifluoromethyl)cyclohexanecarbonyl)pyrrolidin-2-yl)methoxy)picolinamide The title compound was prepared according to the procedure described in Step 2 of EXAMPLE 1 using 5-(trifluoromethyl)-3-(((R)-(trans-4-(trifluoromethyl)cyclohexanecarbonyl)pyrrolidin-2-yl)methoxy)picolinonitrile (EXAMPLE 32 Step 3) instead of (R)-tert-butyl 2-((2-cyanopyridin-3-yloxy)methyl)pyrrolidine-1-carboxylate with preparative HPLC purification.
¹H-NMR (CDCl₃) δ 8.44 (1H, s), 7.67 (1H, s), 7.56 (1H, brs), 5.61 (1H, brs), 4.49 (1H, m), 4.37 (1H, dd, J=9.5, 4.4 Hz), 4.21 (1H, dd, J=9.5, 3.6 Hz), 3.72 (1H, m), 3.56 (1H, m), 2.5-2.3 (2H, m), 2.2-1.8 (8H, m), 1.7-1.2 (4H, m).
MS (ESI) m/z: 468 (M+H)⁺, 466 (M−H)⁻.
HPLC Retention time: 2.80 min (Method B).

Example 33

N-(2-hydroxyethyl)-3-(((R)-1-(trans-4-(trifluoromethyl)cyclohexanecarbonyl)pyrrolidin-2-yl)methoxy)picolinamide

[Chem. 25]

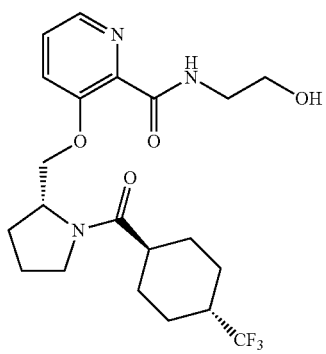

Step 1. (R)-ethyl 3-((1-(tert-butoxycarbonyl)pyrrolidin-2-yl)methoxy)picolinate The title compound was prepared according to the procedure described in Step 1 of EXAMPLE 29 using ethyl 3-hydroxypicolinate instead of 5-chloropyridin-3-ol.
MS (ESI) m/z: 351 (M+H)⁺.

Step 2. (R)-3-((1-(tert-butoxycarbonyl)pyrrolidin-2-yl)methoxy)picolinic acid The title compound was prepared according to the procedure described in Step 4 of EXAMPLE 31 using (R)-ethyl 3-((1-(tert-butoxycarbonyl)pyrrolidin-2-yl)methoxy)picolinate (EXAMPLE 33 Step 1) in stead of ethyl 5-methoxy-3-(((R)-1-(trans-4-(trifluoromethyl)cyclohexanecarbonyl)pyrrolidin-2-yl)methoxy)picolinate.
MS (ESI) m/z: 323 (M+H)⁺, 321 (M−H)⁻.

Step 3. (R)-tert-butyl 2-((2-(2-hydroxyethylcarbamoyl)pyridin-3-yloxy)methyl)pyrrolidine-1-carboxylate The title compound was prepared according to the procedure described in Step 5 of EXAMPLE 31 from (R)-3-((1-(tert-butoxycarbonyl)pyrrolidin-2-yl)methoxy)picolinic acid (EXAMPLE 33 Step 2) using ethanolamine instead of ammonium chloride.
¹H-NMR (CDCl₃) δ 8.30-7.90 (2H, m), 7.70-7.25 (2H, m), 4.40-3.75 (5H, m), 3.70-3.50 (2H, m), 3.45-3.25 (2H, m), 2.20-1.70 (4H, m), 1.45 (9H, s). A signal due to OH was not observed.
MS (ESI) m/z: 366 (M+H)⁺, 364 (M−H)⁻

Step 4. (R)—N-(2-hydroxyethyl)-3-(pyrolidin-2-ylmethoxy)picolinamide dihydrochloride (R)-tert-butyl 2-((2-(2-hydroxyethylcarbamoyl)pyridin-3-yloxy)methyl)pyrrolidine-1-carboxylate (330 mg, 0.90 mmol, EXAMPLE 33 Step 3) was dissolved in 10% hydrogen chloride in methanol (8 mL) at room temperature. After being stirred at room temperature for 4 days, the volatile was evaporated to afford 304 mg (quant.) of the title compound that was used directly in the next step without further purification.
¹H-NMR (DMSO-d6) δ 9.74 (1H, brs), 9.33 (1H, brs), 8.68 (1H, m), 831 (1H, d, J=5.1 Hz), 7.87 (1H, d, J=8.0 Hz), 7.68 (1H, dd, J=8.8, 4.4 Hz), 4.46 (1H, m), 4.33 (1H, m), 3.99 (1H, brs), 3.60-3.48 (2H, m), 3.45-3.30 (2H, m), 3.30-3.15 (2H, m), 2.25-1.75 (6H, m).
MS (ESI) m/z: 266 (M+H)⁺.

Step 5. N-(2-hydroxyethyl)-3-(((R)-1-(trans-4-(trifluoromethyl)cyclohexanecarbonyl)pyrrolidin-2-yl)methoxy)picolinamide The title compound was prepared according to the procedure described in Step 5 of EXAMPLE 31 using (R)—N-(2-hydroxyethyl)-3-(pyrrolidin-2-ylmethoxy)picolinamide dihydrochloride (EXAMPLE 33 Step 4) and trans-4-(trifluoromethyl)cyclohexanecarboxylic acid instead of ammonium chloride and 5-methoxy-3-(((R)-1-(trans-4-(trifluoromethyl)cyclohexanecarbonyl)pyrrolidin-2-yl)methoxy)picolinic acid.
¹H-NMR (CDCl₃) δ 8.18 (1H, d, J=4.4 Hz), 8.14 (1H, brs), 7.59 (1H, d, J=8.8 Hz), 7.38 (1H, dd, J=8.8, 4.4 Hz), 4.46 (1H, m), 4.25 (1H, dd, J=10.2, 3.7 Hz), 4.17 (1H, dd, J=10.2, 5.9 Hz), 3.84 (2H, brs), 3.75-3.45 (4H, m), 3.35 (1H, brs), 2.45-2.15 (2H, m), 2.15-1.70 (8H, m), 1.65-1.20 (4H, m).
MS (ESI) m/z: 444 (M+H)⁺, 442 (M−H)⁻.
HPLC Retention time: 0.65 min (Method A).

Example 34

N-(4H-1,2,4-triazol-3-yl)-3-(((R)-1-(trans-4-(trifluoromethyl)cyclohexanecarbonyl)pyrrolidin-2-yl)methoxy)picolinamide

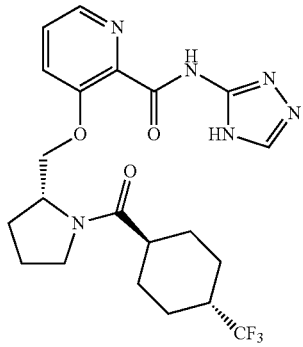

[Chem. 26]

Step 1. (R)-ethyl 3-(pyrrolidin-2-ylmethoxy)picolinate bis(trifluoroacetic acid) salt To a solution of (R)-ethyl 3-((1-(tert-butoxycarbonyl)pyrrolidin-2-yl)methoxy)picolinate (1.00 g, 285 mmol, EXAMPLE 33 Step 1) in dichloromethane (10 mL) was added trifluoroacetic acid (3 mL) at room temperature. After being stirred at room temperature for 8 h, the volatile was evaporated to afford 1.36 g (quant.) of the title compound that was used directly in the next step without further purification.
MS (ESI) m/z: 251 (M+H)$^+$.

Step 2. ethyl 3-(((R)-1-(trans-4-(trifluoromethyl)cyclohexanecarbonyl)pyrrolidin-2-yl)methoxy)picolinate The title compound was prepared according to the procedure described in Step 5 of EXAMPLE 31 using (R)-ethyl 3-(pyrrolidin-2-ylmethoxy)picolinate bis(trifluoroactetic acid) salt (EXAMPLE 34 Step 1) and trans-4-(trifluoromethyl)cyclohexanecarboxylic acid instead of ammonium chloride and 5-methoxy-3-(((R)-1-(trans-4-(trifluoromethyl)cyclohexanecarbonyl)pyrrolidin-2-yl)methoxy)picolinic acid.
$^1$H-NMR (CDCl$_3$) δ 8.25 (1H, dd, J=4.4, 1.5 Hz), 7.56 (1H, dd, J=8.8, 1.5 Hz), 7.38 (1H, dd, J=8.8, 4.4 Hz), 4.43 (2H, q, J=7.3 Hz), 4.43 (1H, m), 4.30-4.18 (2H, m), 3.70-3.40 (2H, m), 2.50-1.75 (10H, m), 1.63-1.20 (4H, m), 1.42 (3H, t, J=7.3 Hz).
MS (ESI) m/z: 429 (M+N)$^+$.

Step 3. 3-(((R)-1-(trans-4-(trifluoromethyl)cyclohexanecarbonyl)pyrrolidin-2-yl)methoxy)picolinic acid The title compound was prepared according to the procedure described in Step 4 of EXAMPLE 31 using ethyl 3-(((R)-1-(trans-4-(trifluoromethyl)cyclohexanecarbonyl)pyrrolidin-2-yl)methoxy)picolinate (EXAMPLE 34 Step 2) instead of ethyl 5-methoxy-3-(((R)-1-(trans-4-(trifluoromethyl)cyclohexanecarbonyl)pyrrolidin-2-yl)methoxy)picolinic acid.

$^1$H-NMR (CDCl$_3$) δ 8.18 (1H, d, J=4.4 Hz), 7.70 (1H, d, J=8.8 Hz), 7.56 (1H, dd, J=8.8, 4.4 Hz), 4.55-4.35 (2H, m), 4.22 (1H, m), 3.77 (1H, m), 3.54 (1H, m), 2.50-2.30 (2H, m), 2.22 (1H, m), 2.15-1.80 (6H, m), 1.70-1.20 (5H, m). A signal due to COOH was not observed.
MS (ESI) m/z: 401 (M+H)$^+$, 399 (M−H)$^-$.

Step 4. N-(4H-1,2,4-triazol-3-yl)-3-(((R)-1-(trans-4-(trifluoromethyl)cyclohexanecarbonyl)pyrrolidin-2-yl)methoxy)picolinamide To a solution of 3-(((R)-1-(trans-4-(trifluoromethyl)cyclohexanecarbonyl)pyrrolidin-2-yl)methoxy)picolinic acid (30 mg, 0.08 mmol, EXAMPLE 34 Step 3) in dichloromethane (1 mL) were added oxalyl chloride (33 microL, 0.38 mmol) and a catalytic amount of N,N-dimethylformamide at room temperature. After being stirred at room temperature for 30 min, the volatile was removed under reduced pressure. The resulting residue was dissolved in toluene (1 mL). Triethyl amine (10 microL, 0.08 mmol) and 4H-1,2,4-triazol-3-amine (8 mg, 0.09 mmol) were added to the mixture. After being refluxed for 15 h, the volatile was removed by evaporation. The residual material was dissolved in dichloromethane. The organic layer was washed with aq. sodium bicarbonate and concentrated in vacuo to afford the title compound as a brown oil. The crude product was purified by preparative HPLC.
MS (ESI) m/z: 467 (WEFT)$^+$, 465 (M−H)$^-$.
HPLC Retention time: 1.41 min (Method C).

Example 35-59

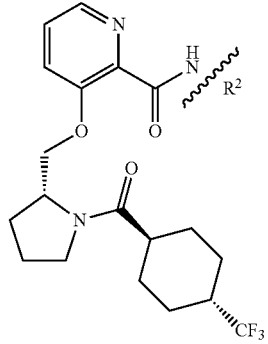

[Chem. 27]

The following examples, EXAMPLE 35-59, were prepared according to the following described procedure, utilizing the carboxylic acid, 3-(((R)-1-(trans-4-(trifluoromethyl)cyclohexanecarbonyl)pyrrolidin-2-yl)methoxy)picolinic acid (EXAMPLE 34 Step 3) with preparative HPLC purification.

The following examples, EXAMPLE 35-44, were prepared according to the procedure similar to that described in the Step 5 of the EXAMPLE 31, using the appropriate precursor of amine, R$^2$—NH$_2$.

The following examples, EXAMPLE 45-50, were prepared according to the procedure similar to that described in the Step 1 of the EXAMPLE 3, using the appropriate precursor of amine, R$^2$—NH$_2$.

The following examples, EXAMPLE 51-59, were prepared according to the procedure similar to that described in the Step 4 of the EXAMPLE 1, using the appropriate precursor of amine, R$^2$—NH$_2$.

TABLE 7-1

| EXAMPLES | R² | Chemical Name | HPLC Gradient Method | HPLC Retention Time (min.) | MS (ESI): m/z (M + H)+ |
|---|---|---|---|---|---|
| 35 | | methyl 2-(3-(((R)-1-(trans-4-(trifluoromethyl)cyclohexanecarbonyl)pyrrolidin-2-yl)methoxy)picolinamido)acetate | Method C | 1.55 | 472 |
| 36 | | N-(2-morpholinoethyl)-3-(((R)-1-(trans-4-(trifluoromethyl)cyclohexanecarbonyl)pyrrolidin-2-yl)methoxy)picolinamide | Method C | 1.47 | 513 |
| 37 | | N-(2-methoxyethyl)-3-(((R)-1-(trans-4-(trifluoromethyl)cyclohexanecarbonyl)pyrrolidin-2-yl)methoxy)picolinamide | Method C | 1.53 | 458 |
| 38 | | N-(2-(pyrrolidin-1-yl)ethyl)-3-(((R)-1-(trans-4-(trifluoromethyl)cyclohexanecarbonyl)pyrrolidin-2-yl)methoxy)picolinamide | Method C | 1.39 | 497 |
| 39 | | N-((1-hydroxycyclohexyl)methyl)-3-(((R)-1-(trans-4-(trifluoromethyl)cyclohexanecarbonyl)pyrrolidin-2-yl)methoxy)picolinamide | Method C | 1.66 | 512 |
| 40 | | N-(pyridin-2-ylmethyl)-3-(((R)-1-(trans-4-(trifluoromethyl)cyclohexanecarbonyl)pyrrolidin-2-yl)methoxy)picolinamide | Method C | 1.55 | 491 |

TABLE 7-2

| EXAMPLES | R² | Chemical Name | HPLC Gradient Method | HPLC Retention Time (min.) | MS (ESI): m/z (M + H)+ |
|---|---|---|---|---|---|
| 41 | | N-benzyl-3-(((R)-1-(trans-4-(trifluoromethyl)cyclohexanecarbonyl)pyrrolidin-2-yl)methoxy)picolinamide | Method C | 1.74 | 490 |
| 42 | | N-((R)-2-hydroxy-1-phenylethyl)-3-(((R)-(trans-4-(trifluoromethyl)cyclohexanecarbonyl)pyrrolidin-2-yl)methoxy)picolinamide | Method B | 3.37 | 520 |
| 43 | | N-((S)-2-hydroxy-1-phenylethyl)-3-(((R)-1-(trans-4-(trifluoromethyl)cyclohexanecarbonyl)pyrrolidin-2-yl)methoxy)picolinamide | Method B | 3.37 | 520 |

TABLE 7-2-continued

| EXAMPLES | R² | Chemical Name | HPLC Gradient Method | HPLC Retention Time (min.) | MS (ESI): m/z (M + H)+ |
|---|---|---|---|---|---|
| 44 | | N-phenyl-3-(((R)-1-(trans-4-(trifluoromethyl)cyclohexane-carbonyl)pyrrolidin-2-yl)methoxy)picolinamide | Method C | 1.80 | 476 |
| 45 | | N-(4-methyloxazol-2-yl)-3-(((R)-1-(trans-4-(trifluoromethyl)cyclohexanecarbonyl)pyrrolidin-2-yl)methoxy)picolinamide | Method C | 1.60 | 481 |
| 46 | | N-(oxazol-2-yl)-3-(((R)-1-(trans-4-(trifluoromethyl)cyclohexane-carbonyl)pyrrolidin-2-yl)methoxy)picolinamide | Method C | 1.54 | 467 |

TABLE 7-3

| EXAMPLES | R² | Chemical Name | HPLC Gradient Method | HPLC Retention Time (min.) | MS (ESI): m/z (M + H)+ |
|---|---|---|---|---|---|
| 47 | | N-(1,2,4-thiadiazol-5-yl)-3-(((R)-1-(trans-4-(trifluoromethyl)cyclohexanecarbonyl)pyrrolidin-2-yl)methoxy)picolinamide | Method C | 1.68 | 484 |
| 48 | | N-((tetrahydro-2H-pyran-4-yl)methyl)-3-(((R)-1-(trans-4-(trifluoromethyl)cyclohexanecarbonyl)pyrrolidin-2-yl)methoxy)picolinamide | Method C | 1.54 | 498 |
| 49 | | N-(tetrahydro-2H-pyran-4-yl)-3-(((R)-1-(trans-4-(trifluoromethyl)cyclohexanecarbonyl)pyrrolidin-2-yl)methoxy)picolinamide | Method C | 1.51 | 484 |
| 50 | | N-(1H-1,2,4-triazol-5-yl)-3-(((R)-1-(trans-4-(trifluoromethyl)cyclohexanecarbonyl)pyrrolidin-2-yl)methoxy)picolinamide | Method C | 1.35 | 481 |
| 51 | | N-(isoxazol-5-yl)-3-(((R)-1-(trans-4-(trifluoromethyl)cyclohexanecarbonyl)pyrrolidin-2-yl)methoxy)picolinamide | Method B | 2.84 | 467 |
| 52 | | N-(1,5-dimethyl-1H-pyrazol-3-yl)-3-(((R)-1-(trans-4-(trifluoromethyl)cyclohexanecarbonyl)pyrrolidin-2-yl)methoxy)picolinamide | Method C | 1.60 | 494 |

TABLE 7-3-continued

| EXAMPLES | R² | Chemical Name | HPLC Gradient Method | HPLC Retention Time (min.) | MS (ESI): m/z (M + H)+ |
|---|---|---|---|---|---|
| 53 | | N-(1-methyl-1H-pyrazol-3-yl)-3-(((R)-1-(trans-4-(trifluoromethyl)cyclohexanecarbonyl)pyrrolidin-2-yl)methoxy)picolinamide | Method C | 1.54 | 480 |

TABLE 7-4

| EXAMPLES | R² | Chemical Name | HPLC Gradient Method | HPLC Retention Time (min.) | MS (ESI): m/z (M + H)+ |
|---|---|---|---|---|---|
| 54 | | N-(isoxazol-3-yl)-3-(((R)-1-(trans-4-(trifluoromethyl)cyclohexanecarbonyl)pyrrolidin-2-yl)methoxy)picolinamide | Method C | 1.65 | 467 |
| 55 | | N-(1-isopropyl-1H-pyrazol-5-yl)-3-(((R)-1-(trans-4-(trifluoromethyl)cyclohexanecarbonyl)pyrrolidin-2-yl)methoxy)picolinamide | Method C | 1.66 | 508 |
| 56 | | N-(pyrimidin-4-yl)-3-(((R)-1-(trans-4-(trifluoromethyl)cyclohexanecarbonyl)pyrrolidin-2-yl)methoxy)picolinamide | Method E | 2.60 | 478 |
| 57 | | N-(3-methylisoxazol-5-yl)-3-(((R)-1-(trans-4-(trifluoromethyl)cyclohexanecarbonyl)pyrrolidin-2-yl)methoxy)picolinamide | Method C | 1.71 | 481 |
| 58 | | N-(5-methylisoxazol-3-yl)-3-(((R)-1-(trans-4-(trifluoromethyl)cyclohexanecarbonyl)pyrrolidin-2-yl)methoxy)picolinamide | Method C | 1.71 | 481 |
| 59 | | N-(1-benzyl-1H-pyrazol-3-yl)-3-(((R)-1-(trans-4-(trifluoromethyl)cyclohexanecarbonyl)pyrrolidin-2-yl)methoxy)picolinamide | Method C | 1.80 | 556 |

Example 60

N-(1-methyl-1H-pyrazol-3-yl)-3-(((S)-1-(trans-4-(trifluoromethyl)cyclohexanecarbonyl)pyrrolidin-2-yl)methoxy)picolinamide

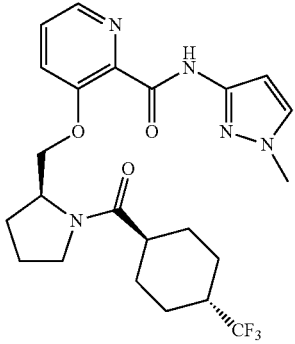

[Chem. 28]

Step 1. [(2S)-1-{[trans-4-(trifluoromethyl)cyclohexyl]carbonyl}pyrrolidin-2-yl]methanol The title compound was prepared according to the procedure described in Step 1 of EXAMPLE 31 using (S)-pyrrolidin-2-ylmethanol instead of (R)-pyrrolidin-2-ylmethanol.
$^1$H-NMR (CDCl$_3$) δ 5.04 (1H, dd, J=6.7, 2.2 Hz), 4.24 (1H, m), 3.69-3.40 (4H, m), 2.37 (1H, tt, J=11.7, 2.9 Hz,), 1.33-2.17 (13H, m).
MS (ESI) m/z: 280 (M+H)$^+$.

Step 2. ethyl 3-(((S)-1-(trans-4-(trifluoromethyl)cyclohexanecarbonyl)pyrrolidin-2-yl)methoxy)picolinate The title compound was prepared according to the procedure described in Step 1 of EXAMPLE 29 using [(2S)-1-{[trans-4-(trifluoromethyl)cyclohexyl]carbonyl}pyrrolidin-2-yl]methanol (EXAMPLE 60 Step 1) and ethyl 3-hydroxypicolinate instead of (R)-tert-butyl 2-(hydroxymethyl)pyrrolidine-1-carboxylate and 5-chloropyridin-3-ol.
MS (ESI) m/z: 429 (M+H)$^+$.

Step 3. 3-(((S)-1-(trans-4-(trifluoromethyl)cyclohexanecarbonyl)pyrrolidin-2-yl)methoxy)picolinic acid The title compound was prepared according to the procedure described in Step 4 of EXAMPLE 31 using ethyl 3-(((S)-1-(trans-4-(trifluoromethyl)cyclohexanecarbonyl)pyrrolidin-2-yl)methoxy)picolinate (EXAMPLE 60 Step 2) instead of ethyl 5-methoxy-3-(((R)-1-(trans-4-(trifluoromethyl)cyclohexanecarbonyl)pyrrolidin-2-yl)methoxy)picolinate.
$^1$H-NMR (CDCl$_3$) δ 8.17 (1H, d, J=4.4 Hz), 7.70 (1H, d, J=8.8 Hz), 7.55 (1H, dd, J=8.8, 4.4 Hz), 4.47-4.38 (2H, m), 4.23 (1H, m), 3.77 (1H, m), 3.54 (1H, m), 2.50-2.30 (2H, m), 2.22 (1H, m), 2.10-1.80 (6H, m), 1.70-1.25 (5H, m). A signal due to COOH was not observed.
MS (ESI) m/z: 401 (M+H)$^+$, 399 (M−H)$^−$.

Step 4. N-(1-methyl-1H-pyrazol-3-yl)-3-(((S)-1-(trans-4-(trifluoromethyl)cyclohexanecarbonyl)pyrrolidin-2-yl)methoxy)picolinamide The title compound was prepared according to the procedure described in Step 4 of Example 1 using 3-(((S)-1-(trans-4-(trifluoromethyl)cyclohexanecarbonyl)pyrrolidin-2-yl)methoxy)picolinic acid (Example 60 step 3) and 1-methyl-1H-pyrazol-3-amine instead of cis-4-(trifluoromethyl)cyclohexanecarboxylic acid and (R)-3-(pyrrolidin-2-ylmethoxy)picolinamide dihydrochloride with preparative HPLC purification.
MS (ESI) m/z: 480 (M+H)$^+$.
HPLC Retention time: 1.56 min (Method C).

Example 61

N-(oxazol-2-yl)-3-(((S)-1-(trans-4-(trifluoromethyl)cyclohexanecarbonyl)pyrrolidin-2-yl)methoxy)picolinamide

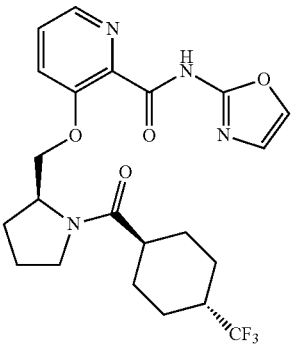

[Chem. 29]

The title compound was prepared according to the procedure described in Step 1 of Example 3 using 3-(((S)-1-(trans-4-(trifluoromethyl)cyclohexanecarbonyl)pyrrolidin-2-yl)methoxy)picolinic acid (Example 60 step 3) and oxazol-2-amine instead of indole-2-carboxylic acid and (R)-3-(pyrrolidin-2-ylmethoxy)picolinamide dihydrochloride with preparative HPLC purification.
MS (ESI) m/z: 467 (M+H)$^+$, 465 (M−H)$^+$.
HPLC Retention time: 1.54 min (Method C).

Example 62

N-(oxazol-2-yl)-3-(((S)-1-(cis-4-(trifluoromethyl)cyclohexanecarbonyl)pyrrolidin-2-yl)methoxy)picolinamide

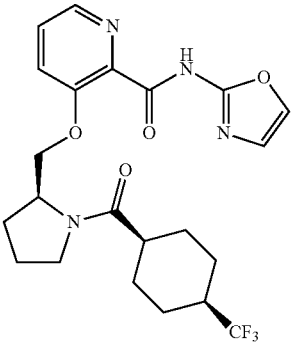

[Chem. 30]

The title compound was prepared according to the procedure described in EXAMPLE 61 using cis-4-(trifluoromethyl)cyclohexanecarboxylic acid instead of trans-4-(trifluoromethyl)cyclohexanecarboxylic acid with preparative HPLC purification.

MS (ESI) m/z: 467 (M+H)⁺, 465 (M−H)⁺.

HPLC Retention time: 1.55 min (Method C).

Example 63

N-(oxazol-2-yl)-3-(((R)-1-(cis-4-(trifluoromethyl)cyclohexanecarbonyl)pyrrolidin-2-yl)methoxy)picolinamide

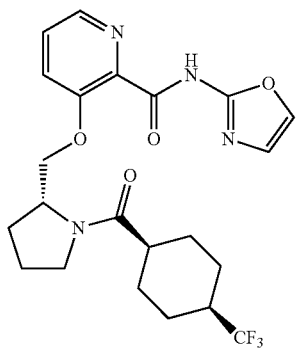

[Chem. 31]

The title compound was prepared according to the procedure described in EXAMPLE 46 using cis-4-(trifluoromethyl)cyclohexanecarboxylic acid instead of trans-4-(trifluoromethyl)cyclohexanecarboxylic acid with preparative HPLC purification.

MS (ESI) m/z: 467 (M+H)⁺, 465 (M−H)⁺.

HPLC Retention time: 1.55 min (Method C).

Example 64

(R)-3-((1-(2-(4,4-difluorocyclohexyl)acetyl)pyrrolidin-2-yl)methoxy)-N-(oxazol-2-yl)picolinamide

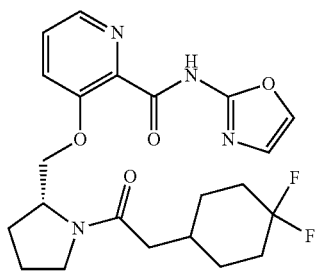

[Chem. 32]

Step 1. (R)-tert-butyl 2-((2-(oxazol-2-ylcarbamoyl)pyridin-3-yloxy)methyl)pyrrolidine-1-carboxylate The title compound was prepared according to the procedure described in Step 5 of EXAMPLE 31 using (R)-3-((1-(tert-butoxycarbonyl)pyrrolidin-2-yl)methoxy)picolinic acid (EXAMPLE 33 Step 2) and oxazol-2-amine instead of 5-methoxy-3-(((R)-1-(trans-4-(trifluoromethyl)cyclohexanecarbonyl)pyrrolidin-2-yl)methoxy)picolinic acid and ammonium chloride.

¹H-NMR (CDCl₃) δ 10.8 (1H, brs), 8.24 (1H, s), 7.59 (1H, m), 7.53-7.40 (2H, m), 7.09 (1H, s), 4.45-3.80 (3H, m), 3.40 (2H, s), 2.45-1.70 (4H, m), 1.44 (9H, s).

MS (ESI) m/z: 389 (M+H)⁺, 387 (M−H)⁻.

Step 2. (R)—N-(oxazol-2-yl)-3-(pyrrolidin-2-ylmethoxy)picolinamide dihydrochloride The title compound was prepared according to the procedure described in Step 4 of EXAMPLE 33 using (R)-tert-butyl 2-((2-(oxazol-2-ylcarbamoyl)pyridin-3-yloxy)methyl)pyrrolidine-1-carboxylate (EXAMPLE 64 Step 1) instead of (R)-tert-butyl 2-((2-(2-hydroxyethylcarbamoyl)pyridin-3-yloxy)methyl)pyrrolidine-1-carboxylate.

¹H-NMR (DMSO-d6) δ 9.79 (1H, brs), 9.24 (1H, brs), 8.29 (1H, d, J=4.4 Hz), 7.97 (1H, s), 7.75 (1H, d, J=8.1 Hz), 7.63 (1H, dd, J=8.8, 4.4 Hz), 7.20 (1H, s), 4.50-4.25 (2H, m), 3.96 (1H, m), 3.25-3.10 (2H, m), 2.25-1.75 (4H, m).

MS (ESI) m/z: 289 (M+H)⁺.

Step 3. (R)-3-((1-(2-(4,4-difluorocyclohexyl)acetyl)pyrrolidin-2-yl)methoxy)-N-(oxazol-2-yl)picolinamide The title compound was prepared according to the procedure described in Step 5 of EXAMPLE 31 using (R)—N-(oxazol-2-yl)-3-(pyrrolidin-2-ylmethoxy)picolinamide dihydrochloride (EXAMPLE 64 Step 2) and 2-(4,4-difluorocyclohexyl)acetic acid instead of ammonium chloride and 5-methoxy-3-(((R)-1-(trans-4-(trifluoromethyl)cyclohexanecarbonyl)pyrrolidin-2-yl)methoxy)picolinic acid with preparative HPLC purification.

MS (ESI) m/z: 449 (M+H)⁺, 447 (M−H)⁻.

HPLC Retention time: 2.45 min (Method B).

Example 65

(R)-3-((1-(5-cyclopropylisoxazole-3-carbonyl)pyrrolidin-2-yl)methoxy)-N-(oxazol-3-yl)picolinamide

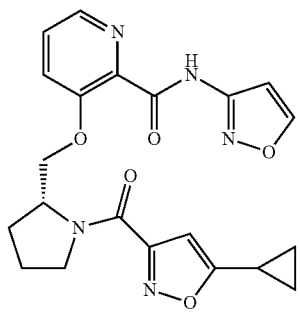

[Chem. 33]

Step 1. (R)-ethyl 3-((1-(5-cyclopropylisoxazole-3-carbonyl)pyrrolidin-2-yl)methoxy)picolinate The title compound was prepared according to the procedure described in Step 5 of EXAMPLE 31 using (R)-ethyl 3-(pyrrolidin-2-ylmethoxy)picolinate bis(trifuluoroacetic acid) salt (EXAMPLE 34 Step 1) and 5-cyclopropylisoxazole-3-carboxylic acid instead of ammonium chloride and 5-methoxy-3-(((R)-1-(trans-4-(trifluoromethyl)cyclohexanecarbonyl)pyrrolidin-2-yl)methoxy)picolinic acid.

MS (ESI) m/z: 386 (M+H)⁺.

Step 2. (R)-3-((1-(5-cyclopropylisoxazole-3-carbonyl)pyrrolidin-2-yl)methoxy)picolinic acid The title compound was prepared according to the procedure described in Step 4 of EXAMPLE 31 using (R)-ethyl 3-((1-(5-cyclopropylisoxazole-3-carbonyl)pyrrolidin-2-yl)methoxy)picolinate (EXAMPLE 65 Step 1) instead of ethyl 5-methoxy-3-(((R)-1-(trans-4-(trifluoromethyl)cyclohexanecarbonyl)pyrrolidin-2-yl)methoxy)picolinate.
MS (ESI) m/z: 358 (M+H)⁺, 356 (M−H)⁻.

Step 3. (R)-3-((1-(5-cyclopropylisoxazole-3-carbonyl)pyrrolidin-2-yl)methoxy)-N-(isoxazol-3-yl)picolinamide The title compound was prepared according to the procedure described in Step 4 of EXAMPLE 1 using (R)-3-((1-(5-cyclopropylisoxazole-3-carbonyl)pyrrolidin-2-yl)methoxy)picolinic acid (EXAMPLE 65 Step 2) and isoxazol-3-amine instead of cis-4-(trifluoromethyl)cyclohexanecarboxylic acid and (R)-3-(pyrrolidin-2-ylmethoxy)picolinamide dihydrochloride with preparative HPLC purification.
MS (ESI) m/z: 424 (WEFT)⁺, 422 (M−H)⁻.
HPLC Retention time: 1.52 min (Method C).

Example 66

(R)-3-((1-(2-(4,4-difluorocyclohexyl)acetyl)pyrrolidin-2-yl)methoxy)-N-(isoxazol-3-yl)picolinamide

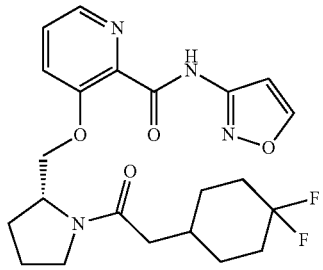

[Chem. 34]

Step 1. (R)-ethyl 3-((1-(2-(4,4-difluorocyclohexyl)acetyl)pyrrolidin-2-yl)methoxy)picolinate The title compound was prepared according to the procedure described in Step 5 of EXAMPLE 31 using (R)-ethyl 3-(pyrrolidin-2-ylmethoxy)picolinate bis(trifuluoroacetic acid) salt (EXAMPLE 34 Step 1) and 2-(4,4-difluorocyclohexyl)acetic acid instead of ammonium chloride and 5-methoxy-3-(((R)-1-(trans-4-(trifluoromethyl)cyclohexanecarbonyl)pyrrolidin-2-yl)methoxy)picolinic acid.
¹H-NMR (CDCl₃) δ 8.25 (1H, d, J=5.1 Hz), 7.54 (1H, d, J=8.8 Hz), 7.38 (1H, dd, J=8.8, 5.1 Hz), 4.43 (2H, q, J=7.3 Hz), 4.24 (2H, d, J=4.4 Hz), 3.65-3.35 (3H, m), 2.50-1.10 (15H, m), 1.42 (3H, t, J=6.6 Hz).
MS (ESI) m/z: 411 (M+H)⁺.

Step 2. (R)-3-((1-(2-(4,4-difluorocyclohexyl)acetyl)pyrrolidin-2-yl)methoxy)picolinic acid The title compound was prepared according to the procedure described in Step 4 of EXAMPLE 31 using (R)-ethyl 3-((1-(2-(4,4-difluorocyclohexyl)acetyl)pyrrolidin-2-yl)methoxy)picolinate (EXAMPLE 66 Step 1) instead of ethyl 5-methoxy-3-(((R)-1-(trans-4-(trifluoromethyl)cyclohexanecarbonyl)pyrrolidin-2-yl)methoxy)picolinate.
MS (ESI) m/z: 383 (M+H)⁺, 381 (M−H)⁻.

Step 3. (R)-3-((1-(2-(4,4-difluorocyclohexyl)acetyl)pyrrolidin-2-yl)methoxy)-N-(isoxazol-3-yl)picolinamide The title compound was prepared according to the procedure described in Step 4 of EXAMPLE 1 using (R)-3-((1-(2-(4,4-difluorocyclohexyl)acetyl)pyrrolidin-2-yl)methoxy)picolinic acid (EXAMPLE 66 Step 2) and isoxazol-3-amine instead of cis-4-(trifluoromethyl)cyclohexanecarboxylic acid and (R)-3-(pyrrolidin-2-ylmethoxy)picolinamide dihydrochloride with preparative HPLC purification.
MS (ESI) m/z: 449 (M+H)⁺, 447 (M−H)⁻.
HPLC Retention time: 2.65 min (Method B).

Example 67

(R)—N-(2-amino-2-oxoethyl)-3-((1-(3-(trifluoromethyl)benzoyl)pyrrolidin-2-yl)methoxy)picolinamide

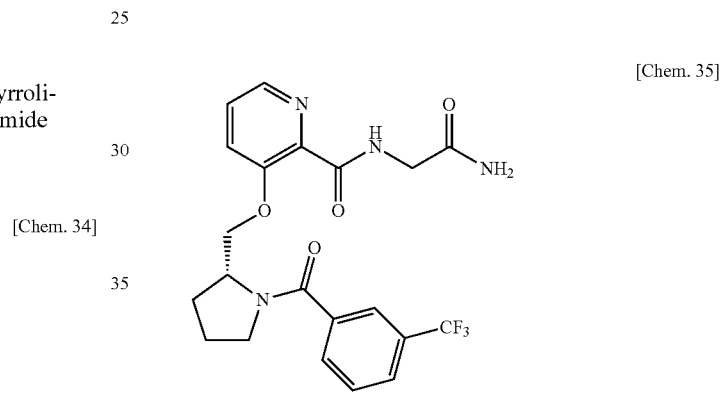

[Chem. 35]

Step 1. (R)-ethyl 3-((1-(3-(trifluoromethyl)benzoyl)pyrrolidin-2-yl)methoxy)picolinate The title compound was prepared according to the procedure described in Step 5 of EXAMPLE 31 using (R)-ethyl 3-(pyrrolidin-2-ylmethoxy)picolinate bis(trifuluoroacetic acid) salt (EXAMPLE 34 Step 1) and 3-trifluoromethylbenzoic acid instead of ammonium chloride and 5-methoxy-3-(((R)-1-(trans-4-(trifluoromethyl)cyclohexanecarbonyl)pyrrolidin-2-yl)methoxy)picolinic acid.
¹H-NMR (CDCl₃) δ 8.28 (1H, dd, J=4.4, 1.5 Hz), 7.80 (1H, s), 7.73-7.63 (2H, m), 7.58-7.45 (2H, m), 7.38 (1H, dd, J=8.8, 4.4 Hz), 4.65-4.55 (2H, m), 4.46 (2H, q, J=7.3 Hz), 4.29 (1H, m), 3.65 (1H, m), 3.44 (1H, m), 2.33-2.01 (3H, m), 1.84 (1H, m), 1.45 (3H, t, J=7.3 Hz).
MS (ESI) m/z: 423 (M+H)⁺.

Step 2. (R)-3-((1-(3-(trifluoromethyl)benzoyl)pyrrolidin-2-yl)methoxy)picolinic acid The title compound was prepared according to the procedure described in Step 4 of EXAMPLE 31 using (R)-ethyl 3-((1-(3-(trifluoromethyl)benzoyl)pyrrolidin-2-yl)methoxy)picolinate (EXAMPLE 67 Step 1) instead of ethyl 5-methoxy-3-(((R)-1-(trans-4-(trifluoromethyl)cyclohexanecarbonyl)pyrrolidin-2-yl)methoxy)picolinate.

¹H-NMR (CDCl₃) δ 8.19 (1H, d, J=4.4 Hz), 7.80 (1H, s), 7.76-7.64 (2H, m), 7.63-7.48 (3H, m), 4.76 (1H, dd, J=9.5, 4.4 Hz), 4.66 (1H, m), 4.28 (1H, d, J=9.5 Hz), 3.92 (1H, m), 3.46 (1H, m), 2.45-2.11 (3H, m), 1.82 (1H, m). A signal due to COON was not observed.

MS (ESI) m/z: 395 (M+H)⁺, 393 (M−H)⁻.

Step 3. (R)—N-(2-amino-2-oxoethyl)-3-((1-(3-(trifluoromethyl)benzoyl)pyrrolidin-2-yl)methoxy)picolinamide The title compound was prepared according to the procedure described in Step 5 of EXAMPLE 31 using 2-aminoacetamide and (R)-3-((1-(3-(trifluoromethyl)benzoyl)pyrrolidin-2-yl)methoxy)picolinic acid (EXAMPLE 67 Step 2) instead of ammonium chloride and 5-methoxy-3-(((R)-1-(trans-4-(trifluoromethyl)cyclohexanecarbonyl)pyrrolidin-2-yl)methoxy)picolinic acid with preparative HPLC purification.

MS (ESI) m/z: 451 (M+H)⁺, 449 (M−H)⁻.

HPLC Retention time: 1.32 min (Method C).

Example 68 to 74

[Chem. 36]

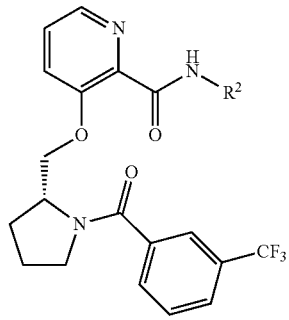

The following examples, EXAMPLE 68-74, were prepared according to the procedure similar to that described in the Step 5 of the EXAMPLE 31, using (R)-3-((1-(3-(trifluoromethyl)benzoyl)pyrrolidin-2-yl)methoxy)picolinic acid (EXAMPLE 67 Step 2) and the appropriate precursor of amine, R²—NH₂. The following examples, EXAMPLE 68 to 74, were purified by preparative HPLC.

TABLE 8

| EXAMPLES | R² | Chemical Name | HPLC Gradient Method | HPLC Retention Time (min.) | MS (ESI): m/z (M + H)+ |
|---|---|---|---|---|---|
| 68 | | (R)-N-(2-morpholinoethyl)-3-((1-(3-(trifluoromethyl)benzoyl)pyrrolidin-2-yl)methoxy)picolinamide | Method C | 1.42 | 507 |
| 69 | | (R)-N-(2-hydroxyethyl)-3-((1-(3-(trifluoromethyl)benzoyl)pyrrolidin-2-yl)methoxy)picolinamide | Method C | 1.35 | 438 |
| 70 | | (R)-N-(2-methoxyethyl)-3-((1-(3-(trifluoromethyl)benzoyl)pyrrolidin-2-yl)methoxy)picolinamide | Method C | 1.50 | 452 |
| 71 | | ((R)-N-((1-hydroxycyclohexyl)methyl)-3-((1-(3-(trifluoromethyl)benzoyl)pyrrolidin-2-yl)methoxy)picolinamide | Method C | 1.64 | 506 |
| 72 | | (R)-N-phenyl-3-((1-(3-(trifluoromethyl)benzoyl)pyrrolidin-2-yl)methoxy)picolinamide | Method C | 1.80 | 470 |
| 73 | | (R)-N-(pyridin-2-ylmethyl)-3-((1-(3-(trifluoromethyl)benzoyl)pyrrolidin-2-yl)methoxy)picolinamide | Method C | 1.52 | 485 |
| 74 | | (R)-N-benzyl-3-((1-(3-(trifluoromethyl)benzoyl)pyrrolidin-2-yl)methoxy)picolinamide | Method C | 1.74 | 484 |

Example 75

N-(pyridin-2-yl)-3-(((R)-1-(trans-4-(trifluoromethyl)cyclohexanecarbonyl)pyrrolidin-2-yl)methoxy)picolinamide

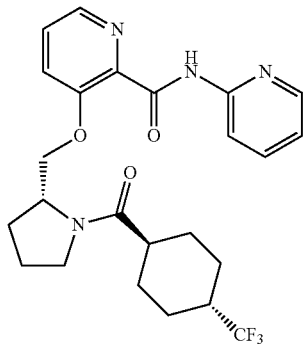

[Chem. 37]

Step 1. 3-(((R)-1-(trans-4-(trifluoromethyl)cyclohexanecarbonyl)pyrrolidin-2-yl)methoxy)picolinamide The title compound was prepared according to the procedure described in Step 5 of EXAMPLE 31 using (R)-3-(pyrrolidin-2-ylmethoxy)picolinamide dihydrochloride (EXAMPLE 1 Step 3) and trans-4-(trifluoromethyl)cyclohexanecarboxylic acid instead of ammonium chloride and 5-methoxy-3-(((R)-1-(trans-4-(trifluoromethyl)cyclohexanecarbonyl)pyrrolidin-2-yl)methoxy)picolinic acid.

$^1$H-NMR (CDCl$_3$) δ 8.20 (1H, d, J=4.4 Hz), 7.60 (1H, d, J=7.3 Hz), 7.59 (1H, s), 7.41 (1H, dd, J=8.1, 4.4 Hz), 5.58 (1H, brs), 4.44 (1H, m), 4.24 (2H, d, J=5.1 Hz), 3.70 (1H, m), 3.52 (1H, m), 2.50-1.80 (11H, m), 1.70-1.20 (3H, m).

MS (ESI) m/z: 400 (M+H)$^+$.

Step-2. N-pyridin-2-yl)-3-(((R)-1-(trans-4-(trifluoromethyl)cyclohexanecarbonyl)pyrrolidin-2-yl)methoxy)picolinamide To a stirred mixture of 3-(((R)-1-(trans-4-(trifluoromethyl)cyclohexanecarbonyl)pyrrolidin-2-yl)methoxy)picolinamide (30 mg, 0.08 mmol, EXAMPLE 75 Step 1), 4,5-Bis(diphenylphosphino)-9,9-dimethylxanthene (XANTPHOS) (3.47 mg, 6.00 micromol), cesium carbonate (0.10 g, 0.30 mmol), and tris(dibenzylideneacetone)dipalladium (Pd$_2$(dba)$_3$) (1.56 mg, 1.50 micromol) in 1,4-dioxane (2 mL) was added 2-bromopyridine (14 mg, 0.09 mmol) at room temperature. After being stirred at 120° C. for 12 h under microwave irradiation, water was added to the mixture. The mixture was extracted with ethyl acetate twice. The extracts were combined and dried over magnesium sulfate and concentrated in vacuo to afford an oil. The residual oil was purified by preparative HPLC.

MS (ESI) m/z: 477 (M+H)$^+$, 475 (M−H)$^-$.

HPLC Retention time: 1.75 min (Method C).

Example 76

N-(pyrazin-2-yl)-3-(((R)-1-(trans-4-(trifluoromethyl)cyclohexanecarbonyl)pyrrolidin-2-yl)methoxy)picolinamide

[Chem. 38]

The title compound was prepared according to the procedure described in Step 2 of EXAMPLE 75 using 2-chloropyrazine instead of 2-bromopyridine with preparative HPLC purification.

MS (ESI) m/z: 478 (M+H)$^+$.

HPLC Retention time: 1.66 min (Method C).

Example 77

N-((4-hydroxytetrahydro-2H-pyran-4-yl)methyl)-3-(aR)-1-(trans-4-(trifluoromethyl)cyclohexanecarbonyl)pyrrolidin-2-yl)methoxy)picolinamide

[Chem. 39]

Step 1. 4-(iodomethyl)tetrahydro-2H-pyran-4-ol

A mixture of trimethylsulfoxonium chloride (3.08 g, 23.73 mmol) and 2 N aq. sodium hydroxide (11.33 mL, 22.65 mmol) in tetrahydrofuran (13 mL) was heated at 50° C. for 1 h. 2.16 g (21.57 mmol) of tetrahydro-4H-pyran-4-one was added to the mixture and the mixture was stirred at 50° C. for 30 min. After cooling to room temperature, 3.56 g (23.73 mmol) of sodium iodide and 2 N hydrochloric acid (10.8 mL, 21.57 mmol) were added to the mixture. After being stirred at room temperature for 19 h, ethyl acetate was added to the mixture. The mixture was extracted with ethyl acetate three times and the extracts were combined. The extracts were dried over sodium sulfate and concentrated in vacuo to afford a beige solid. The residual solid was recrystallized from acetonitrile to afford 3.13 g (55%) of the title compound.

$^1$H NMR 3.85-3.65 (m, 4H), 3.36 (s, 2H), 1.85-1.55 (m, 4H) A signal due to OH was not observed.

MS (ESI) m/z: 243 (M+H)$^+$.

Step 2. N-((4-hydroxytetrahydro-2H-pyran-4-yl) methyl)-3-(((R)-1-(trans-4-(trifluoromethyl)cyclohexanecarbonyl)pyrrolidin-2-yl)methoxy)picolinamide To a solution of 3-(((R)-1-(trans-4-(trifluoromethyl)cyclohexanecarbonyl)pyrrolidin-2-yl)methoxy)picolinamide (105 mg, 0.263 mmol, EXAMPLE 75 Step 1) in 1-Methyl-2-pyrrolidone (5 mL) was added sodium hydride (60% oil dispersant, 16 mg, 0.394 mmol) at ambient temperature. After being stirred at room temperature for 1 h, 4-(iodomethyl)tetrahydro-2H-pyran-4-ol (76 mg, 0.315 mmol, EXAMPLE 77 Step 1) was added to the mixture. The mixture was heated at 70° C. and stirred for 3 days. After cooling to room temperature, aq. citric acid was added to the mixture. The mixture was extracted with ethyl acetate twice and washed successively with aq. sodium thiosulfate, aq. sodium bicarbonate, and brine. The extracts were combined and dried over sodium sulfate and concentrated in vacuo to afford 72 mg of crude oil. The residual oil was purified by preparative HPLC purification.

MS (ESI) m/z: 514 (M+H)$^+$.

HPLC Retention time: 1.44 min (Method C).

Example 78

(R)—N-(pyridin-2-yl)-3-((1-(3-(trifluoromethyl) benzoyl)pyrrolidin-2-yl)methoxy)picolinamide

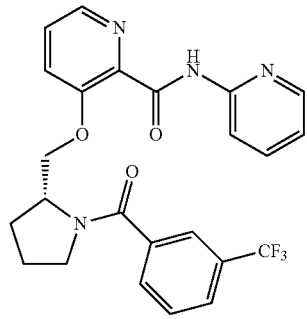

[Chem.40]

Step 1. (R)-3-((1-(3-(trifluoromethyl)benzoyl)pyrrolidin-2-yl)methoxy)picolinamide The title compound was prepared according to the procedure described in Step 5 of EXAMPLE 31 using (R)-3-(pyrrolidin-2-ylmethoxy)picolinamide dihydrochloride (EXAMPLE 1 Step 3) and 3-(trifluoromethyl)benzoic acid instead of ammonium chloride and 5-methoxy-3-(((R)-1-(trans-4-(trifluoromethyl)cyclohexanecarbonyl)pyrrolidin-2-yl)methoxy)picolinic acid.

$^1$H-NMR (CDCl$_3$) δ 8.20 (1H, d, J=4.4 Hz), 7.79 (1H, s), 7.75-7.60 (3H, m), 7.60-7.47 (2H, m), 7.40 (1H, dd, J=8.0, 4.4 Hz), 5.56 (1H, brs), 4.62 (2H, d, J=6.6 Hz), 4.29 (1H, d, J=7.3 Hz), 3.81 (1H, dt, J=9.5, 6.6 Hz), 3.43 (1H, m), 2.50-2.10 (3H, m), 1.82 (1H, m).

MS (ESI) m/z: 394 (M+H)$^+$, 392 (M−H)$^-$.

Step 2. (R)—N-(pyridin-2-yl)-3-((1-(3-(trifluoromethyl)benzoyl)pyrrolidin-2-yl)methoxy)picolinamide The title compound was prepared according to the procedure described in Step 2 of EXAMPLE 75 using (R)-3-((1-(3-(trifluoromethyl)benzoyl)pyrrolidin-2-yl)methoxy)picolinamide (EXAMPLE 78 Step 1) instead of. 3-(((R)-1-(trans-4-(trifluoromethyl)cyclohexanecarbonyl)pyrrolidin-2-yl)methoxy)picolinamide with preparative HPLC purification.

MS (ESI) m/z: 471 (M+H)$^+$, 469 (M−H)$^-$.

HPLC Retention time: 1.74 min (Method C).

Example 79

3-(((2R,4R)-4-hydroxy-1-(trans-4-(trifluoromethyl) cyclohexanecarbonyl)pyrrolidin-2-yl)methoxy)-N-(pyridin-2-yl)picolinamide

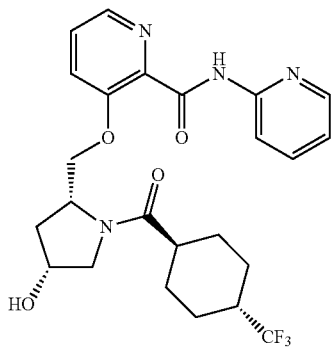

[Chem.41]

Step 1. (2R,4R)-1-tert-butyl 2-methyl 4-(benzyloxymethoxy)pyrrolidine-1,2-dicarboxylate To a mixture of (2R,4R)-1-tert-butyl 2-methyl 4-hydroxypyrrolidine-1,2-dicarboxylate (2.12 g, 8.65 mmol) and N,N-diisopropylethylamine (3.01 mL, 17.3 mmol) in dichloromethane (30 mL) was added benzyl chloromethyl ether (2.71 g, 17.3 mmol). After stirring at room temperature for 18 h, the mixture was poured into water. The aqueous layer was extracted with dichloromethane three times. The combined organic layers were dried over magnesium sulfate and concentrated in vacuo to afford an oil. The residual oil was purified by silica gel column chromatography (ethyl acetate/hexane 1:4 to 1:3) to give 2.29 g (72%) of the title compound as a colorless oil.

$^1$H-NMR (CDCl$_3$) δ 7.40-7.26 (5H, m), 4.77-4.70 (2H, m), 4.63-4.50 (2H, m), 4.35-4.25 (2H, m), 3.73 (3H, s), 3.75-3.50 (2H, m), 2.45-2.29 (2H, m), 1.50-1.40 (9H, m).

MS (ESI) m/z: 366 (M+H)$^+$.

Step 2. (2R,4R)-tert-butyl 4-(benzyloxymethoxy)-2-(hydroxymethyl)pyrrolidine-1-carboxylate To a mixture of (2R,4R)-1-tert-butyl 2-methyl 4-(benzyloxymethoxy)pyrrolidine-1,2-dicarboxylate (2.29 g, 6.27 mmol, EXAMPLE 79 Step 1) and lithium chloride (586 mg, 13.8 mmol) in ethanol (25 mL) was added sodium borohydride (522 mg, 13.8 mmol) at 0° C., and the mixture was stirred at room temperature for 24 h. Then, the mixture was poured into water, and the aqueous layer was extracted with ethyl acetate three times. The combined organic layers were dried over magnesium sulfate and concentrated in vacuo. The residual oil was purified by silica gel column chromatography (ethyl acetate/hexane 1:2 to 2:3) to give 1.72 g (81%) of the title compound as a colorless oil.

$^1$H-NMR (CDCl$_3$) δ 7.40-7.25 (5H, m), 4.79 (2H, s), 4.65-3.35 (8H, m), 2.30-2.18 (1H, m), 1.80-1.65 (1H, m), 1.47 (9H, m). A signal due to OH was not observed.

MS (ESI) m/z: 338 (M+H)$^+$.

Step 3. ethyl 3-(((2R,4R)-4-(benzyloxymethoxy)-1-(tert-butoxycarbonyl)pyrrolidin-2-yl)methoxy)picolinate The title compound was prepared according to the procedure described in Step 1 of EXAMPLE 29 using (2R,4R)-tert-butyl 4-(benzyloxymethoxy)-2-(hydroxymethyl)pyrrolidine-1-carboxylate (EXAMPLE 79 Step 2) and ethyl 3-hydroxypicolinate instead of (R)-pyrrolidin-2-ylmethanol and 5-chloropyridin-3-ol.

$^1$H-NMR (CDCl$_3$) δ 8.42-8.20 (1H, m), 7.6-7.25 (7H, m), 4.82-3.40 (10H, m), 4.43 (2H, q, J=7.3 Hz), 2.48-2.10 (2H, m), 1.47 (9H, s), 1.41 (3H, t, J=7.3 Hz).

MS (ESI) m/z: 487 (M+H)$^+$.

Step 4. ethyl 3-(((2R,4R)-4-(benzyloxymethoxy) pyrrolidin-2-yl)methoxy)picolinate To an ice-cold solution of ethyl 3-(((2R,4R)-4-(benzyloxymethoxy)-1-(tert-butoxycarbonyl)pyrrolidin-2-yl)methoxy)picolinate (845 mg, 1.74 mmol, EXAMPLE 79 Step 3) in dichloromethane (12 mL) was added trifluoroacetic acid, and the mixture was stirred at 0° C. for 1 h. The mixture was warmed to room temperature and stirred for 1 h at this temperature, then the mixture was concentrated in vacuo to afford an oil. The residual oil was purified by NH-gel column chromatography (ethyl acetate only to methanol/ethyl acetate 1:10) to give 200 mg (30%) of the title compound as a pale yellow oil.

$^1$H-NMR (CDCl$_3$) δ 8.30 (1H, d, J=4.4 Hz), 7.41-7.23 (7H, m), 4.78 (2H, s), 4.60 (2H, s), 4.44 (2H, q, J=7.3 Hz), 4.50-4.32 (1H, m), 4.13-4.02 (2H, m), 3.63-3.51 (1H, m), 3.18-3.05 (2H, m), 2.31-2.20 (1H, m), 1.80-1.70 (1H, m), 1.42 (3H, t, J=7.3 Hz). A signal due to NH was not observed.

MS (ESI) m/z: 387 (M+H)$^+$.

Step 5. ethyl 3-(((2R,4R)-4-(benzyloxymethoxy)-1-(trans-4-(trifluoromethyl)cyclohexanecarbonyl)pyrrolidin-2-yl)methoxy)picolinate The title compound was prepared according to the procedure described in Step 1 of EXAMPLE 3 using ethyl 3-(((2R,4R)-4-(benzyloxymethoxy)pyrrolidin-2-yl)methoxy)picolinate (EXAMPLE 79 Step 4) and trans-4-(trifluoromethyl)cyclohexanecarboxylic acid instead of (R)-3-(pyrrolidin-2-ylmethoxy)picolinamide dihydrochloride and indole-2-carboxylic acid.

$^1$H-NMR (CDCl$_3$) δ 8.28-8.22 (1H, m), 7.63-7.58 (1H, m), 7.43-7.22 (6H, m), 4.90-4.78 (2H, m), 4.80-4.10 (6H, m), 4.42 (2H, q, J=7.4 Hz), 3.68-3.51 (2H, m), 2.50-1.21 (12H, m), 1.41 (3H, t, J=7.4 Hz).

MS (ESI) m/z: 565 (M+H)$^+$.

Step 6. 3-(((2R,4R)-4-(benzyloxymethoxy)-1-(trans-4-(trifluoromethyl)cyclohexanecarbonyl)pyrrolidin-2-yl)methoxy)picolinic acid The title compound was prepared according to the procedure described in Step 4 of EXAMPLE 31 using ethyl 3-(((2R,4R)-4-(benzyloxymethoxy)-1-(trans-4-(trifluoromethyl)cyclohexanecarbonyl)pyrrolidin-2-yl)methoxy)picolinate (EXAMPLE 79 Step 5) instead of ethyl 5-methoxy-3-(((R)-1-(trans-4-(trifluoromethyl)cyclohexanecarbonyl)pyrrolidin-2-yl)methoxy)picolinate.

$^1$H-NMR (CDCl$_3$) δ 8.30-8.18 (1H, br), 7.85-7.75 (1H, br), 7.61-7.50 (1H, br), 7.40-7.20 (5H, m), 4.88-3.50 (10H, m), 2.40-1.65 (8H, m), 1.60-1.18 (4H, m). A signal due to COOH was not observed.

MS (ESI) m/z: 537 (M+H)$^+$, 535 (M−H)$^−$.

Step 7. 3-(((2R,4R)-4-(benzyloxymethoxy)-1-(trans-4-(trifluoromethyl)cyclohexanecarbonyl)pyrrolidin-2-yl)methoxy)-N-(pyridin-2-yl)picolinamide The title compound was prepared according to the procedure described in Step 4 of EXAMPLE 1 using 3-(((2R,4R)-4-(benzyloxymethoxy)-1-(trans-4-(trifluoromethyl)cyclohexanecarbonyl)pyrrolidin-2-yl)methoxy)picolinic acid (EXAMPLE 79 Step 6) and pyridin-2-amine instead of cis-4-(trifluoromethyl)cyclohexanecarboxylic acid and (R)-3-(pyrrolidin-2-ylmethoxy)picolinamide dihydrochloride.

MS (ESI) m/z: 613 (M+H)$^+$, 611 (M−H)$^−$.

Step 8. 3-(((2R,4R)-4-hydroxy-1-(trans-4-(trifluoromethyl)cyclohexanecarbonyl)pyrrolidin-2-yl)methoxy)-N-(pyridin-2-yl)picolinamide The title compound was prepared according to the procedure described in Step 4 of EXAMPLE 79 using 3-(((2R,4R)-4-(benzyloxymethoxy)-1-(trans-4-(trifluoromethyl)cyclohexanecarbonyl)pyrrolidin-2-yl)methoxy)-N-(pyridin-2-yl)picolinamide (EXAMPLE 79 Step 7) instead of ethyl 3-(((2R,4R)-4-(benzyloxymethoxy)-1-(tert-butoxycarbonyl)pyrrolidin-2-yl)methoxy)picolinate with preparative HPLC purification.

MS (ESI) m/z: 493 (M+H)$^+$, 491 (M−H)$^−$.

HPLC Retention time: 2.54 min (Method B).

Example 80

3-(((2R,4R)-4-hydroxy-1-(trans-4-(trifluoromethyl)cyclohexanecarbonyl)pyrrolidin-2-yl)methoxy)-N-(isoxazol-3-yl)picolinamide

[Chem.42]

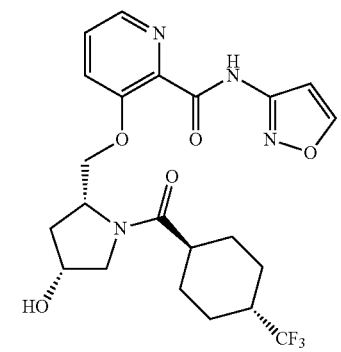

Step 1. 3-(((2R,4R)-4-(benzyloxymethoxy)-1-(trans-4-(trifluoromethyl)cyclohexanecarbonyl)pyrrolidin-2-yl)methoxy)-N-(isoxazol-3-yl)picolinamide The title compound was prepared according to the procedure described in Step 4 of EXAMPLE 1 using 3-(((2R,4R)-4-(benzyloxymethoxy)-1-(trans-4-(trifluoromethyl)cyclohexanecarbonyl)pyrrolidin-2-yl)methoxy)picolinic acid (EXAMPLE 79 Step 6) and isoxazol-3-amine instead of cis-4-(trifluoromethyl)cyclohexanecarboxylic acid and (R)-3-(pyrrolidin-2-ylmethoxy)picolinamide dihydrochloride.

MS (ESI) m/z: 603 (M+H)$^+$, 601 (M−H)$^−$.

Step 2. 3-(((2R,4R)-4-hydroxy-1-(trans-4-(trifluoromethyl)cyclohexanecarbonyl)pyrrolidin-2-yl)methoxy)-N-(isoxazol-3-yl)picolinamide The title compound was prepared according to the procedure described in Step 4 of EXAMPLE 79 using 3-(((2R,4R)-4-(benzyloxymethoxy)-1-(trans-4-(trifluoromethyl)cyclohexanecarbonyl)pyrrolidin-2-yl)methoxy)-N-(pyridin-2-yl)picolinamide (EXAMPLE 80 Step 1) instead of ethyl 3-(((2R,4R)-4-(benzyloxymethoxy)-1-(tert-butoxycarbonyl)pyrrolidin-2-yl)methoxy)picolinate with preparative HPLC purification.

MS (ESI) m/z: 483 (M+H)$^+$, 481 (M−H)$^−$.
HPLC Retention time: 2.52 min (Method B).

Example 81

3-(((2R,4R)-4-hydroxy-1-(trans-4-(trifluoromethyl)cyclohexanecarbonyl)pyrrolidin-2-yl)methoxy)-N-(oxazol-2-yl)picolinamide

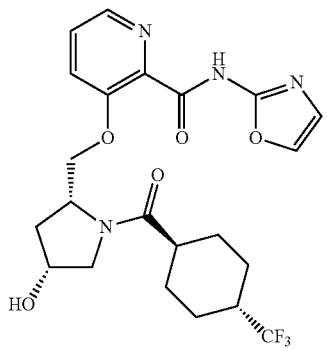

[Chem.43]

Step 1. 3-(((2R,4R)-4-(benzyloxymethoxy)-1-(trans-4-(trifluoromethyl)cyclohexanecarbonyl)pyrrolidin-2-yl)methoxy)-N-(oxazol-2-yl)picolinamide The title compound was prepared according to the procedure described in Step 1 of EXAMPLE 3 using 3-(((2R,4R)-4-(benzyloxymethoxy)-1-(trans-4-(trifluoromethyl)cyclohexanecarbonyl)pyrrolidin-2-yl)methoxy)picolinic acid (EXAMPLE 79 Step 6) and oxazol-2-amine instead of indole-2-carboxylic acid and (R)-3-(pyrrolidin-2-ylmethoxy)picolinamide dihydrochloride.

MS (ESI) m/z: 603 (M+H)$^+$, 601 (M−H)$^−$.

Step 2. 3-(((2R,4R)-4-hydroxy-1-(trans-4-(trifluoromethyl)cyclohexanecarbonyl)pyrrolidin-2-yl)methoxy)-N-(oxazol-2-yl)picolinamide The title compound was prepared according to the procedure described in Step 4 of EXAMPLE 79 using 3-(((2R,4R)-4-(benzyloxymethoxy)-1-(trans-4-(trifluoromethyl)cyclohexanecarbonyl)pyrrolidin-2-yl)methoxy)-N-(oxazol-2-yl)picolinamide (EXAMPLE 81 Step 1) instead of ethyl 3-(((2R,4R)-4-(benzyloxymethoxy)-1-(tert-butoxycarbonyl)pyrrolidin-2-yl)methoxy)picolinate with preparative HPLC purification.

MS (ESI) m/z: 483 (M+H)$^+$, 481 (M−H)$^−$.
HPLC Retention time: 1.39 min (Method C).

Example 82

N-benzyl-3-(((2R,4S)-4-hydroxy-1-(trans-4-(trifluoromethyl)cyclohexanecarbonyl)pyrrolidin-2-yl)methoxy)picolinamide

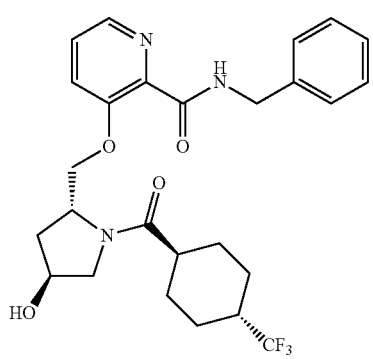

[Chem.44]

Step 1. ethyl 3-(((2R,4S)-1-(tert-butoxycarbonyl)-4-((tert-butyldimethylsilyl)oxy)pyrrolidin-2-yl)methoxy)picolinate The title compound was prepared according to the procedure described in Step 1 of EXAMPLE 29 using (2R,4S)-tert-butyl 4-((tert-butyldimethylsilyl)oxy)-2-(hydroxymethyl)pyrrolidine-1-carboxylate (PCT Int. Appl., WO2009026197) and ethyl 3-hydroxypicolinate instead of (R)-pyrrolidin-2-ylmethanol and 5-chloropyridin-3-ol.

$^1$H-NMR (CDCl$_3$) δ 8.25 (1H, brd, J=4.0 Hz), 7.5-7.3 (2H, m), 4.52 (1H, m), 4.42 (2H, q, J=7.3 Hz), 4.3-4.1 (3H, m), 3.6-3.3 (2H, m), 2.27 (1H, m), 2.05 (1H, m), 1.44 (9H, s), 1.42 (3H, t, J=7.3 Hz), 0.87 (9H, s), 0.08 (6H, s).
MS (ESI) m/z: 481 (M+H)$^+$.

Step 2. ethyl 3-(((2R,4S)-4-hydroxypyrrolidin-2-yl)methoxy)picolinate dihydrochloride The title compound was prepared according to the procedure described in Step 3 of EXAMPLE 1 using ethyl 3-(((2R,4S)-1-(tert-butoxycarbonyl)-4-((tert-butyldimethylsilyl)oxy)pyrrolidin-2-yl)methoxy)picolinate (EXAMPLE 82 Step 1) instead of (R)-tert-butyl 2-((2-carbamoylpyridin-3-yloxy)methyl)pyrrolidine-1-carboxylate.

MS (ESI) m/z: 267 (M+H)$^+$.

Step 3. ethyl 3-(((2R,4S)-4-hydroxy-1-(trans-4-(trifluoromethyl)cyclohexanecarbonyl)pyrrolidin-2-yl)methoxy)picolinate The title compound was prepared according to the procedure described in Step 1 of EXAMPLE 3 using ethyl 3-(((2R,4S)-4-hydroxypyrrolidin-2-yl)methoxy)picolinate dihydrochloride (EXAMPLE 82 Step 2) and trans(4-trifluoromethyl)cyclohexanecarboxylic acid instead of (R)-3-(pyrrolidin-2-ylmethoxy)picolinamide dihydrochloride and indol-2-carboxylic acid.

$^1$H-NMR (CDCl$_3$) δ 8.27 (1H, dd, J=3.7, 2.2 Hz), 7.39 (2H, m), 4.74 (1H, br), 4.57 (2H, m), 4.42 (2H, q, J=7.3 Hz) 4.09 (1H, m), 3.80 (1H, dd, J=10.5, 5.1 Hz), 3.54 (1H, brd, J=10.5 Hz), 2.5-2.4 (1H, m), 2.32 (1H, m), 2.2-1.9 (5H, m), 1.43 (3H, t, J=7.3 Hz), 1.7-1.2 (6H, m).
MS (ESI) m/z: 445 (M+H)$^+$.

Step 4. 3-(((2R,4S)-4-hydroxy-1-(trans-4-(trifluoromethyl)cyclohexanecarbonyl)pyrrolidin-2-yl)methoxy)picolinic acid The title compound was prepared according to the procedure described in Step 4 of EXAMPLE 31 using ethyl 3-(((2R,4S)-4-hydroxy-1-(trans-4-(trifluoromethyl)cyclohexanecarbonyl)pyrrolidin-2-yl)methoxy)picolinate (EXAMPLE 82 Step 3) instead of ethyl 5-methoxy-3-(((R)-1-(trans-4-(trifluoromethyl)cyclohexanecarbonyl)pyrrolidin-2-yl)methoxy)picolinate.
MS (ESI) m/z: 415 (M−H)$^−$.

Step 5. N-benzyl-3-(((2R,4S)-4-hydroxy-1-(trans-4-(trifluoromethyl)cyclohexanecarbonyl)pyrrolidin-2-yl)methoxy)picolinamide The title compound was prepared according to the procedure described in Step 3 of EXAMPLE 1 using 3-(((2R,4S)-4-hydroxy-1-(trans-4-(trifluoromethyl)cyclohexanecarbonyl)pyrrolidin-2-yl)methoxy)picolinic acid (EXAMPLE 82 Step 4) and benzylamine instead of indol-2-carboxylic acid and (R)-tert-butyl 2-((2-carbamoylpyridin-3-yloxy)methyl)pyrrolidine-1-carboxylate with preparative HPLC purification.
MS (ESI) m/z: 506 (M+H)$^+$.
HPLC Retention time: 1.53 min (Method C).

Example 83

3-(((2R,4S)-4-hydroxy-1-(trans-4-(trifluoromethyl)cyclohexanecarbonyl)pyrrolidin-2-yl)methoxy)-N-(pyridin-2-yl)picolinamide

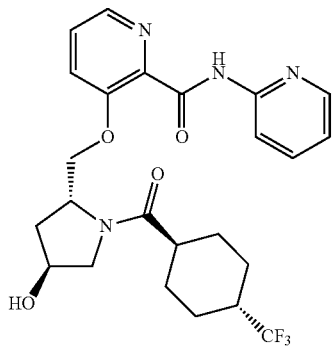

[Chem.45]

The title compound was prepared according to the procedure described in Step 3 of EXAMPLE 1 using 3-(((2R,4S)-4-hydroxy-1-(trans-4-(trifluoromethyl)cyclohexanecarbonyl)pyrrolidin-2-yl)methoxy)picolinic acid (EXAMPLE 82 Step 4) and 2-aminopyridine instead of indol-2-carboxylic acid and (R)-tert-butyl 2-((2-carbamoylpyridin-3-yloxy)methyl)pyrrolidine-1-carboxylate with preparative HPLC purification.
MS (ESI) m/z: 493 (M+H) 491 (M−H)$^−$.
HPLC Retention time: 1.49 min (Method C).

The starting materials of following EXAMPLE 84-95, tert-butyl 3-(hydroxymethyl)-3-methylpyrrolidine-1-carboxylate, tert-butyl 1-(hydroxymethyl)-3-azabicyclo[3.1.0]hexane-3-carboxylate, and tert-butyl 3-(hydroxymethyl)pyrrolidine-1-carboxylate were prepared from the corresponding N-Boc amino acid methyl or ethyl ester by similar method as described in step 2 of Example 79. The corresponding N-Boc amino acid methyl or ethyl ester was prepared by usual manner from the corresponding amino acid.

Example 84

5-chloro-3-((3-methyl-1-(trans-4-(trifluoromethyl)cyclohexanecarbonyl)pyrrolidin-3-yl)methoxy)picolinamide

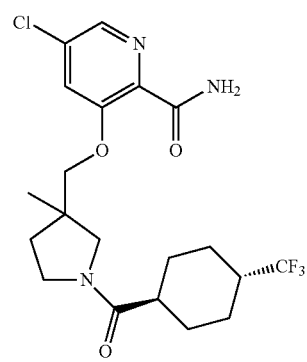

[Chem.46]

Step 1. tert-butyl 3-(((5-chloropyridin-3-yl)oxy)methyl)-3-methylpyrrolidine-1-carboxylate The title compound was prepared according to the procedure described in Step 1 of EXAMPLE 29 using tert-butyl 3-(hydroxymethyl)-3-methylpyrrolidine-1-carboxylate instead of (R)-tert-butyl 2-(hydroxymethyl)pyrrolidine-1-carboxylate.
$^1$H-NMR (CDCl$_3$) δ 8.20 (2H, s), 7.27 (1H, s), 3.81 (2H, s), 4.45 (1H, m), 3.44 (3H, m) 3.17 (1H, dd, J=15.4, 1.0 Hz), 1.99 (1H, m), 1.73 (1H, m), 1.46 (9H, s), 1.23 (3H, s)
MS (ESI) m/z: 327 (M+H)$^+$.

Step 2. 3-((1-(tert-butoxycarbonyl)-3-methylpyrrolidin-3-yl)methoxy)-5-chloropyridine 1-oxide The title compound was prepared according to the procedure described in Step 2 of EXAMPLE 29 using tert-butyl 3-(((5-chloropyridin-3-yl)oxy)methyl)-3-methylpyrrolidine-1-carboxylate (EXAMPLE 84, Step 1) instead of (R)-tert-butyl 2-((5-chloropyridin-3-yloxy)methyl)pyrrolidine-1-carboxylate.

¹H-NMR (CDCl₃) δ 7.92 (1H, s), 7.87 (1H, s), 6.91 (1H, s), 3.79 (2H, s), 3.5-3.2 (3H, m), 3.2-3.1 (1H, m), 1.92 (1H, m), 1.70 (1H, m), 1.47 (9H, s), 1.21 (3H, s)

MS (ESI) m/z: 343 (M+H)⁺.

Step 3. tert-butyl 3-(((5-chloro-2-cyanopyridin-3-yl)oxy)methyl)-3-methylpyrrolidine-1-carboxylate The title compound was prepared according to the procedure described in Step 3 of EXAMPLE 29 using 3-((1-(tert-butoxycarbonyl)-3-methylpyrrolidin-3-yl)methoxy)-5-chloropyridine 1-oxide (EXAMPLE 84, Step 2) instead of (R)-3-((1-(tert-butoxycarbonyl)pyrrolidin-2-yl)methoxy)-5-chloropyridine 1-oxide.

¹H-NMR (CDCl₃) δ 8.26 (1H, d, J=1.3 Hz), 7.35 (1H, d, J=2.0 Hz), 3.91 (2H, s), 3.48 (3H, m), 3.21 (1H, m), 2.04 (1H, m), 1.81 (1H, m), 1.46 (9H, s), 1.30 (3H, s)

MS (ESI) m/z: 252 (M+H−Boc)⁺.

Step 4. 5-chloro-3-((3-methylpyrrolidin-3-yl)methoxy)picolinonitrile dihydrochloride The title compound was prepared according to the procedure described in Step 3 of EXAMPLE 1 using tert-butyl 3-(((5-chloro-2-cyanopyridin-3-yl)oxy)methyl)-3-methylpyrrolidine-1-carboxylate (EXAMPLE 84, Step 4) instead of (R)-tert-butyl 2-((2-carbamoylpyridin-3-yloxy)methyl)pyrrolidine-1-carboxylate.

MS (ESI) m/z: 252 (M+H)⁺.

Step 5

5-chloro-3-((3-methyl-1-(trans-4-(trifluoromethyl)cyclohexanecarbonyl)pyrrolidin-3-yl)methoxy)picolinonitrile The title compound was prepared according to the procedure described in Step 3 of EXAMPLE 1 using 5-chloro-3-((3-methylpyrrolidin-3-yl)methoxy)picolinonitrile dihydrochloride (EXAMPLE 84, Step 4) and trans-4-(trifluoromethyl)cyclohexanecarboxylic acid instead of (R)-3-(pyrrolidin-2-ylmethoxy)picolinamide dihydrochloride and indole-2-carboxylic acid.

¹H-NMR (CDCl₃) δ 8.28 (1H, dd, J=5.9, 1.5 Hz), 7.35 (1H, dd, J=5.9, 1.5 Hz), 3.93 (2H, s), 3.8-3.5 (3H, m), 3.37 (1H, m), 2.2-1.9 (2H, m), 2.18-1.75 (6H, m), 1.58 (2H, m), 1.50-1.22 (2H, m), 1.33 (3H, s)

MS (ESI) m/z: 430 (M+H)⁺.

Step 6. 5-chloro-3-((3-methyl-1-(trans-4-(trifluoromethyl)cyclohexanecarbonyl)pyrrolidin-3-yl)methoxy)picolinamide The title compound was prepared according to the procedure described in Step 2 of EXAMPLE 1 using 5-chloro-3-((3-methyl-1-(trans-4-(trifluoromethyl)cyclohexanecarbonyl)pyrrolidin-3-yl)methoxy)picolinonitrile (EXAMPLE 29 Step 3) instead of (R)-tert-butyl 2-((2-cyanopyridin-3-yloxy)methyl)pyrrolidine-1-carboxylate with preparative HPLC purification.

¹H-NMR (CDCl₃) (CDCl₃) δ 8.16 (1H, d, J=2.2 Hz), 7.46 (1H, br), 7.36 (1H, d, J=1.5 Hz), 5.55 (1H, br), 3.89 (2H, m), 3.8-3.5 (3H, m), 3.33 (1H, dd, J=11.0, 10.2 Hz), 2.4-1.2 (12H, m), 1.33 (3H, s)

MS (ESI) m/z: 448 (M+H)⁺.

HPLC Retention time: 1.57 min (Method C).

Example 85

5-chloro-3-((3-(trans-4-(trifluoromethyl)cyclohexanecarbonyl)-3-azabicyclo[3.1.0]hexan-1-yl)methoxy)picolinamide

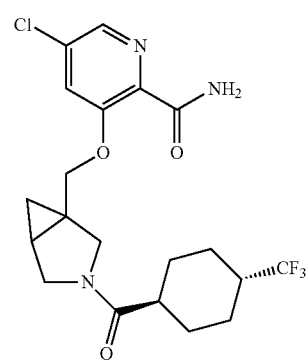

[Chem.47]

The title compound was prepared according to the procedure described in EXAMPLE 84 using tert-butyl 1-(hydroxymethyl)-3-azabicyclo[3.1.0]hexane-3-carboxylate instead of tert-butyl 3-(hydroxymethyl)-3-methylpyrrolidine-1-carboxylate with preparative HPLC purification.

¹H-NMR (CDCl₃) δ 8.21 (1H, d, J=2.0 Hz), 7.47 (1H, br), 7.36 (1H, d, J=2.0 Hz), 5.56 (1H, br), 4.30-4.05 (2H, m), 3.94 (1H, dd, J=12.5, 11.9 Hz), 3.86 (1H, m), 3.8-3.6 (1H, m), 3.6-3.4 (1H, m), 2.4-2.2 (1H, m), 2.1-1.8 (5H, m), 1.7-1.5 (3H, m), 1.5-1.2 (2H, m), 1.2-1.1 (1H, m), 0.62 (1H, m)

MS (ESI) m/z: 446 (M+H)⁺.

HPLC Retention time: 1.54 min (Method C).

Example 86

N-benzyl-3-(trans-4-(trifluoromethyl)cyclohexanecarbonyl)pyrrolidin-3-yl)methoxy)picolinamide

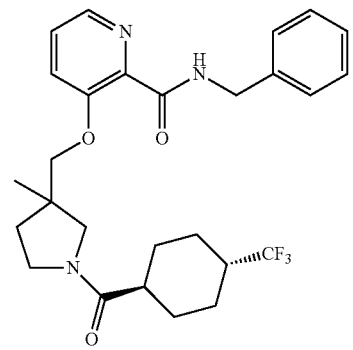

[Chem.48]

Step 1. ethyl 3-((1-(tert-butoxycarbonyl)-3-methylpyrrolidin-3-yl)methoxy)picolinate The title compound was prepared according to the procedure described in Step 1 of EXAMPLE 29 using tert-butyl 3-(hydroxymethyl)-3-methylpyrrolidine-1-carboxylate and ethyl 3-hydroxypicolinate instead of (R)-tert-butyl 2-(hydroxymethyl)pyrrolidine-1-carboxylate and 5-chloropyridin-3-ol.

$^1$H-NMR (CDCl$_3$) δ 8.29 (1H, d, J=3.7 Hz), 7.4-7.2 (2H, m), 4.45 (2H, q, J=7.3 Hz), 3.85 (2H, qAB, J=9.5 Hz), 3.5-3.4 (3H, m), 3.17 (1H, dd, J=16.1, 1.0 Hz), 2.2-1.95 (1H, m), 1.74 (1H, m), 1.46 (9H, s), 1.42 (3H, t, J=7.3 Hz), 1.26 (3H, s)

MS (ESI) m/z: 365 (M+H)$^+$.

Step 2. ethyl 3-((3-methylpyrrolidin-3-yl)methoxy)picolinate dihydrochloride The title compound was prepared according to the procedure described in Step 3 of EXAMPLE 1 using ethyl 3-((1-(tert-butoxycarbonyl)-3-methylpyrrolidin-3-yl)methoxy)picolinate (EXAMPLE 86, Step 1) instead of (R)-tert-butyl 2-((2-carbamoylpyridin-3-yloxy)methyl)pyrrolidine-1-carboxylate.

MS (ESI) m/z: 265 (M+H)$^+$.

Step 3. ethyl 3-((3-methyl-1-(trans-4-(trifluoromethyl)cyclohexanecarbonyl)pyrrolidin-3-yl)methoxy) picolinate The title compound was prepared according to the procedure described in Step 3 of EXAMPLE 1 using ethyl 3-((3-methylpyrrolidin-3-yl)methoxy)picolinate dihydrochloride (EXAMPLE 86, Step 2) and trans-4-(trifluoromethyl)cyclohexanecarboxylic acid instead of (R)-3-(pyrrolidin-2-ylmethoxy)picolinamide dihydrochloride and indole-2-carboxylic acid.

$^1$H-NMR (CDCl$_3$) δ 8.31 (1H, br), 7.42-7.25 (2H, m), 4.45 (2H, m), 3.86 (2H, qAB, J=8.6 Hz), 3.5-3.8 (3H, m), 3.32 (1H, dd, J=15.2, 10.5 Hz), 2.34 (1H, m), 2.2-1.5 (10H, m), 1.2-1.5 (7H, m)

MS (ESI) m/z: 443 (M+H)$^+$.

Step 4. 3-((3-methyl-1-(trans-4-(trifluoromethyl)cyclohexanecarbonyl)pyrrolidin-3-yl)methoxy)picolinic acid The title compound was prepared according to the procedure described in Step 4 of EXAMPLE 31 using ethyl 3-((3-methyl-1-(trans-4-(trifluoromethyl)cyclohexanecarbonyl)pyrrolidin-3-yl)methoxy)picolinate (EXAMPLE 86 Step 3) in stead of ethyl 5-methoxy-3-(((R)-1-(trans-4-(trifluoromethyl)cyclohexanecarbonyl)pyrrolidin-2-yl)methoxy)picolinate.

MS (ESI) m/z: 415 (M+H)$^+$, 413 (M−H)$^-$.

Step 5. N-benzyl-3-((3-methyl-1-(trans-4-(trifluoromethyl)cyclohexanecarbonyl)pyrrolidin-3-yl)methoxy)picolinamide The title compound was prepared according to the procedure described in Step 3 of EXAMPLE 1 using benzylamine and 3-((3-methyl-1-(trans-4-(trifluoromethyl)cyclohexanecarbonyl)pyrrolidin-3-yl)methoxy)picolinic acid (EXAMPLE 86, Step 4) instead of (R)-3-(pyrrolidin-2-ylmethoxy)picolinamide dihydrochloride and indole-2-carboxylic acid with preparative HPLC purification.

MS (ESI) m/z: 504 (M+H)$^+$.
HPLC Retention time: 1.72 min (Method C).

Example 87

3-((3-methyl-1-(trans-4-(trifluoromethyl)cyclohexanecarbonyl)pyrrolidin-3-yl)methoxy)-N-((tetrahydro-2H-pyran-4-yl)methyl)picolinamide

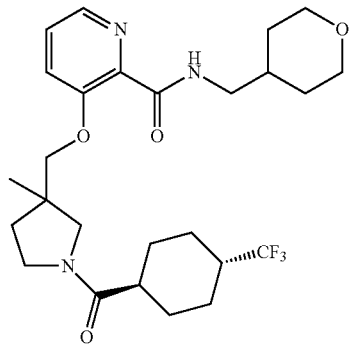

[Chem.49]

The title compound was prepared according to the procedure described in Step 3 of EXAMPLE 1 using (tetrahydro-2H-pyran-4-yl)methanamine and 3-((3-methyl-1-(trans-4-(trifluoromethyl)cyclohexanecarbonyl)pyrrolidin-3-yl)methoxy)picolinic acid (EXAMPLE 86, Step 4) instead of (R)-3-(pyrrolidin-2-ylmethoxy)picolinamide dihydrochloride and indole-2-carboxylic acid with preparative HPLC purification.

MS (ESI) m/z: 512 (M+H)$^+$.
HPLC Retention time: 1.53 min (Method C).

Example 88

N-benzyl-3-((3-(trans-4-(trifluoromethyl)cyclohexanecarbonyl)-3-azabicyclo[3.1.0]hexan-1-yl)methoxy)picolinamide

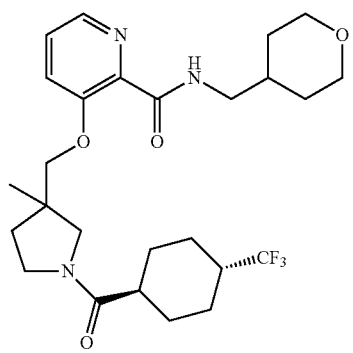

[Chem.50]

Step 1. tert-butyl 1-(((2-(ethoxycarbonyl)pyridin-3-yl)oxy)methyl)-3-azabicyclo[3.1.0]hexane-3-carboxylate The title compound was prepared according to the procedure described in Step 1 of EXAMPLE 29 using tert-butyl 1-(hydroxymethyl)-3-azabicyclo[3.1.0]hexane-3-carboxylate and ethyl 3-hydroxypicolinate instead of (R)-tert-butyl 2-(hydroxymethyl)pyrrolidine-1-carboxylate and 5-chloropyridin-3-ol.

$^1$H-NMR (CDCl$_3$) δ 8.30 (1H, d, J=4.4 Hz), 7.5-7.2 (2H, m), 4.45 (2H, q, J=6.6 Hz), 1.57 (1H, m), 1.45 (9H, s), 1.42 (3H, t, J=6.6 Hz), 0.95 (1H, m), 0.63 (1H, m)

MS (ESI) m/z: 363 (M+H)$^+$.

Step 2. ethyl 3-(3-azabicyclo[3.1.0]hexan-1-ylmethoxy)picolinate dihydrochloride The title compound was prepared according to the procedure described in Step 3 of EXAMPLE 1 using ethyl tert-butyl 1-(((2-(ethoxycarbonyl)pyridin-3-yl)oxy)methyl)-3-azabicyclo[3.1.0]hexane-3-carboxy late (EXAMPLE 88, Step 1) instead of (R)-tert-butyl 2-((2-carbamoylpyridin-3-yloxy)methyl)pyrrolidine-1-carboxylate.

MS (ESI) m/z: 263 (M+H)$^+$, 261 (M−H)$^-$.

Step 3. ethyl 3-((3-(trans-4-(trifluoromethyl)cyclohexanecarbonyl)-3-azabicyclo[3.1.0]hexan-1-yl)methoxy)picolinate The title compound was prepared according to the procedure described in Step 3 of EXAMPLE 1 using ethyl 3-(3-azabicyclo[3.1.0]hexan-1-ylmethoxy)picolinate dihydrochloride (EXAMPLE 88, Step 2) and trans-4-(trifluoromethyl)cyclohexanecarboxylic acid instead of (R)-3-(pyrrolidin-2-ylmethoxy)picolinamide dihydrochloride and indole-2-carboxylic acid.

$^1$H-NMR (CDCl$_3$) δ 8.32 (1H, m), 7.40-7.25 (2H, m), 4.41 (2H, dq, J=7.3, 3.7 Hz), 4.3-3.6 (5H, m), 3.48 (1H, m), 2.29 (1H, m), 2.05 (3H, m), 1.87 (2H, m), 1.8-1.2 (8H, m), 1.02 (1H, m), 0.59 (1H, m)

MS (ESI) m/z: 441 (M+H)$^+$.

Step 4. 3-((3-(trans-4-(trifluoromethyl)cyclohexanecarbonyl)-3-azabicyclo[3.1.0]hexan-1-yl)methoxy)picolinic acid The title compound was prepared according to the procedure described in Step 4 of EXAMPLE 31 using ethyl 3-((3-(trans-4-(trifluoromethyl)cyclohexanecarbonyl)-3-azabicyclo[3.1.0]hexan-1-yl)methoxy)picolinate (EXAMPLE 88 Step 3) in stead of ethyl 5-methoxy-3-(((R)-(trans-4-(trifluoromethyl)cyclohexanecarbonyl)pyrrolidin-2-yl)methoxy)picolinate.

MS (ESI) m/z: 413 (M+H)$^+$, 411 (M−H)$^-$.

Step 5. N-benzyl-3-((3-(trans-4-(trifluoromethyl)cyclohexanecarbonyl)-3-azabicyclo[3.1.0]hexan-1-yl)methoxy)picolinamide The title compound was prepared according to the procedure described in Step 3 of EXAMPLE 1 using benzylamine and 3-((3-(trans-4-(trifluoromethyl)cyclohexanecarbonyl)-3-azabicyclo[3.1.0]hexan-1-yl)methoxy)picolinic acid (EXAMPLE 88, Step 4) instead of (R)-3-(pyrrolidin-2-ylmethoxy)picolinamide dihydrochloride and indole-2-carboxylic acid with preparative HPLC purification.

MS (ESI) m/z: 502 (M+H)$^+$.

HPLC Retention time: 1.67 min (Method C).

Example 89 to 91

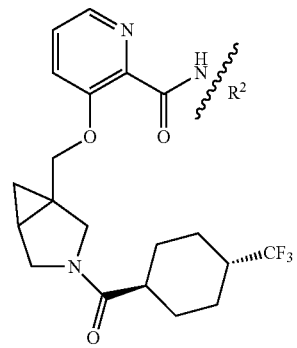

[Chem.51]

The following examples, EXAMPLE 89-91, were prepared according to the procedure similar to that described in the Step 1 of the EXAMPLE 3, using the 3-((3-(trans-4-(trifluoromethyl)cyclohexanecarbonyl)-3-azabicyclo[3.1.0] hexan-1-yl)methoxy)picolinic acid (EXAMPLE 88 Step 4) and appropriate precursor of amine, R$^2$—NH$_2$ with preparative HPLC purification.

TABLE 9

| EXAMPLES | R$^2$ | Chemical Name | HPLC Gradient Method | HPLC Retention Time (min.) | MS (ESI): m/z (M + H)+ |
|---|---|---|---|---|---|
| 89 | | N-((tetrahydro-2H-pyran-4-yl)methyl)-3-((3-(trans-4-(trifluoromethyl)cyclohexanecarbonyl)-3-azabicyclo[3.1.0]hexan-1-yl)methoxy)picolinamide | Method C | 1.50 | 510 |
| 90 | | N-(pyridin-2-yl)-3-((3-(trans-4-(trifluoromethyl)cyclohexanecarbonyl)-3-azabicyclo[3.1.0]hexan-1-yl)methoxy)picolinamide | Method C | 1.67 | 489 |

TABLE 9-continued

| EXAMPLES | R² | Chemical Name | HPLC Gradient Method | HPLC Retention Time (min.) | MS (ESI): m/z (M + H)+ |
|---|---|---|---|---|---|
| 91 | [tetrahydro-2H-pyran-4-yl structure] | N-(tetrahydro-2H-pyran-4-yl)-3-((3-(trans-4-(trifluoromethyl)cyclohexanecarbonyl)-3-azabicyclo[3.1.0]hexan-1-yl methoxy)picolinamide | Method C | 1.46 | 496 |

Example 92

N-(pyridin-2-yl)-3-((1-(trans-4-(trifluoromethyl)cyclohexanecarbonyl)pyrrolidin-3-yl)methoxy)picolinamide

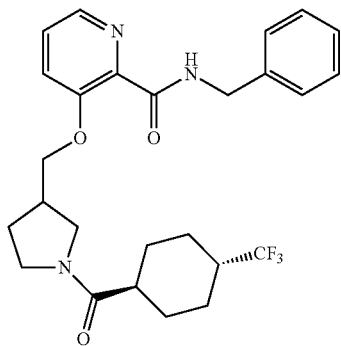

[Chem.52]

Step 1. ethyl 3-((1-(tert-butoxycarbonyl)pyrrolidin-3-yl)methoxy)picolinate The title compound was prepared according to the procedure described in Step 1 of EXAMPLE 29 using tert-butyl 3-(hydroxymethyl)pyrrolidine-1-carboxylate and ethyl 3-hydroxypicolinate instead of (R)-tert-butyl 2-(hydroxymethyl)pyrrolidine-1-carboxylate and 5-chloropyridin-3-ol.

¹H-NMR (CDCl₃) δ 8.29 (1H, brd, J=4.4 Hz), 7.39 (1H, dd, J=8.1, 4.4 Hz), 7.32 (1H, dd, J=8.1, 1.5 Hz), 4A5 (2H, q, J=7.3 Hz), 4.00 (2H, m), 3.7-3.3 (3H, m), 3.23 (1H, dd, J=11.0, 7.3 Hz), 2.74 (1H, m), 2.10 (1H, m), 1.70 (1H, m), 1.47 (9H, s), 1.42 (3H, t, J=7.3 Hz)

MS (ESI) m/z: 351 (M+H)⁺.

Step 2. ethyl 3-(pyrrolidin-3-ylmethoxy)picolinate

The title compound was prepared according to the procedure described in Step 4 of EXAMPLE 79 using ethyl 3-((1-(tert-butoxycarbonyl)pyrrolidin-3-yl)methoxy)picolinate (EXAMPLE 92, Step 1) instead of ethyl 3-(((2R,4R)-4-(benzyloxymethoxy)-1-(tert-butoxycarbonyl)pyrrolidin-2-yl)methoxy)picolinate.

MS (ESI) m/z: 251 (M+H)⁺.

Step 3. ethyl 3-((1-(trans-4-(trifluoromethyl)cyclohexanecarbonyl)pyrrolidin-2-yl)methoxy)picolinate The title compound was prepared according to the procedure described in Step 3 of EXAMPLE 1 using ethyl 3-(pyrrolidin-3-ylmethoxy)picolinate (EXAMPLE 92, Step 2) and trans-4-(trifluoromethyl)cyclohexanecarboxylic acid instead of (R)-3-(pyrrolidin-2-ylmethoxy)picolinamide dihydrochloride and indole-2-carboxylic acid.

¹H-NMR (CDCl₃) δ 8.32 (1H, t, J=4.4 Hz), 7.39 (1H, m), 7.32 (1H, dd, J=7.4, 3.7 Hz), 4.45 (2H, dq, 7.4, 2.9 Hz), 4.11 (1H, m), 3.96 (1H, dd, J=16.2, 7.3 Hz), 3.8-3.3 (4H, m), 2.85 (1H, m), 2.38 (1H, m), 2.2-1.2 (11H, m), 1.43 (3H, dt, J=7.3, 2.2 Hz)

MS (ESI) m/z: 429 (M+H)⁺.

Step 4. 3-((1-(trans-4-(trifluoromethyl)cyclohexanecarbonyl)pyrrolidin-3-yl)methoxy)picolinic acid The title compound was prepared according to the procedure described in Step 4 of EXAMPLE 31 using ethyl 3-((1-(trans-4-(trifluoromethyl)cyclohexanecarbonyl)pyrrolidin-3-yl)methoxy)picolinate (EXAMPLE 92 Step 3) in stead of ethyl 5-methoxy-3-(((R)-1-(trans-4-(trifluoromethyl)cyclohexanecarbonyl)pyrrolidin-2-yl)methoxy)picolinate.

MS (ESI) m/z: 401 (M+H)⁺, 399 (M−H)⁻.

Step 5. N-(pyridin-2-yl)-3-((1-(trans-4-(trifluoromethyl)cyclohexanecarbonyl)pyrrolidin-3-yl)methoxy)picolinamide The title compound was prepared according to the procedure described in Step 3 of EXAMPLE 1 using benzylamine and 3-((1-(trans-4-(trifluoromethyl)cyclohexanecarbonyl)pyrrolidin-3-yl)methoxy)picolinic acid (EXAMPLE 92, Step 4) instead of (R)-3-(pyrrolidin-2-ylmethoxy)picolinamide dihydrochloride and indole-2-carboxylic acid with preparative HPLC purification.

MS (ESI) m/z: 490 (M+H)⁺.

HPLC Retention time: 1.64 min (Method C).

Example 93 to 95

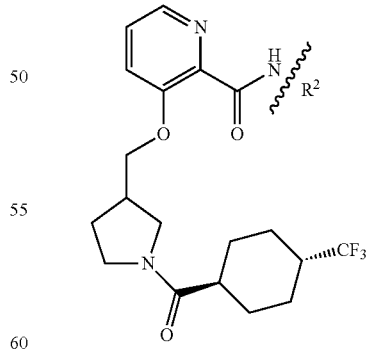

[Chem.53]

The following examples, EXAMPLE 93-95, were prepared according to the procedure similar to that described in the Step 1 of the EXAMPLE 3, using the 3-((1-(trans-4-(trifluoromethyl)cyclohexanecarbonyl)pyrrolidin-3-yl) methoxy)picolinic acid (EXAMPLE 92, Step 4) and appropriate precursor of amine, R²—NH₂ with preparative HPLC purification.

TABLE 10

| EXAMPLES | R² | Chemical Name | HPLC Gradient Method | HPLC Retention Time (min.) | MS (ESI): m/z (M + H)+ |
|---|---|---|---|---|---|
| 93 | (tetrahydro-2H-pyran-4-yl)methyl group | N-((tetrahydro-2H-pyran-4-yl)methyl)-3-((1-(trans-4-(trifluoromethyl)cyclohexanecarbonyl)pyrrolidin-3-yl)methoxy)picolinamide | Method C | 1.46 | 498 |
| 94 | pyridin-2-yl group | N-(pyridin-2-yl)-3-((1-(trans-4-(trifluoromethyl)cyclohexanecarbonyl)pyrrolidin-3-yl)methoxy)picolinamide | Method C | 1.64 | 477 |
| 95 | tetrahydro-2H-pyran-4-yl group | N-(tetrahydro-2H-pyran-4-yl)-3-((1-(trans-4-(trifluoromethyl)cyclohexanecarbonyl)pyrrolidin-3-yl)methoxy)picolinamide | Method C | 1.43 | 484 |

Pharmacological Assays

The ability of the picolinamide derivatives of the formula (I) to inhibit the $Na_{v1.3}$, $Na_{v1.7}$ and $Na_{v1.5}$ channels was measured by FRET assay and electrophysiology assay described below.

FRET Assay

This screen is used to determine the effects of compounds on human $Na_{v1.3}$, human $Na_{v1.7}$, and human $Na_{v1.5}$ channels, utilising the cell imaging technology by Hamamatsu Photonics's Functional Drug Screening System (FDSS). This experiment is based on FRET (Fluorescence Resonance Energy Transfer) and uses two fluorescent molecules. The first molecule, Oxonol (DiSBAC2(3)), is a highly fluorescent, negatively charged, hydrophobic ion that "senses" the transmembrane electrical potential. In response to changes in membrane potential, it can rapidly redistribute between two binding sites on opposite sides of the plasma membrane. The voltage dependent redistribution is transduced into a ratiometric fluorescent readout via a second fluorescent molecule (Coumarin (CC2-DMPE)) that binds specifically to one face of the plasma membrane and functions as a FRET partner to the mobile voltage-sensing ion. To enable the assay to work, the channels have to be pharmacologically held in the open state. This is achieved by treating the cells with veratridine.

Cell Maintenance:

Each HEK293 cells expressing human $Na_{v1.3}$ channels and HEK293 cells expressing human $Na_{v1.5}$ channels were grown in T225 flasks, in a 5% $CO_2$ humidified incubator to about 80% confluence. Media composition consisted of Dulbecco's Modified Eagle Medium (high glucose), 10% fetal calf serum (FCS), 100 units/ml Penicillin, 100 microgram/ml Streptomycin and 500 microgram/ml Geneticine.

CHO cells expressing human $Na_{v1.7}$ channels were grown in T225 flasks, in a 5% CO 2 humidified incubator to about 80% confluence. Media composition consisted of HAM/F12 with Glutamax 1.10% fetal calf serum (FCS), 100 units/ml Penicillin and 100 microgram/ml Hygromycin.

Protocol:

Seed each cell lines (1.5×10⁴ cells/well) into poly-D-lysine coated 384-well plates prior to experimentation.

Incubate at 37° C. in 5% $CO_2$ for 24 hours.

Wash each well with buffer #1 (140 mM NaCl, 4.5 mM KCl, 10 mM D-Glucose, 2 mM $CaCl_2$, 1 mM $MgCl_2$, 10 mM HEPES, pH 7.4 adjusted with NaOH) twice using plate washer.

Add 1st loading solution containing 5 µM CC2-DMPE and 0.02% Pluronic F-127 in buffer #1.

Incubate the plate at room temperature in dark for 0.5 hours.

Wash each well with buffer #2 (160 mM Choline, 10 mM D-Glucose, 0.1 mM $CaCl_2$, 1 mM $MgCl_2$, 10 mM HEPES, pH 7.4 adjusted with KOH) twice using plate washer.

Add 2nd loading solution containing 15 µM DiSBAC2(3), 0.5 mM VABSC-1, 10 µM veratridine and 0.004% Pluronic F-127 in buffer #2.

Add compound solutions into the assay plate and leave the plate for 30 minutes under the dark at room temperature.

Measure by FDSS.

The data was analyzed and reported as normalized ratios of intensities measured in the 465 nm and 575 nm channels. The process of calculating these ratios was performed as follows:

"FI465B"=the mean of fluorescence intensity as baseline (before Na+ ligand addition) at 465 nm "FI575B"=the mean of fluorescence intensity as baseline (before Na+ ligand addition) at 575 nm "FI465Max"=maximum fluorescence intensity at 465 nm after Na+ stimulation "FI575 Min"=minimum fluorescence intensity at 575 nm after Na+ stimulation "FR"=fluorescence ratio=(F1465Max/F1575 Min)-(F1465B/F1575B)

$$\text{Inhibition (\%)} = 100 - \frac{(FR \text{ of each well}) - (\text{median } FR \text{ in positive controls})}{(\text{median } FR \text{ in negative controls}) - (\text{median } FR \text{ in negative controls})} \times 100 \quad [\text{Math. 1}]$$

This analysis was performed using a computerized specific program designed for FDSS generated data. Fluorescence ratio values were plotted using XLfit to determine an $IC_{50}$ value for each compound.

Electrophysiology Assay

Whole cell patch clamp recording was used to assess the efficacy or selectivity of Na channel blocker on human $Na_{v1.3}$ (hSCN3A) expressing HEK293 cells or human $Na_{v1.7}$ (hSCN9A) expressing CHO cells. Human $Na_{v1.3}$ expressing HEK293 cells were grown in growth media which comprised: DMEM, 10% heat-inactivated FBS (Hyclone Laboratories Inc), 100 microgram/ml Penicillin/100 U/ml Streptomycin, 150 microgram/ml Zeocin, 3 microgram/ml Geneticin. Human $Na_{v1.7}$ expressing CHO cells were grown in growth media which comprised: HAMF-12, 9% heat-inactivated FBS (Hyclone Laboratories Inc), 100 microgram/ml Penicillin/100 U/ml Streptomycin, 100 microgram/ml Hygromycin.

Na channel expressing cells were dissociated by 0.05% Trypsine-EDTA, and then seeded on cover glass for 24-48 hr.

Glass pipettes were pulled to a tip diameter of 1-2 micrometer on a pipette puller. The pipettes were filled with the intracellular solution and a chloridized silver wire was inserted along its length, which was then connected to the headstage of the voltage-clamp amplifier (Axon Instruments or HEKA electronik). The extracellular recording solution consists of (mM): 140 NaCl, 5 KCl, 2 $CaCl_2$, 1 $MgCl_2$, 10 HEPES, 10 Glucose, pH 7.4 adjusted with NaOH. The internal solution consists of (mM): 120 CsF, 15 NaCl, 10 EGTA, 10 HEPES, pH 7.2 adjusted with CsOH; Upon insertion of the pipette tip into the bath, the pipette resistance was noted (acceptable range is between 1-3 megaohm). The junction potential between the pipette and bath solutions was zeroed on the amplifier. After establishing the whole-cell configuration, approximately 10 minutes were allowed for the pipette solution to equilibrate within the cell before beginning recording. Currents were lowpass filtered between 2-5 kHz and digitally sampled at 10 kHz. Series resistance was compensated (>80%) and was monitored continuously.

The normalized steady-state inactivation curve was constructed using 500 msec (for vehicle) or 60 sec (for drugs) conditioning pulse to different potentials followed immediately by the test pulse to 0 mV. Peak currents were plotted as fraction of the maximum current at the conditioning potentials ranging from −120 mV to −40 mV. V1/2 or k values were estimated from Boltzmann fits. The affinity of drugs to resting state of Na channels ($K_{resting}$ or $K_r$) was assessed by 30 msec test pulse from a negative holding potential of ?120 mV, where virtually all channels are in the resting state. $K_r$ value was calculated by a conventional 1:1 binding model:

$$K_{resting}(K_r) = [drug]Imax,drug/(Imax,control-Imax,drug))$$

where $K_{resting}$ (=$K_r$) is a dissociation constant for the resting state and [drug] is compound concentration. $I_{max}$, control and $I_{max}$, drug are peak currents in the absence and presence of compound, respectively.

The affinity of drug to inactivated state of Na channels ($K_{inact}$ or $K_i$) was estimated from the shift of the availability curve by compound. Interaction of the compound with the channel on inactivated state was evaluated by the following equation:

$$K_{inact}(K_i) = \{[drug]((1+[drug]/K_r)*exp(-\Delta V/k)-1)\} \qquad [Math.2]$$

where $K_{inact}$ (=$K_i$) is a dissociation constant for the inactivated state. $\Delta V$ is the compound-induced voltage shift of half maximal voltage of Boltzmann curve and k is the slope factor on presence of compound.

The compounds of the examples were tested in the above-described assay. The results are as follows:

All examples of the invention have an $IC_{50}$=<6 microM in the both $Na_{v1.3}$ and $Na_{v1.7}$ FRET Assays. Especially example 2, 5, 17, 18, 21, 25, 29, 30, 31, 35, 37, 39, 40, 41, 43, 47, 49, 50, 54, 62, 63, 65, 66, 68, and 69 of the invention have an $IC_{50}$=<0.5 microM in both of them.

The invention claimed is:

1. A compound of formula (I):

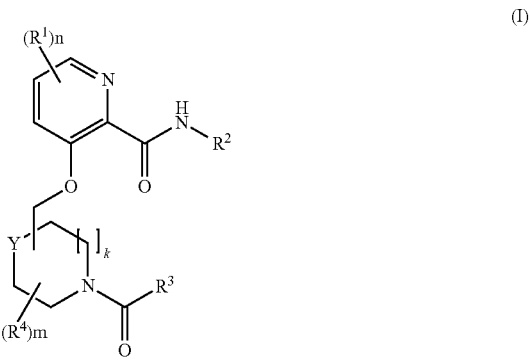

wherein:

$R^1$ is independently selected from the group consisting of:
(1) hydrogen, (2) halogen, (3) hydroxy, (4) —$O_p$—$C_{1-6}$ alkyl, where the alkyl is unsubstituted or substituted with one or more substituents selected from $R^5$, (5) —$O_p$—$C_{3-8}$ cycloalkyl, where the cycloalkyl is unsubstituted or substituted with one or more substituents selected from $R^5$, (6) $C_{2-4}$ alkenyl, where the alkenyl is unsubstituted or substituted with one or more substituents selected from $R^5$, (7) —(C=O)—$NR^6R^7$, (8) —$NR^6R^7$, (9) —$S(O)_2$—$NR^6R^7$, (10) —$NR^6$—$S(O)_2R^7$, (11) —$S(O)_r$—$R^8$, where r is 0, 1 or 2 and where $R^8$ is selected from the definitions of $R^6$ and $R^7$, (12) —$CO_2H$, and (13) —CN; where p is 0 or 1 (wherein if p is 0, a chemical bond is present in the place of $O_p$);
n is 1, 2, or 3; when n is two or more than two, $R^1$ may be the same or different;

$R^2$ is selected from the group consisting of:
(1) hydrogen, (2) $C_{1-6}$ alkyl, which is unsubstituted or substituted with one or more substituents selected from $R^5$, (3) $C_{3-8}$ cycloalkyl which is unsubstituted or substituted with one or more substituents selected from $R^5$, (4) phenyl, which is unsubstituted or substituted with one or more substituents selected from $R^5$, and (5) heterocycle, which is unsubstituted or substituted with one or more substituents selected from $R^5$;

$R^3$ is selected from the group consisting of:
(1) —$C_{0-3}$ alkyl—$O_p$—$C_{0-3}$ alkyl-cycloalkyl which is unsubstituted or substituted with one or more substituents selected from $R^5$, (2) —$C_{0-3}$ alkyl-$O_p$—$C_{0-3}$ alkyl-phenyl, which is unsubstituted or substituted with one or more substituents selected from $R^5$, and (3) —$C_{0-3}$ alkyl-$O_p$—$C_{0-3}$ alkyl-heterocycle, which is unsubstituted or substituted with one or more substituents selected from $R^5$; where p is 0 or 1, (wherein if p is 0, a chemical bond is present in the place of $O_p$);

$R^4$ is selected from the group consisting of:
(1) hydrogen, (2) $C_{1-6}$ alkyl, and (3) hydroxy;
m is 1, 2, or 3; when m is two or more than two, $R^4$ may be the same or different; $R^4$ may form the bond with any carbon atom on the cyclic amine ring;

k is 1;

Y is a carbon atom;

$R^5$ is selected from the group consisting of:
(1) halogen, (2) hydroxy, (3) —(C=O)$_q$—$O_r$—$C_{1-6}$ alkyl, where the alkyl is unsubstituted or substituted with one or more substituents selected from $R^9$, (4) —$O_p$—($C_{1-3}$)perfluoroalkyl, (5) —(C=O)$_q$—O$_r$—C$_{3-8}$ cycloalkyl, where the cycloalkyl is unsubstituted or substituted with one or more substituents selected from R$^9$, (6) —(C=O)$_q$—O$_r$—C$_{2-4}$ alkenyl, where the alkenyl is unsubstituted or substituted with one or more substituents selected from R$^9$, (7) —(C=O)$_q$—O$_r$-phenyl or —(C=O)$_q$—O$_r$-napthyl, where the phenyl or napthyl is unsubstituted or substituted with one or more substituents selected from R$^9$, (8) —(C=O)$_q$—O$_r$-heterocycle, where the heterocycle is unsubstituted or substituted with one or more substituents selected from R$^9$, (9) —(C=O)—NR$^6$R$^7$, (10) —NR$^6$R$^7$, (11) —S(O)$_2$—NR$^6$R$^7$, (12) —S(O)$_t$—R$^8$, where t is 0, 1 or 2, (13) —CO$_2$H, (14) —CN, and (15) —NO$_2$; where p is 0 or 1, (wherein if p is 0, a chemical bond is present in the place of O$_p$) and where q is 0 or 1 and r is 0 or 1 (wherein if q is 0 or r is 0, a bond is present in the place of (C=O)$_q$ or O$_r$, and wherein if q is 0 and r is 0, a single bond is present in the place of (C=O)$_q$—O$_r$);

R$^6$ and R$^7$ are independently selected from the group consisting of:

(1) hydrogen, (2) C$_{1-6}$ alkyl, which is unsubstituted or substituted with R$^5$, (3) C$_{3-6}$ alkenyl, which is unsubstituted or substituted with R$^5$, (4) C$_{3-8}$ cycloalkyl which is unsubstituted or substituted with R$^5$, (5) phenyl, which is unsubstituted or substituted with R$^5$, and (6) heterocycle, which is unsubstituted or substituted with R$^5$, or R$^6$ and R$^7$ taken together with the nitrogen atom to which they are attached form a 3 to 8 membered ring, where the ring may contain one to four heteroatom independently selected from the group consisting of nitrogen, oxygen, and sulfur; where the ring may be saturated or partially saturated or unsaturated; which is unsubstituted or substituted one or more substituents selected from R$^5$;

R$^8$ is selected from the definitions of R$^6$ and R$^7$;

R$^9$ is selected from the group consisting of:

(1) hydroxy, (2) halogen, (3) C$_{1-6}$ alkyl, (4) —C$_{3-8}$ cycloalkyl, (5) —O—C$_{1-6}$ alkyl, (6) —O(C=O)—C$_{1-6}$ alkyl, (7) —NH—C$_{1-6}$ alkyl, (8) phenyl, (9) heterocycle, (10) —CO$_2$H, and (11) —CN;

or a pharmaceutically acceptable salt thereof.

2. The compound as claimed in claim 1, wherein

R$^1$ is independently selected from the group consisting of:
(1) hydrogen, (2) halogen, (3) hydroxy, (4) —O$_p$—C$_{1-6}$ alkyl, where the alkyl is unsubstituted or substituted with one or more substituents selected from R$^5$, and (5) —O$_p$—C$_{3-8}$ cycloalkyl, where the cycloalkyl is unsubstituted or substituted with one or more substituents selected from R$^5$; where p is 0 or 1 (wherein if p is 0, a chemical bond is present in the place of O$_p$);

n is 1, 2, or 3; when n is two or more than two, R$^1$ may be the same or different;

R$^3$ is 3 to 8 membered ring where the ring may contain one to four heteroatom independently selected from the group consisting of nitrogen, oxygen, and sulfur; where the ring may be saturated or unsaturated; and where the ring is optionally substituted with 1 to 4 substituents independently selected from the group consisting of: (1) hydroxy, (2) halogen, (3) C$_{1-6}$ alkyl, which is unsubstituted or substituted with one or more substituents selected from R$^5$, (4) C$_{3-8}$ cycloalkyl, which is unsubstituted or substituted with one or more substituents selected from R$^5$, (5) —O—C$_{1-6}$ alkyl, which is unsubstituted or substituted with one or more substituents selected from R$^5$, and (6) —O—C$_{3-8}$ cycloalkyl, which is unsubstituted or substituted with one or more substituents selected from R$^5$;

R$^5$ is selected from the group consisting of:

(1) halogen, (2) hydroxy, (3) —(C=O)$_q$—O$_r$—C$_{1-6}$ alkyl, where the alkyl is unsubstituted or substituted with one or more substituents selected from R$^9$, (4) —O$_p$—(C$_{1-3}$)perfluoroalkyl, (5) —(C=O)$_q$—O$_r$—C$_{3-8}$ cycloalkyl, where the cycloalkyl is unsubstituted or substituted with one or more substituents selected from R$^9$, (6) —(C=O)$_q$—O$_r$-phenyl, where the phenyl is unsubstituted or substituted with one or more substituents selected from R$^9$, (7) —(C=O)$_q$—O$_r$-heterocycle, where the heterocycle is unsubstituted or substituted with one or more substituents selected from R$^9$, (8) —(C=O)—NR$^6$R$^7$, (9) —NR$^6$R$^7$, (10) —S(O)$_2$—NR$^6$R$^7$, and (11) —S(O)$_t$—R$^8$, where t is 0, 1 or 2; where p is 0 or 1, (wherein if p is 0, a chemical bond is present in the place of O$_p$) and where q is 0 or 1 and r is 0 or 1 (wherein if q is 0 or r is 0, a bond is present in the place of (C=O)$_q$ or O$_r$, and wherein if q is 0 and r is 0, a single bond is present in the place of (C=O)$_q$—O$_r$);

R$^9$ is selected from the group consisting of:

(1) hydroxy, (2) halogen, (3) C$_{1-6}$ alkyl, (4) —C$_{3-8}$ cycloalkyl, (5) —O—C$_{1-6}$ alkyl, (6) —O(C=O)—C$_{1-6}$ alkyl, (7) —NH—C$_{1-6}$ alkyl, (8) phenyl, and (9) heterocycle;

or a pharmaceutically acceptable salt thereof.

3. A pharmaceutical composition comprising the compound or the pharmaceutically acceptable salt thereof, as claimed in claim 1, and a pharmaceutically acceptable carrier.

4. A method for the treatment of pain, depression or anxiety in a mammalian subject, which comprises administering to a mammal in need of such treatment a therapeutically effective amount of the compound or the pharmaceutically acceptable salt thereof, as claimed in claim 1.

5. The method as claimed in claim 4, wherein the mammal is a human.

* * * * *